US011738099B2

(12) United States Patent
Lu et al.

(10) Patent No.: US 11,738,099 B2
(45) Date of Patent: *Aug. 29, 2023

(54) MOLECULAR PROBES AND METHODS OF USE

(71) Applicant: CASE WESTERN RESERVE UNIVERSITY, Cleveland, OH (US)

(72) Inventors: Zheng-Rong Lu, Beachwood, OH (US); Zheng Han, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 310 days.

This patent is subject to a terminal disclaimer.

(21) Appl. No.: 17/182,997

(22) Filed: Feb. 23, 2021

(65) Prior Publication Data

US 2021/0275695 A1  Sep. 9, 2021

Related U.S. Application Data

(63) Continuation of application No. 15/821,943, filed on Nov. 24, 2017, now Pat. No. 10,925,980, which is a continuation-in-part of application No. 15/502,160, filed as application No. PCT/US2015/043668 on Aug. 4, 2015, now Pat. No. 10,124,073.

(60) Provisional application No. 62/425,805, filed on Nov. 23, 2016, provisional application No. 62/032,945, filed on Aug. 4, 2014.

(51) Int. Cl.
A61K 49/14 (2006.01)
A61K 49/00 (2006.01)
A61K 51/08 (2006.01)

(52) U.S. Cl.
CPC .......... *A61K 49/14* (2013.01); *A61K 49/0032* (2013.01); *A61K 49/0056* (2013.01); *A61K 51/088* (2013.01)

(58) Field of Classification Search
CPC .... A61K 49/00; A61K 49/14; A61K 49/0032; A61K 49/0056; A61K 51/00; A61K 51/08; A61K 51/088
USPC ........ 424/1.11, 1.65, 1.69, 9.1, 9.2, 9.3, 9.4, 424/9.5, 9.6; 534/7, 10–16; 530/300
See application file for complete search history.

(56) References Cited

U.S. PATENT DOCUMENTS

| | | | |
|---|---|---|---|
| 5,622,718 A | 4/1997 | Al-Shamkhani et al. | |
| 5,700,848 A | 12/1997 | Soon-Shiong et al. | |
| 6,472,506 B1 | 10/2002 | Moreau et al. | |
| 10,124,073 B2 * | 11/2018 | Lu | C07K 14/78 |
| 10,627,402 B2 * | 4/2020 | Choi | A61K 49/0008 |
| 10,653,801 B2 * | 5/2020 | Lu | A61K 49/0054 |
| 10,925,980 B2 * | 2/2021 | Lu | A61K 49/0032 |
| 2003/0161791 A1 | 8/2003 | Bentley et al. | |
| 2004/0028745 A1 | 2/2004 | Bouhadir et al. | |
| 2005/0271705 A1 | 12/2005 | Hughes et al. | |
| 2008/0221208 A1 | 9/2008 | Palczewski et al. | |
| 2010/0035986 A1 | 2/2010 | Maeda et al. | |
| 2011/0288170 A1 | 11/2011 | Palczewski et al. | |
| 2012/0244070 A1 | 9/2012 | Lu et al. | |
| 2013/0011334 A1 | 1/2013 | Steuernagel et al. | |
| 2017/0322213 A1 | 11/2017 | Choi et al. | |
| 2018/0110886 A1 | 4/2018 | Lu et al. | |

FOREIGN PATENT DOCUMENTS

| | | |
|---|---|---|
| CN | 101745119 A | 6/2010 |
| EP | 3223016 A1 | 9/2017 |
| GB | 1334980 A | 10/1973 |
| WO | 2001/75067 A2 | 10/2001 |
| WO | 2006/026020 A2 | 3/2006 |
| WO | 2016/080633 A1 | 5/2016 |

OTHER PUBLICATIONS

Han et al, Bioconjugate Chem., vol. 28, pp. 1031-1040 (Year: 2017).*
Han et al, Nature Communications, vol. 8, No. 692, pp. 1-9 (Year: 2017).*
Li et al, Molecular Pharmaceutics, vol. 14, pp. 3906-3915 (Year: 2017).*
Extended European Search Report for Application No. 15829365-4-1453/3177638, 2017.
Han et al.: "An EDB fibronectin specific contrast agent for molecular imaging of cancer metastasis", 23rd Annual Meeting & Exhibition May 30-Jun. 5, 2015, Proc. Intl. Soc. Mag. Reson. Med., vol. 23 Jun. 3, 2015 (Jun. 3, 2015).
Han et al.: "EDB Fibronectin Specific Peptide for Prostate Cancer Targeting", Bioconjugate Chemistry, vol. 26, No. 5, May 20, 2015 (May 20, 2015), pp. 830-838.
Sun et al.: "MRI of Breast Tumor Initiating Cells Using the Extra Domain-B of Fibronectin Targeting Nanoparticles", Theranosti CS, vol. 4, No. 8, Jan. 1, 2014 (Jan. 1, 2014), pp. 845-885.
Supplementary European Search Report for Application No. 15829365. 4-1453/3177638, 2018.
Wei et al.: "Screening and identifying of homing peptides to bladder cancer BIU-87 identifying of homing peptides to bladder cancer BIU-87 cells in Chinese", Chin. J. Cancer Biother, vol. 20, 5, Oct. 2013 (Oct. 2013), p. 015-521.
Zonghua Liu, et al.; "Polysaccharides-based nanoparticles as drug delivery systems"; Advanced Drug Delivery Reviews; Journal; www elsevier.com/locate/addr, Sep. 17, 2008; 13 pgs.

(Continued)

Primary Examiner — D. L. Jones
(74) Attorney, Agent, or Firm — TAROLLI, SUNDHEIM, COVELL & TUMMINO, LLP

(57) ABSTRACT

A molecular probe comprising a linear peptide that includes an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9; a contrast agent; and a non-peptide linker that covalently links the peptide to the contrast agent.

9 Claims, 41 Drawing Sheets
Specification includes a Sequence Listing.

(56) References Cited

OTHER PUBLICATIONS

Applicant: Case Western Reserve University; "International Search Report and Written Opinion"; International PCT Application No. PCT/US2012/066847; International Filing Date: Nov. 28, 2012; dated Mar. 18, 2013 13 pgs.

* cited by examiner

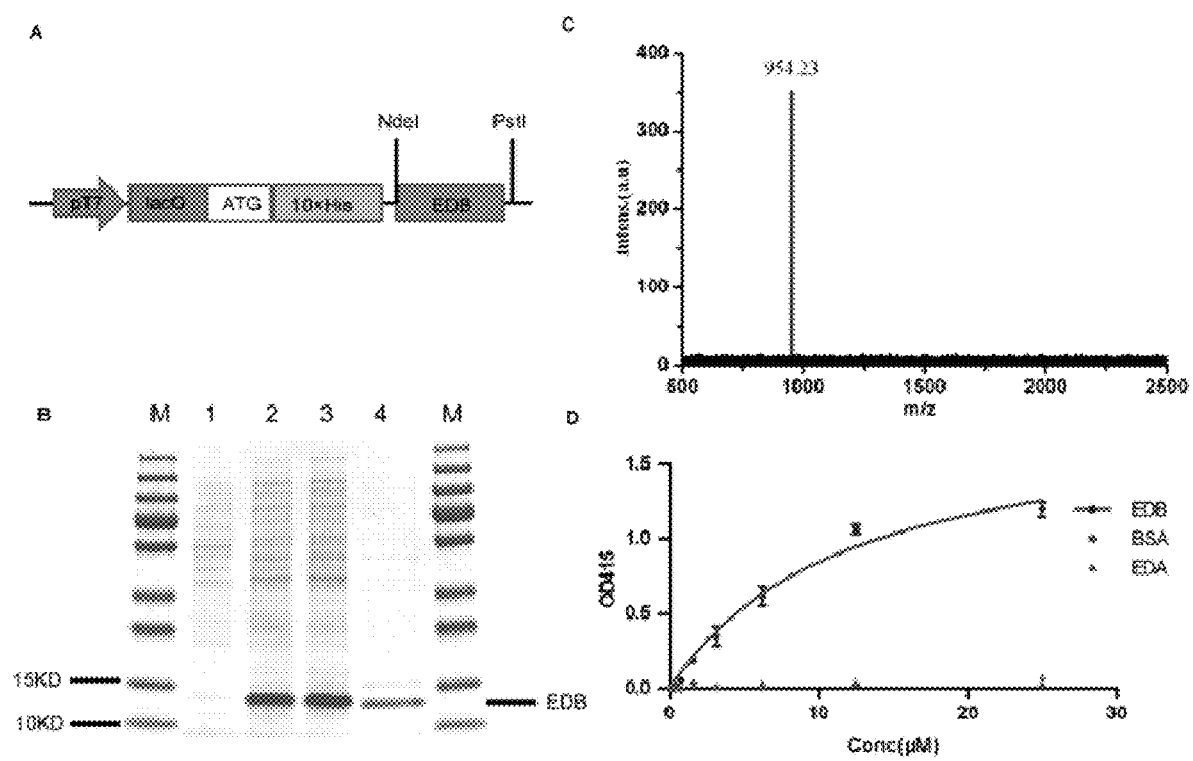
Figs. 1A-D
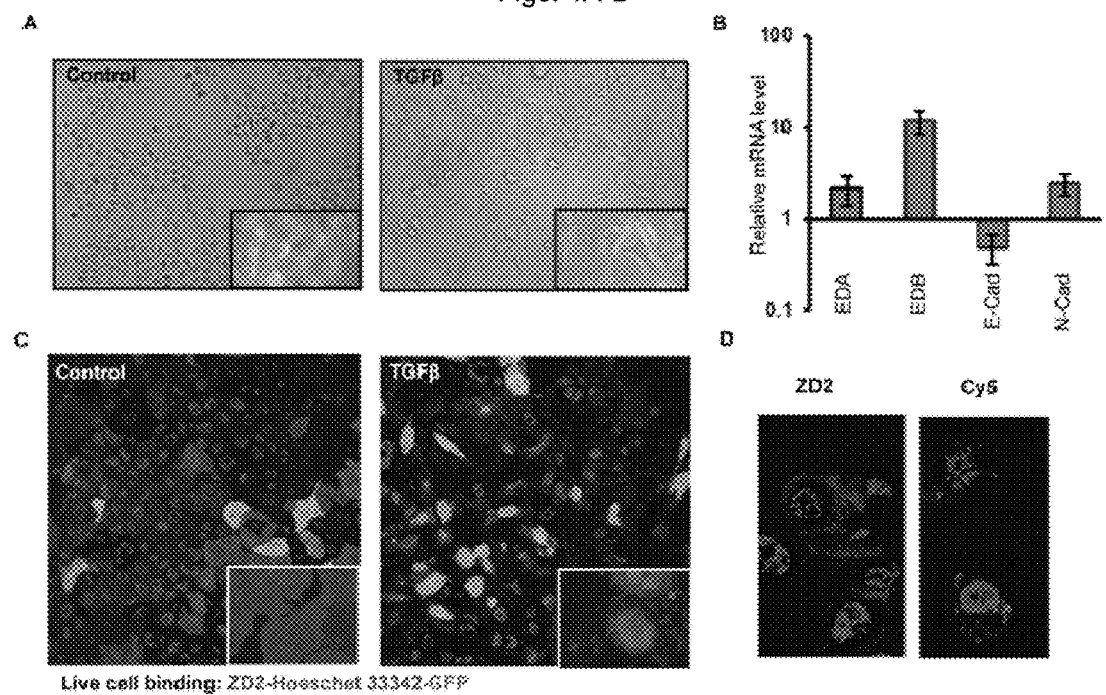
Figs. 2A-D

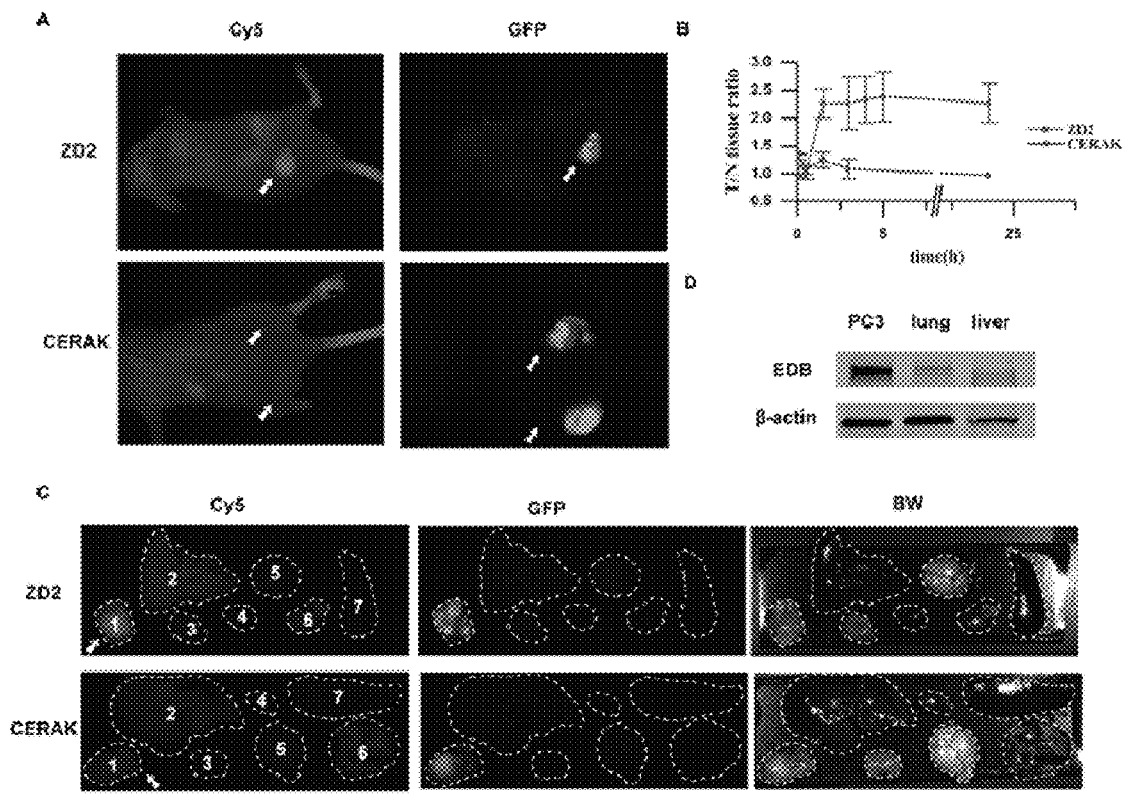
Figs. 3A-D
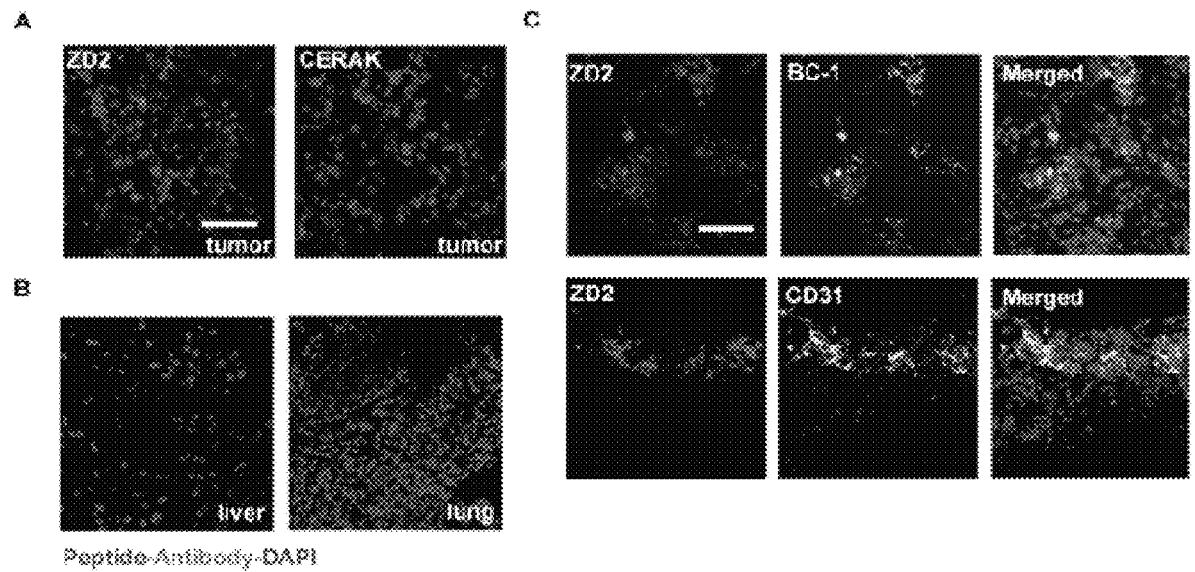
Figs. 4A-C

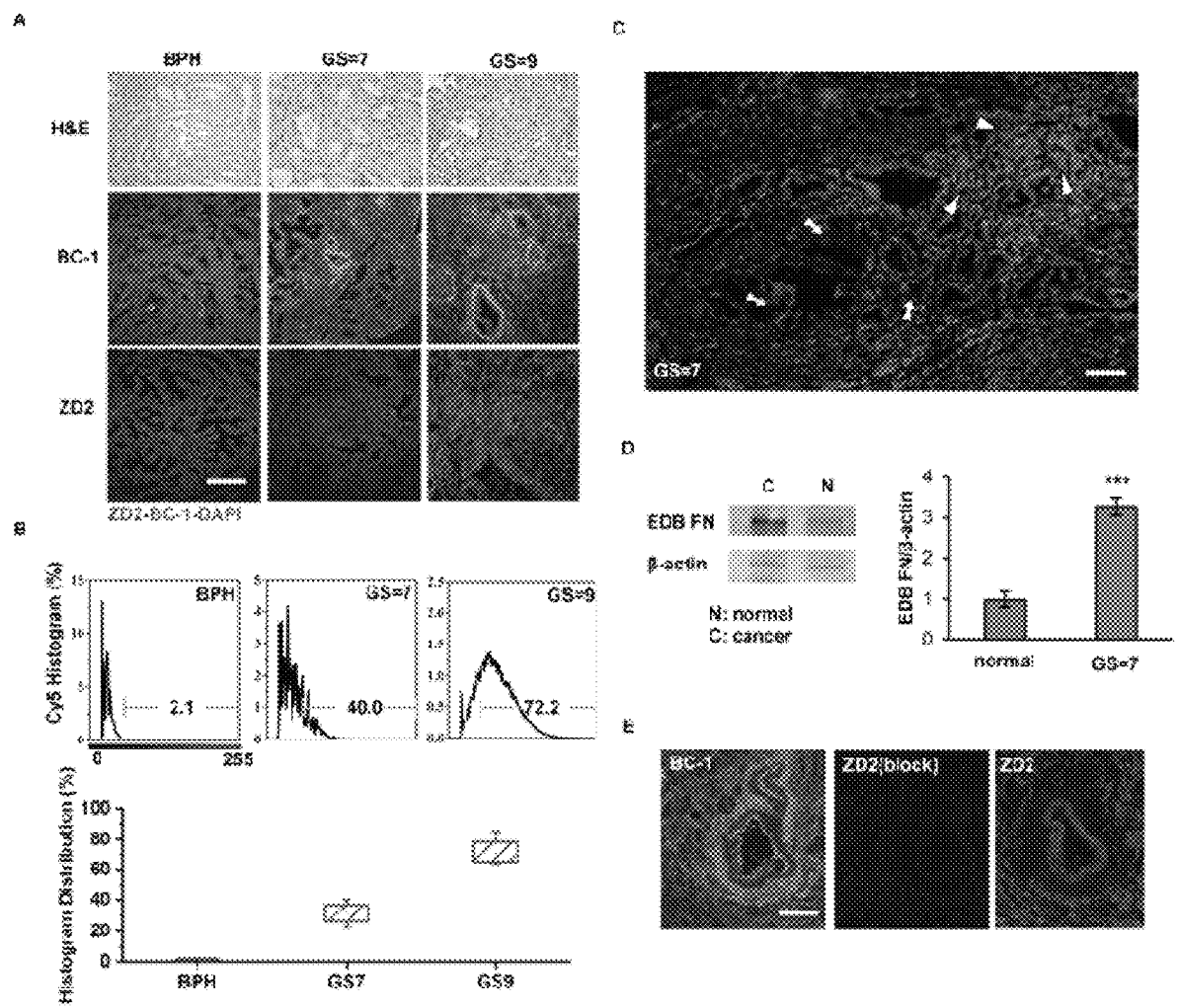
Figs. 5A-E

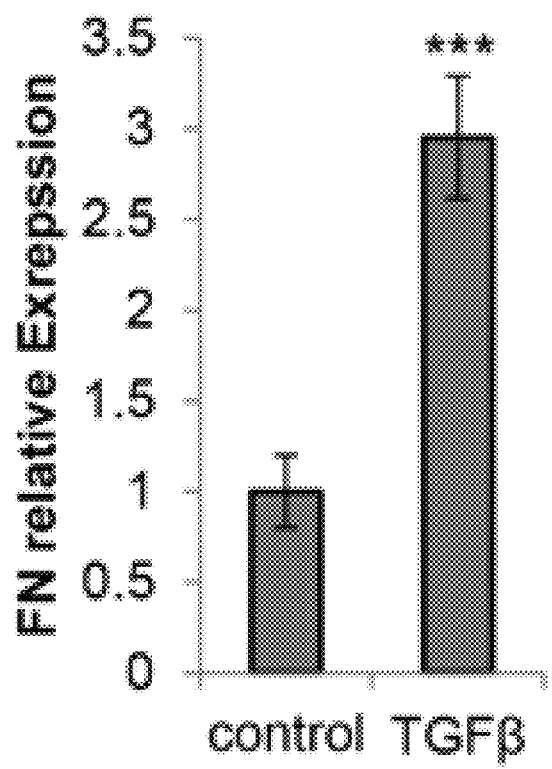
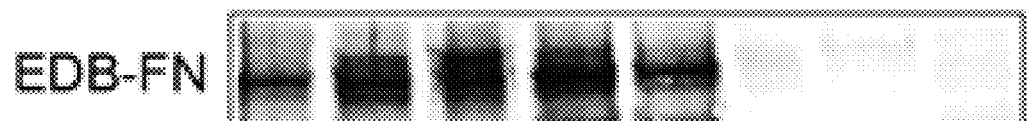
Figs. 6A-B

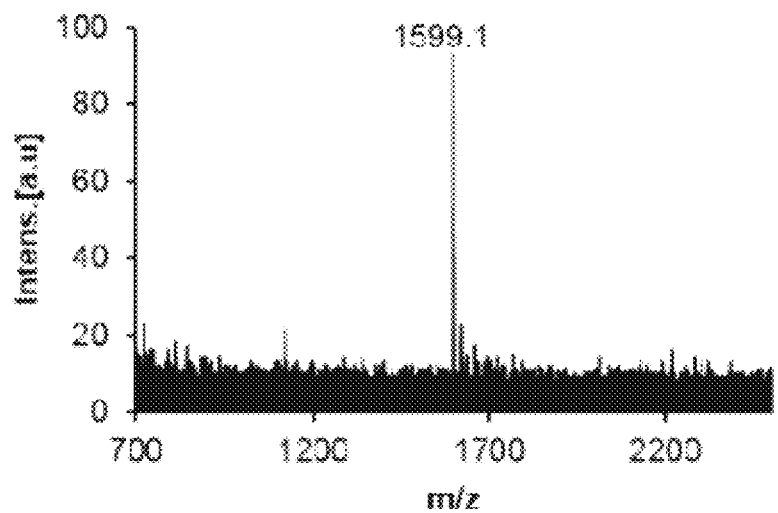
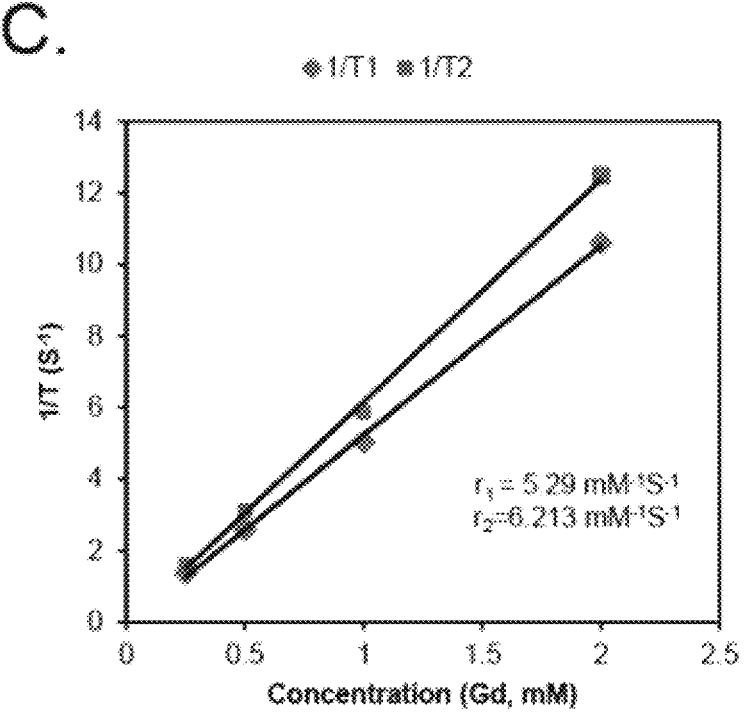
Figs. 7B-C

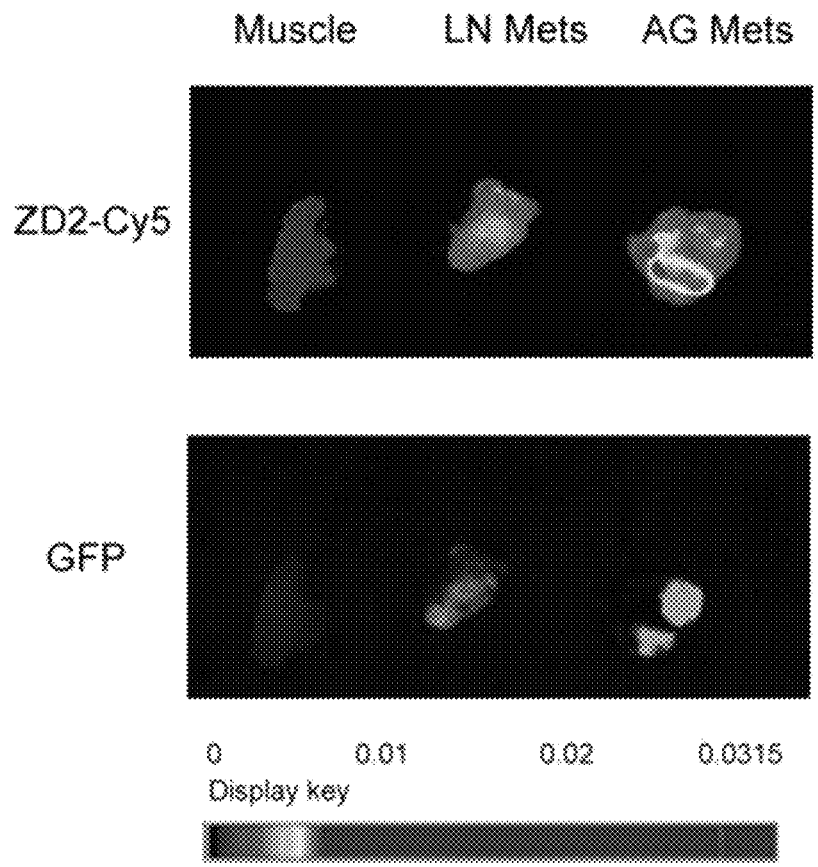
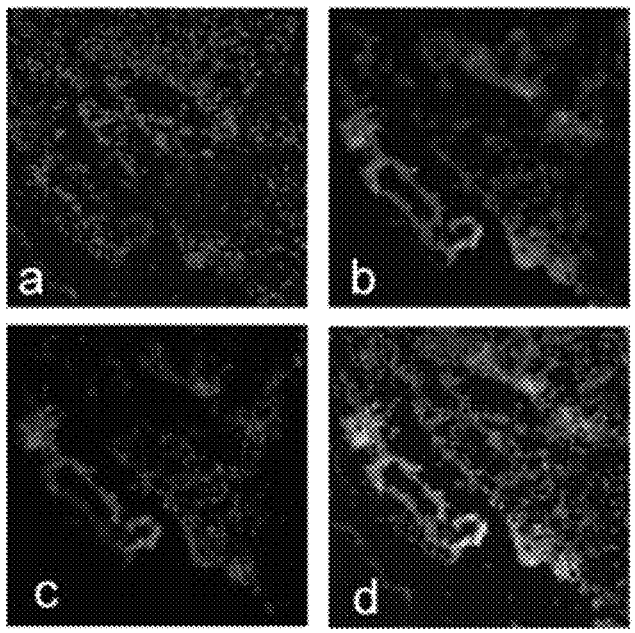
Figs. 8B-C

A.
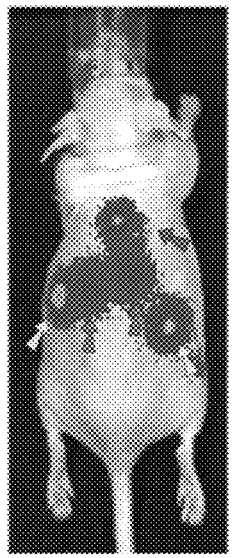  
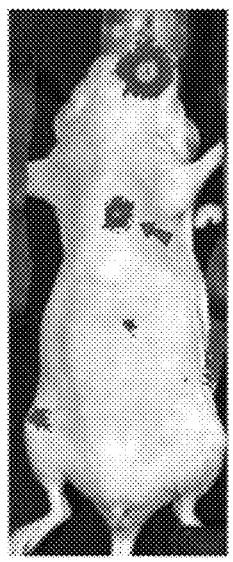 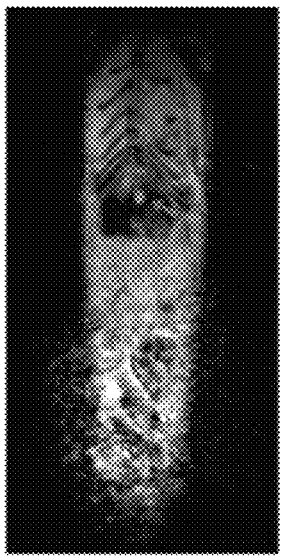 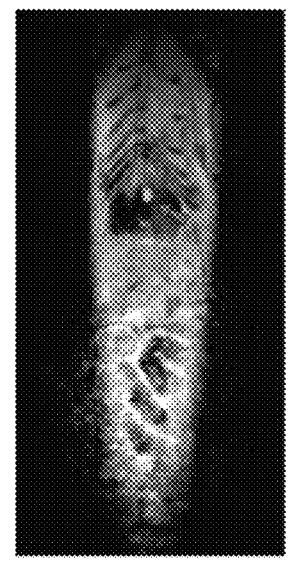
Fig. 9A

B.
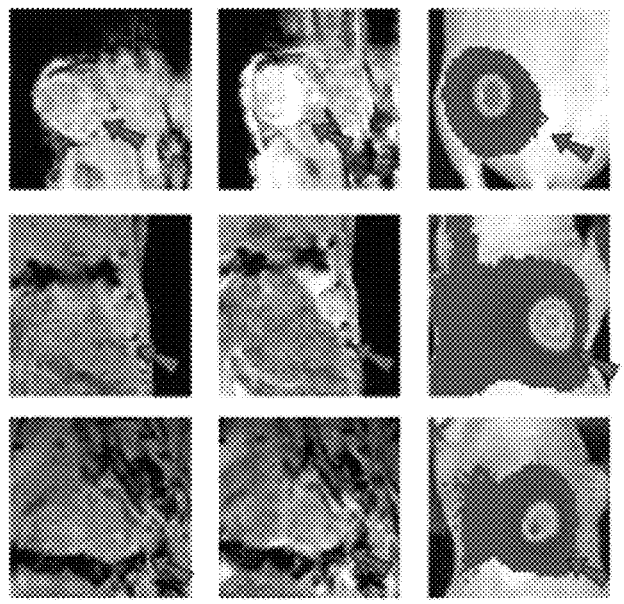
C.
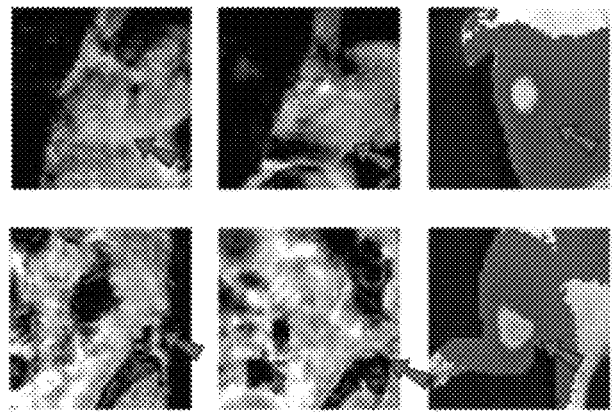
Figs. 9B-C

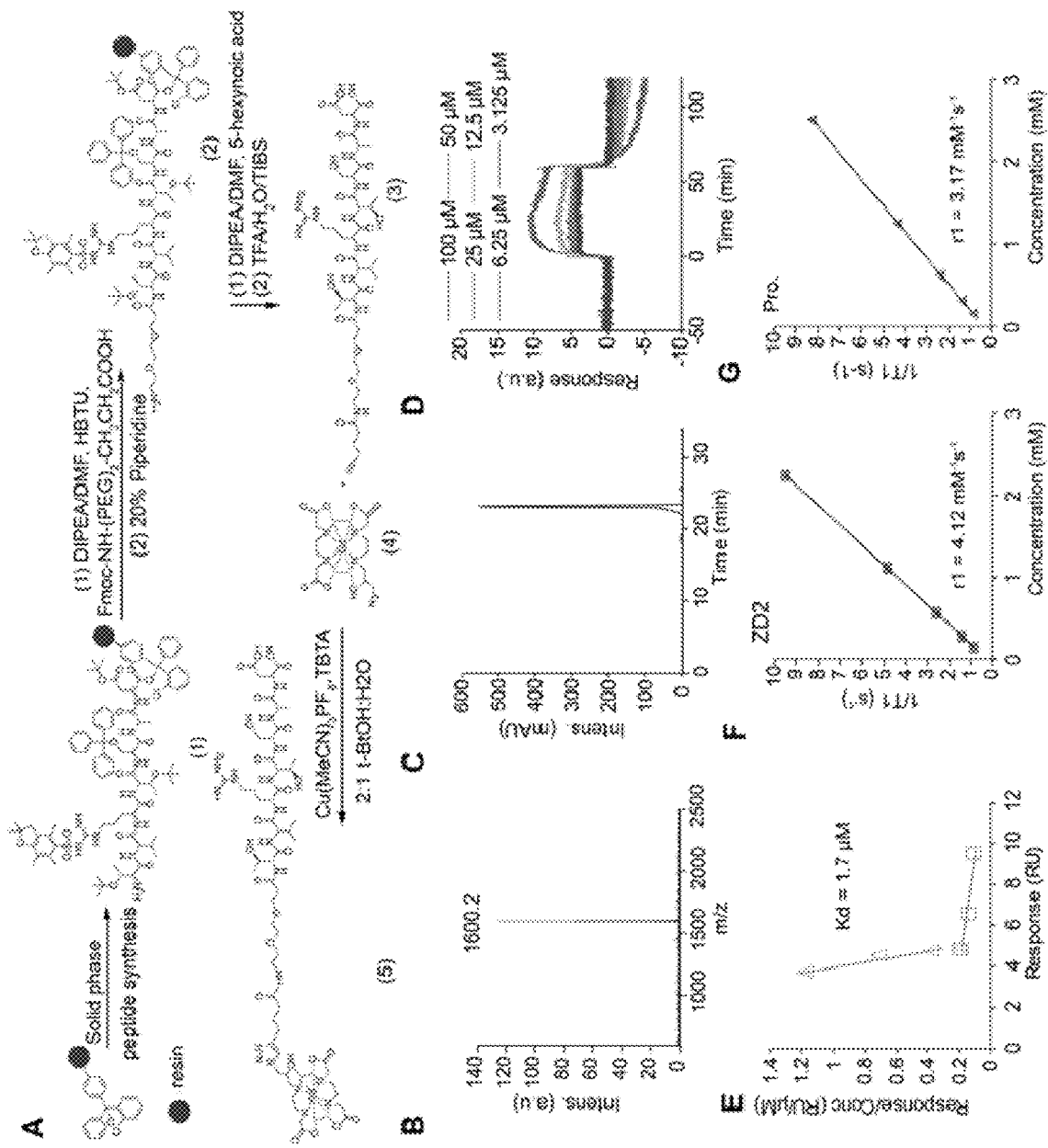
Figs. 15A-G

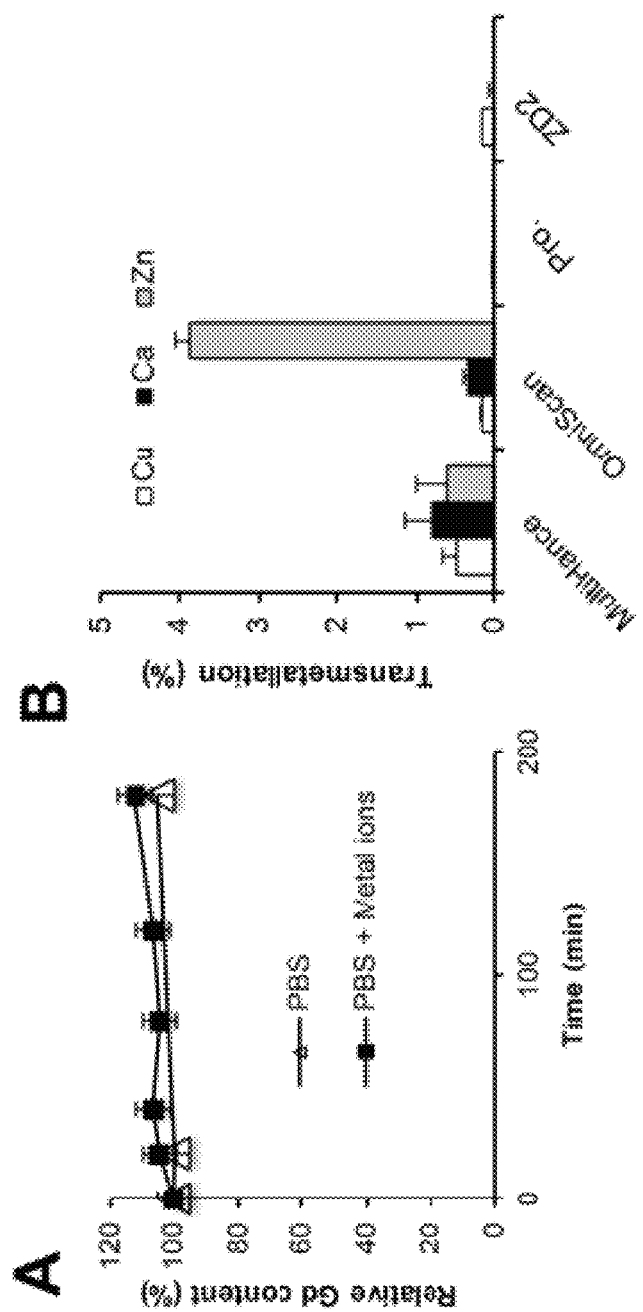
Figs. 16A-B

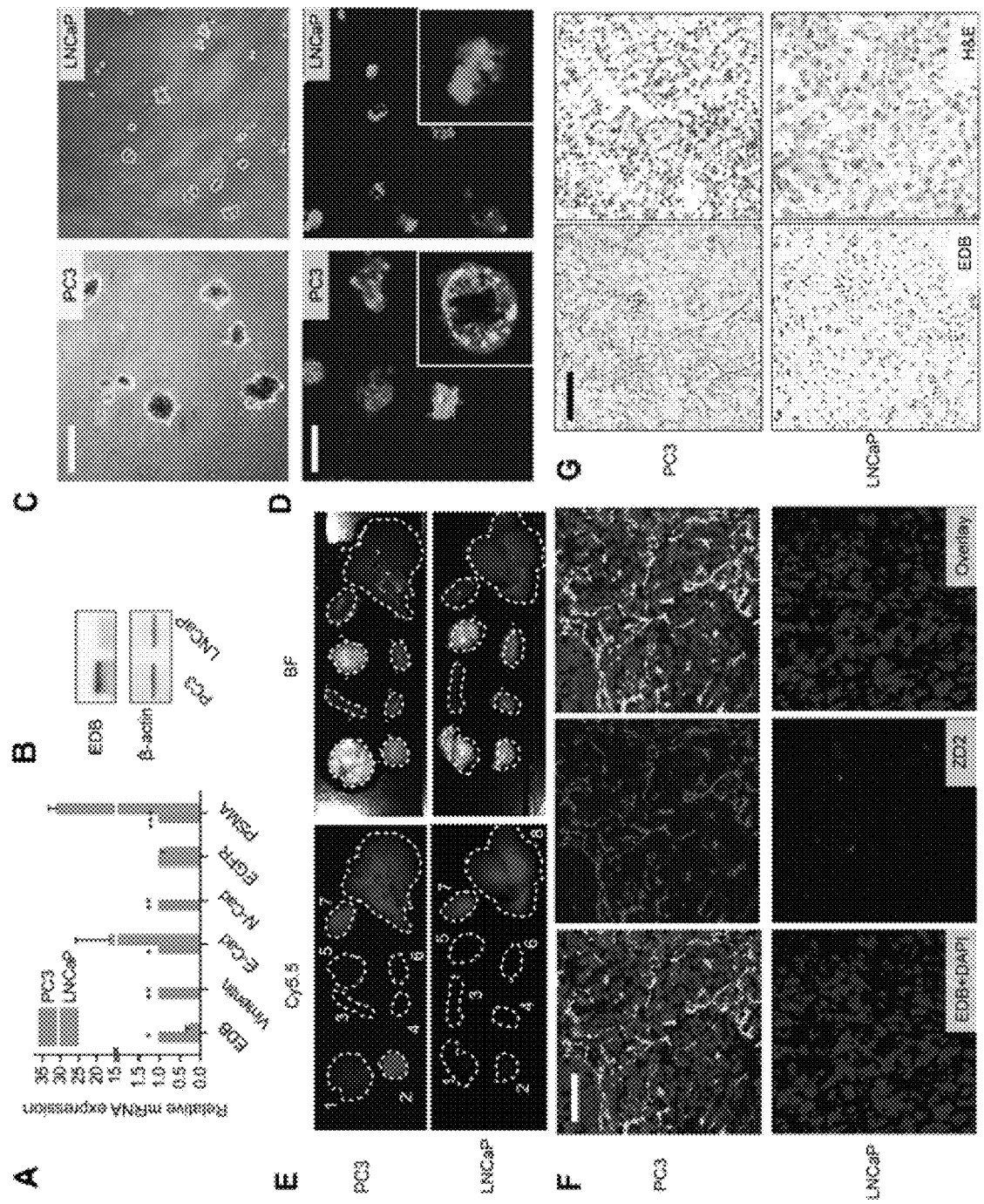
Figs. 17A-G

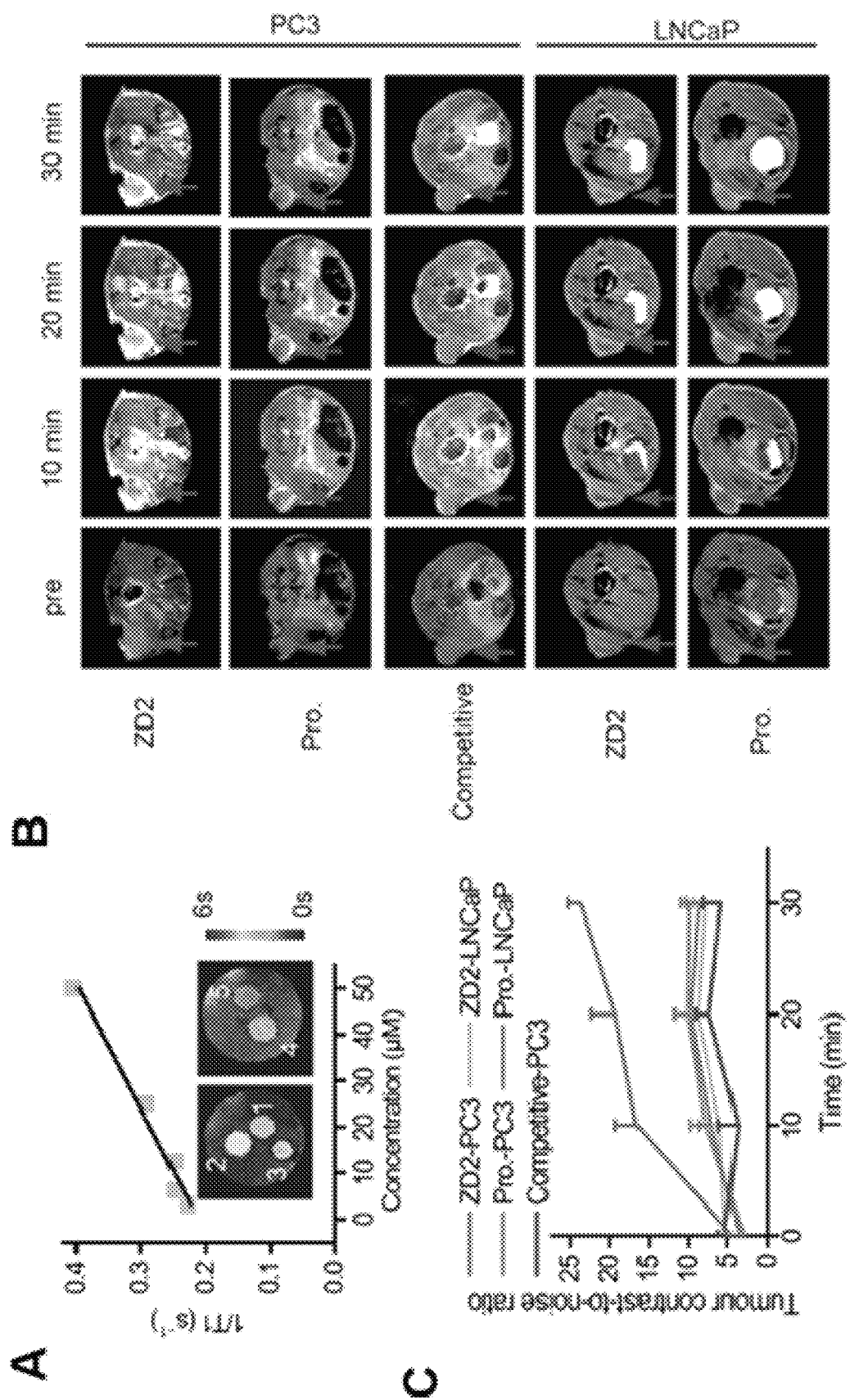
Figs. 18A-C

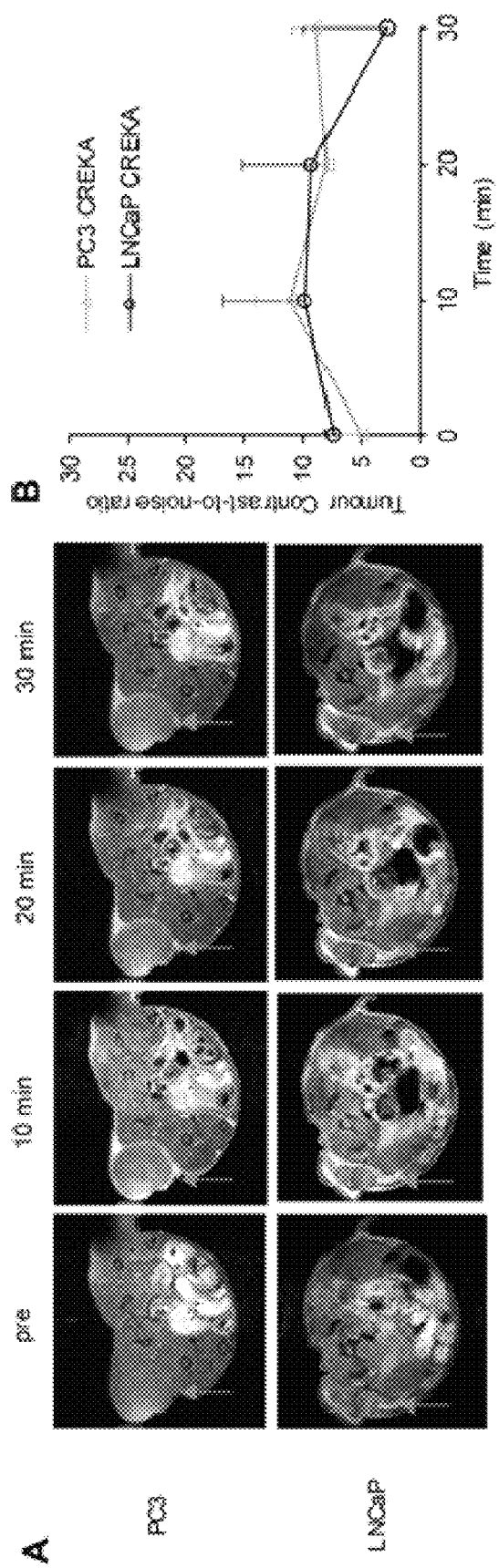
Figs. 19A-B

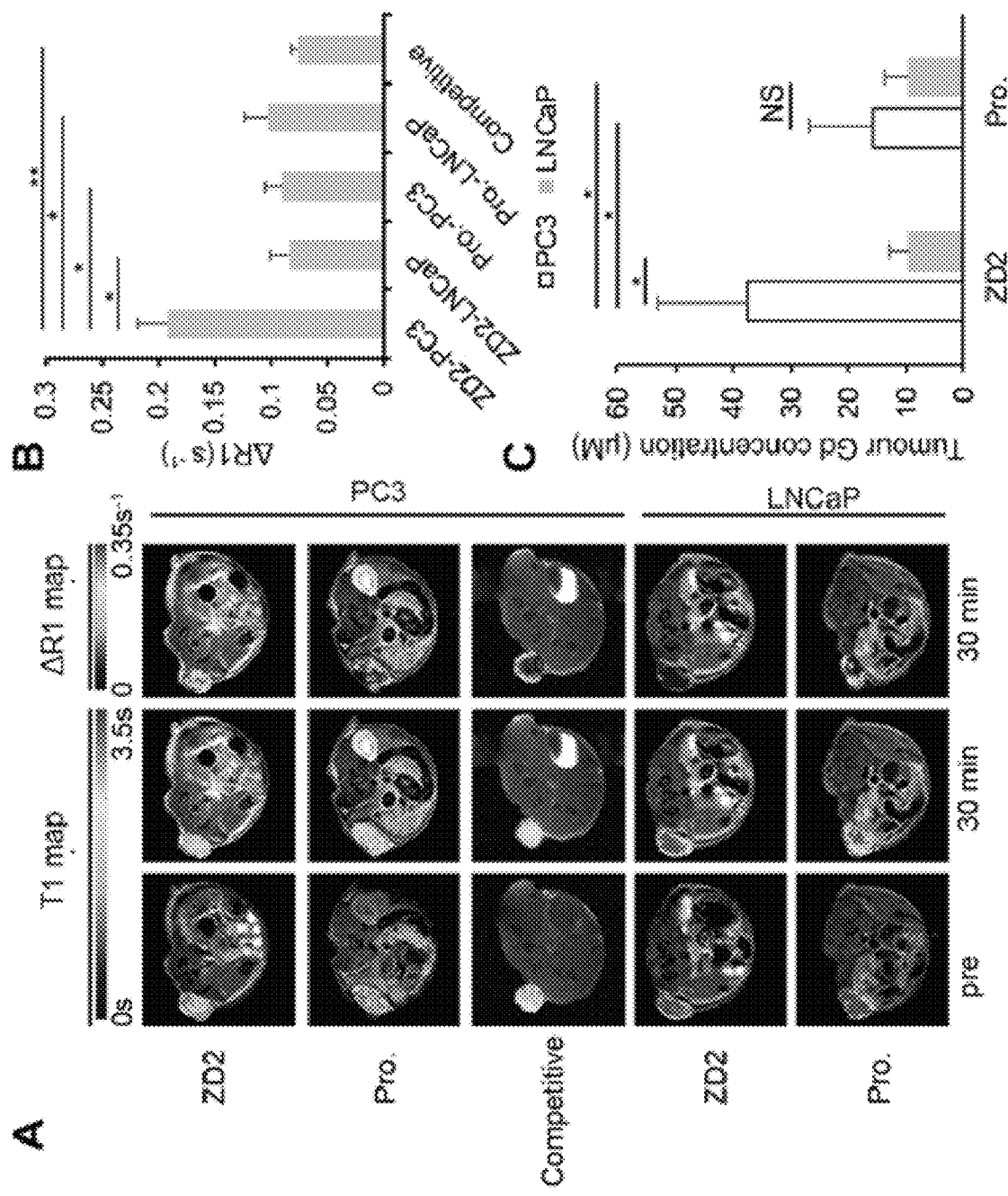
Figs. 20A-C

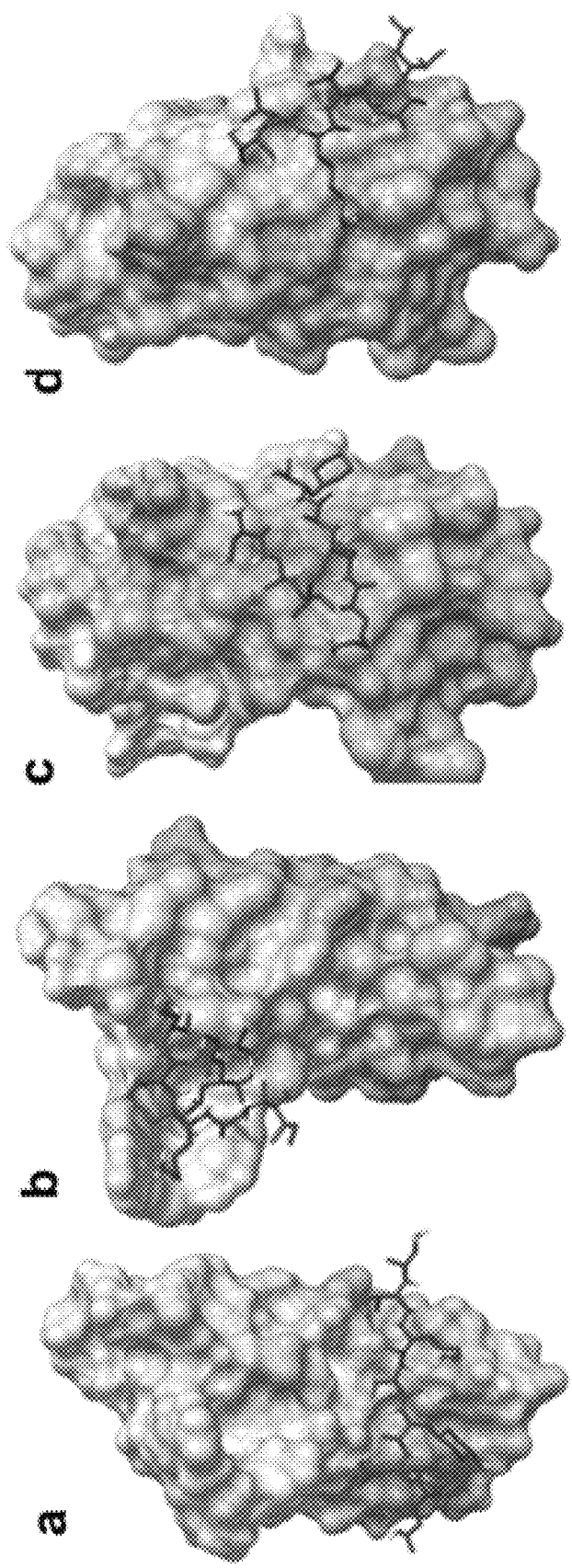
Figs. 22A-D

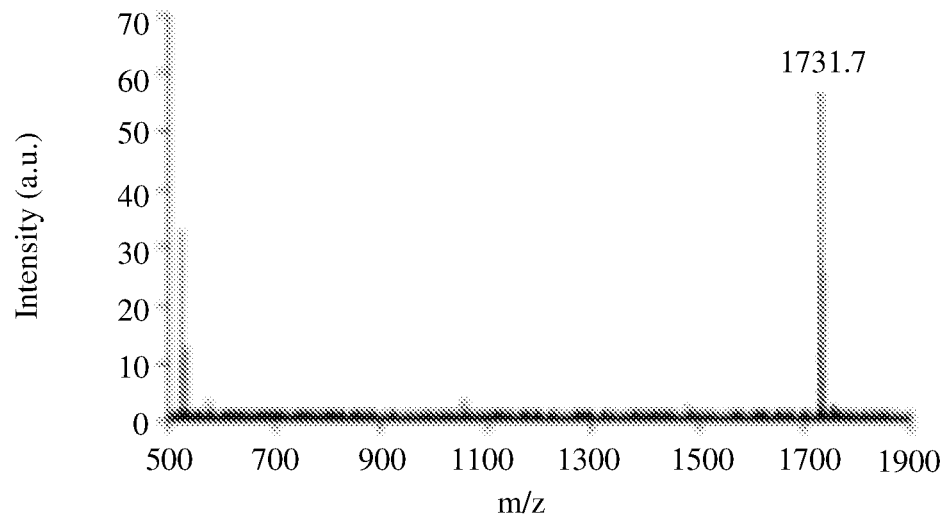
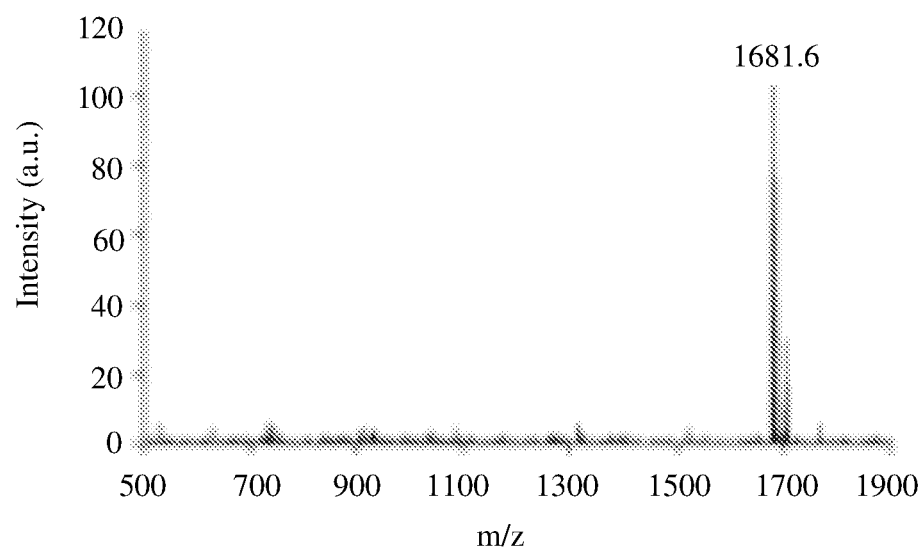
Fig. 25
(Continued)

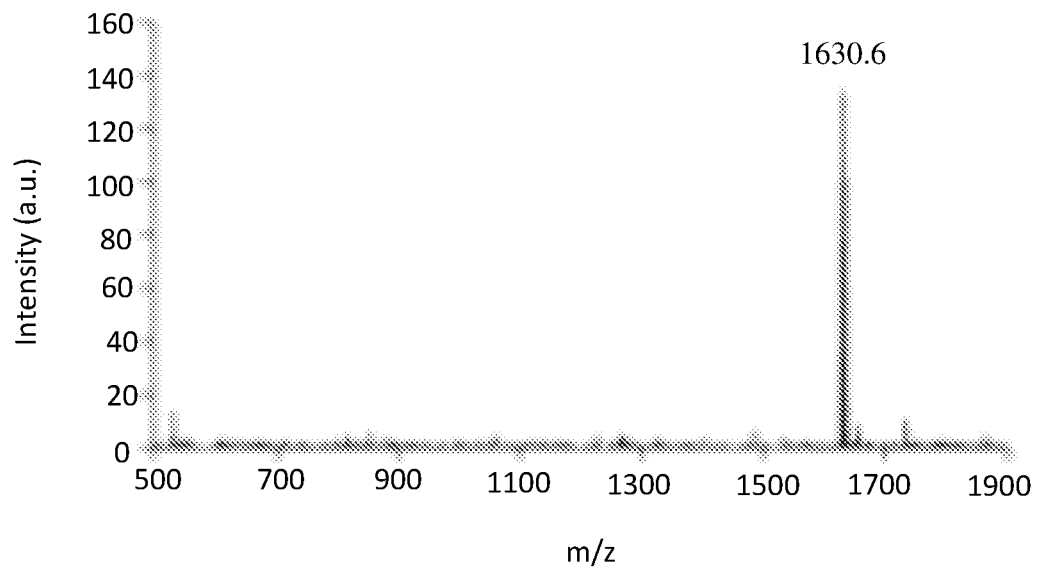
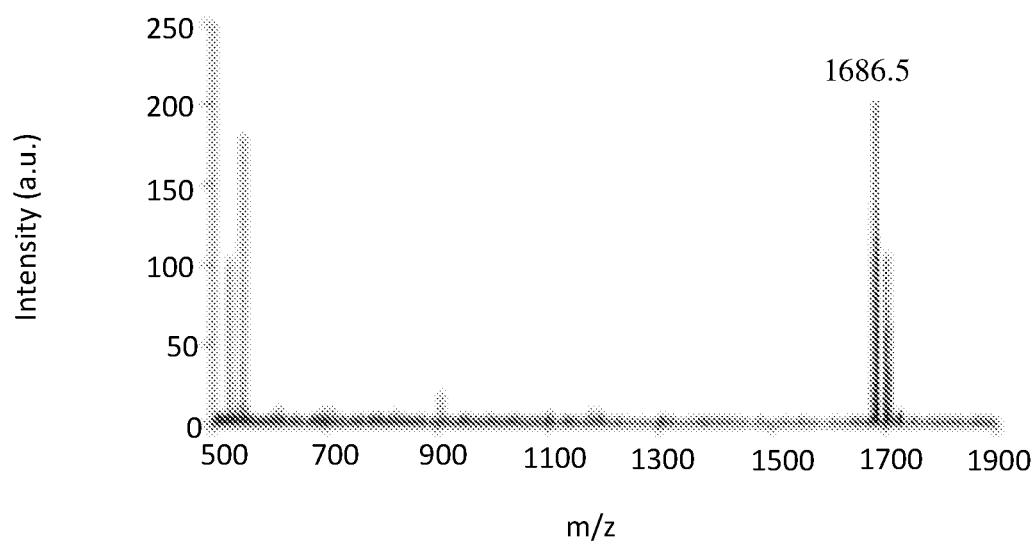
Fig. 25 (Continued)

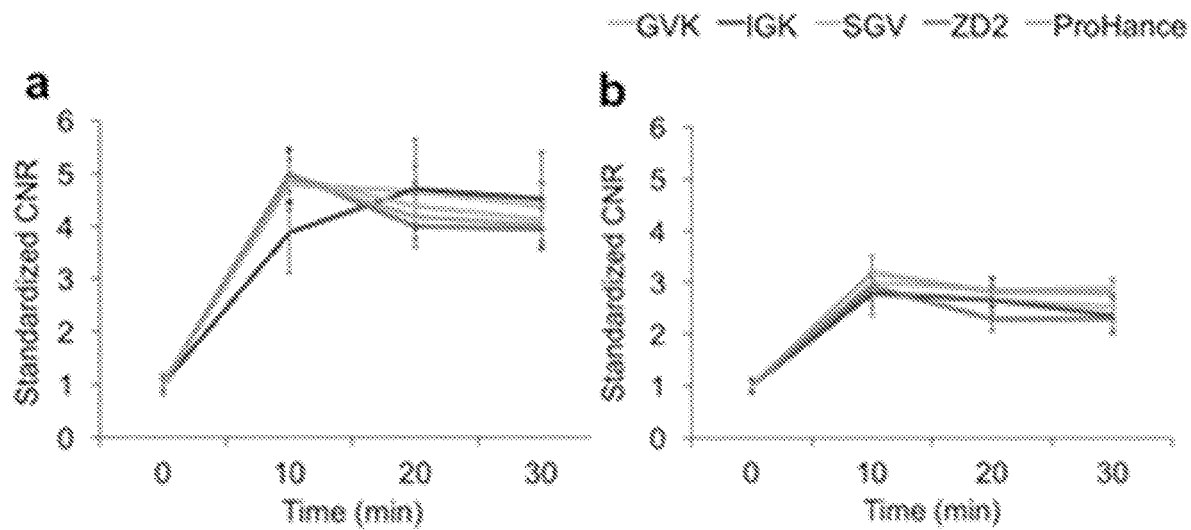
Fig. 29A
Fig. 29B
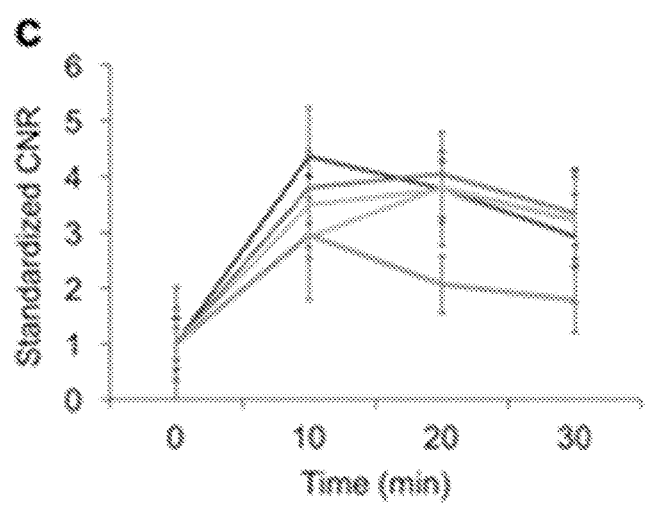
Fig. 29C

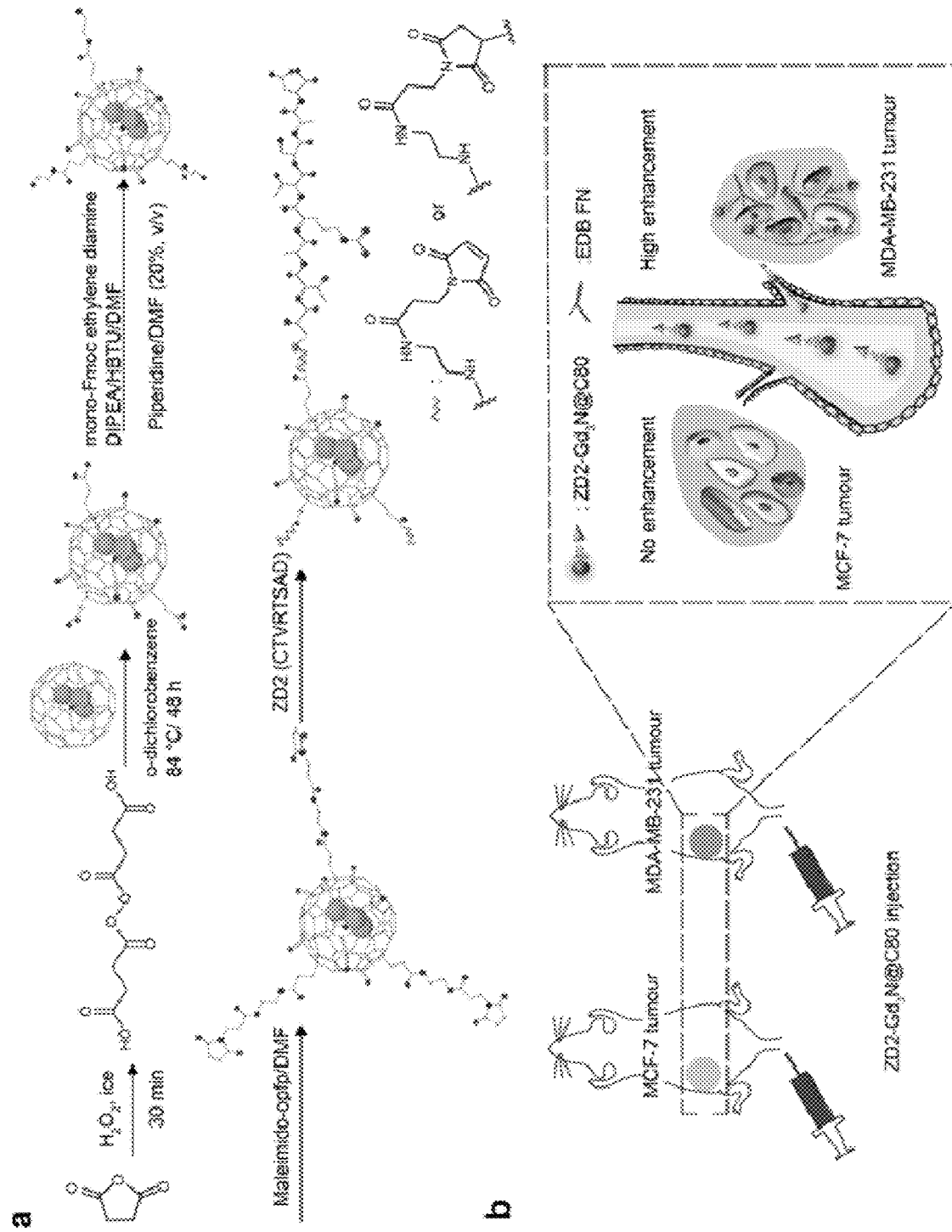
Figs. 30A-B

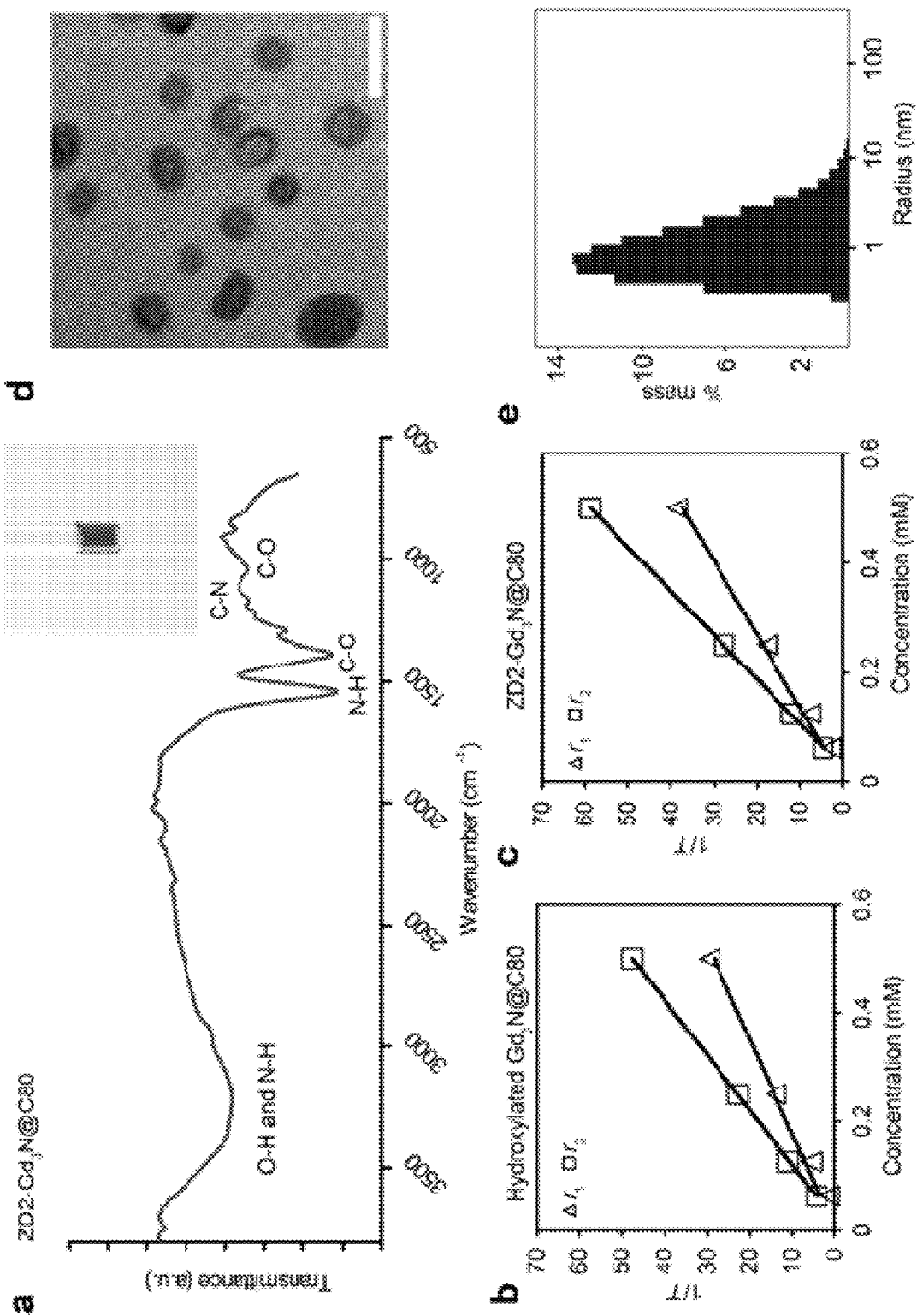
Figs. 31A-E

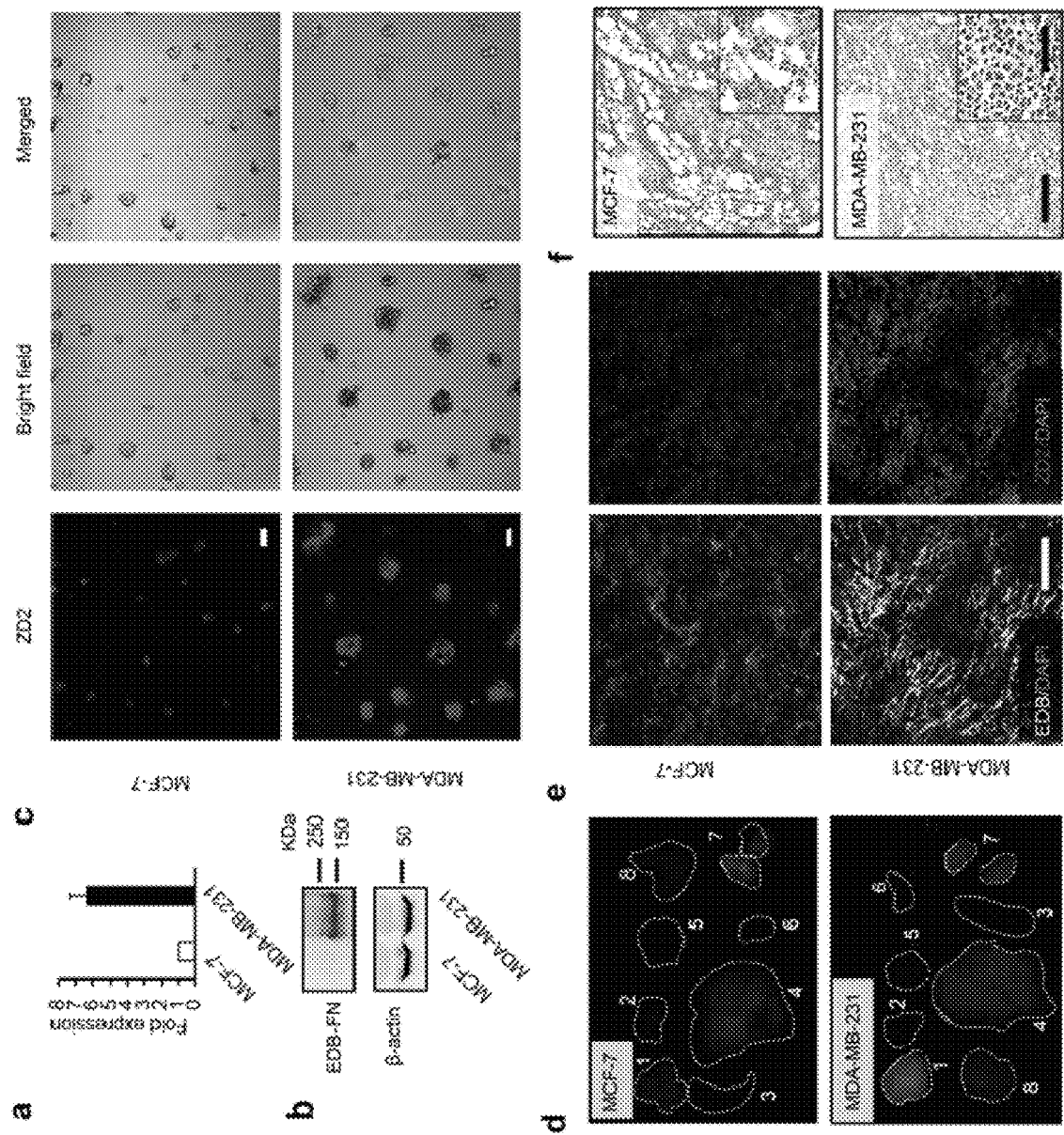
Figs. 32A-F

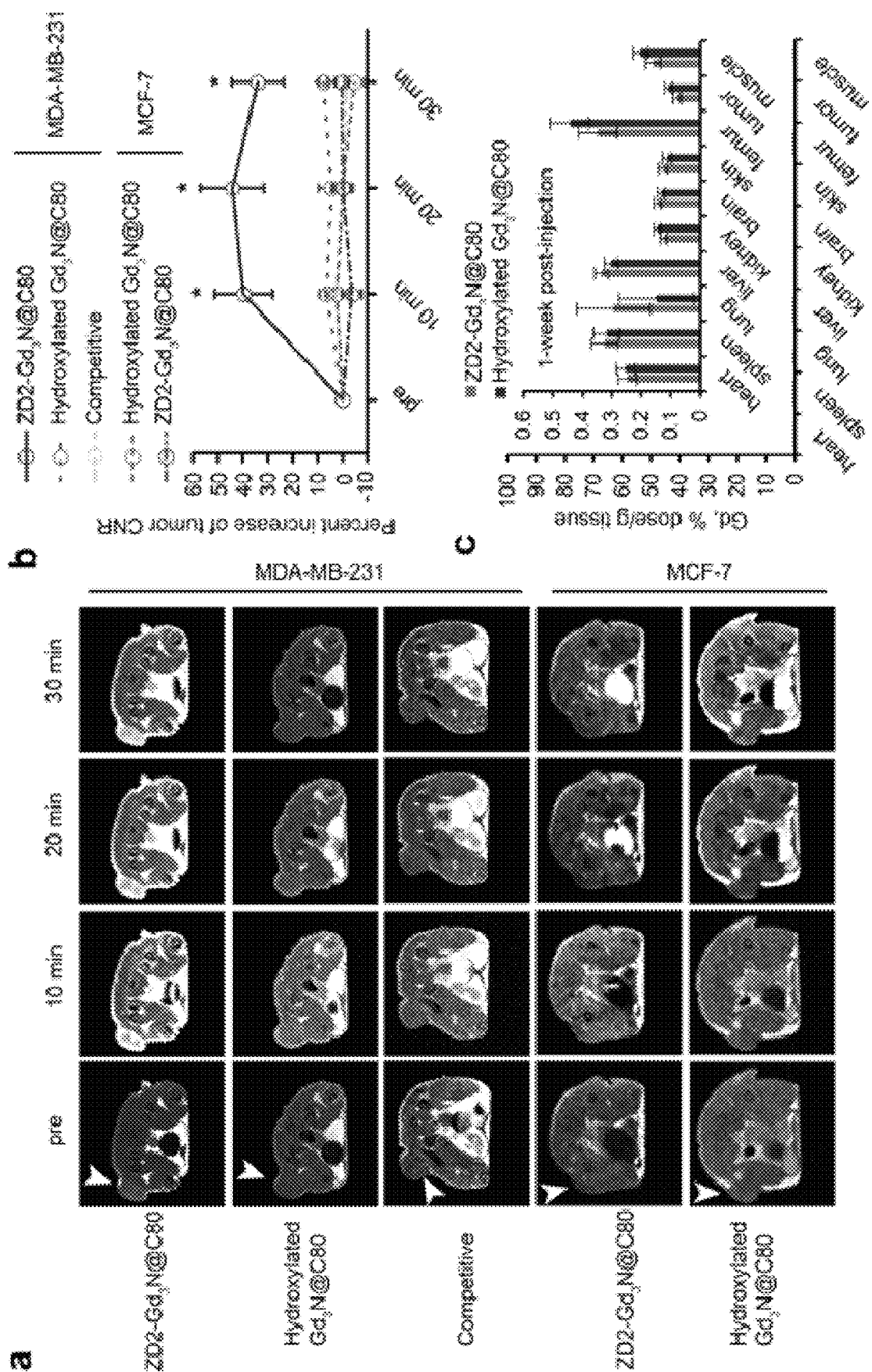
Figs. 33A-C

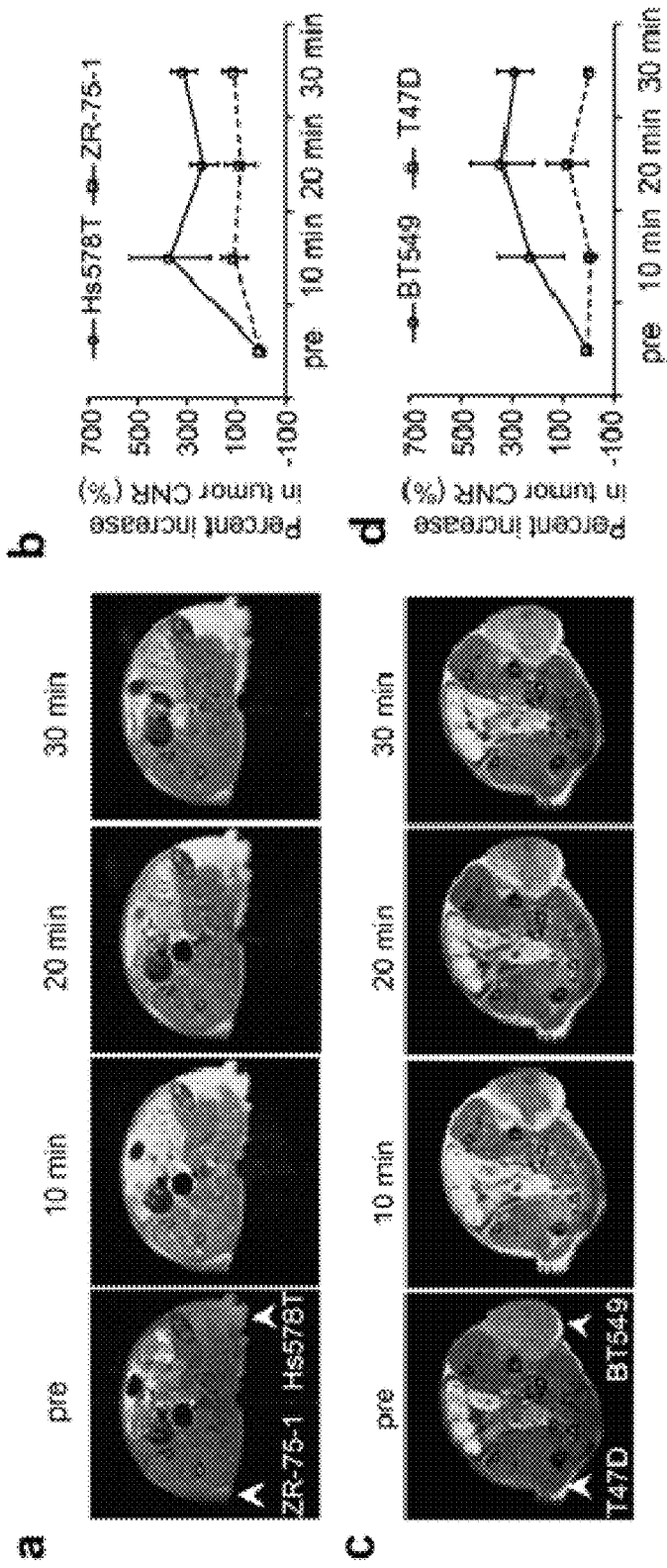
Figs. 34A-D

```
                       SEQUENCE LISTING

<160> NUMBER OF SEQ ID NOS: 59

<210> SEQ ID NO 1
<211> LENGTH: 7
<212> TYPE: PRT
<213> ORGANISM: Homo sapiens

<400> SEQUENCE: 1

Thr Val Arg Thr Ser Ala Asp
1               5

<210> SEQ ID NO 2
<211> LENGTH: 7
<212> TYPE: PRT
<213> ORGANISM: Homo sapiens

<400> SEQUENCE: 2

Asn Trp Gly Asp Arg Ile Leu
1               5

<210> SEQ ID NO 3
<211> LENGTH: 7
<212> TYPE: PRT
<213> ORGANISM: Homo sapiens

<400> SEQUENCE: 3

Asn Trp Gly Lys Pro Ile Lys
1               5

<210> SEQ ID NO 4
<211> LENGTH: 7
<212> TYPE: PRT
<213> ORGANISM: Homo sapiens

<400> SEQUENCE: 4

Ser Gly Val Lys Ser Ala Phe
1               5

<210> SEQ ID NO 5
<211> LENGTH: 7
<212> TYPE: PRT
<213> ORGANISM: Homo sapiens

<400> SEQUENCE: 5

Gly Val Lys Ser Tyr Asn Glu
1               5

<210> SEQ ID NO 6
```

```
<211> LENGTH: 7
<212> TYPE: PRT
<213> ORGANISM: Homo sapiens

<400> SEQUENCE: 6

Ile Gly Lys Thr Asn Thr Leu
1               5

<210> SEQ ID NO 7
<211> LENGTH: 7
<212> TYPE: PRT
<213> ORGANISM: Homo sapiens

<400> SEQUENCE: 7

Ile Gly Asn Ser Asn Thr Leu
1               5

<210> SEQ ID NO 8
<211> LENGTH: 7
<212> TYPE: PRT
<213> ORGANISM: Homo sapiens

<400> SEQUENCE: 8

Ile Gly Asn Thr Ile Pro Val
1               5

<210> SEQ ID NO 9
<211> LENGTH: 7
<212> TYPE: PRT
<213> ORGANISM: Homo sapiens

<400> SEQUENCE: 9

Leu Tyr Ala Asn Ser Pro Phe
1               5

<210> SEQ ID NO 10
<211> LENGTH: 9
<212> TYPE: PRT
<213> ORGANISM: Homo sapiens

<400> SEQUENCE: 10

Cys Thr Val Arg Thr Ser Ala Asp Cys
1               5

<210> SEQ ID NO 11
<211> LENGTH: 9
<212> TYPE: PRT
<213> ORGANISM: Homo sapiens

<400> SEQUENCE: 11

Cys Asn Trp Gly Asp Arg Ile Leu Cys
1               5

<210> SEQ ID NO 12
<211> LENGTH: 9
<212> TYPE: PRT
<213> ORGANISM: Homo sapiens

<400> SEQUENCE: 12

Cys Asn Trp Gly Lys Pro Ile Lys Cys
1               5

<210> SEQ ID NO 13
<211> LENGTH: 9
<212> TYPE: PRT
```

<213> ORGANISM: Homo sapiens

<400> SEQUENCE: 13

Cys Ser Gly Val Lys Ser Ala Phe Cys
1               5

<210> SEQ ID NO 14
<211> LENGTH: 9
<212> TYPE: PRT
<213> ORGANISM: Homo sapiens

<400> SEQUENCE: 14

Cys Gly Val Lys Ser Tyr Asn Glu Cys
1               5

<210> SEQ ID NO 15
<211> LENGTH: 9
<212> TYPE: PRT
<213> ORGANISM: Homo sapiens

<400> SEQUENCE: 15

Cys Ile Gly Lys Thr Asn Thr Leu Cys
1               5

<210> SEQ ID NO 16
<211> LENGTH: 9
<212> TYPE: PRT
<213> ORGANISM: Homo sapiens

<400> SEQUENCE: 16

Cys Ile Gly Asn Ser Asn Thr Leu Cys
1               5

<210> SEQ ID NO 17
<211> LENGTH: 9
<212> TYPE: PRT
<213> ORGANISM: Homo sapiens

<400> SEQUENCE: 17

Cys Ile Gly Asn Thr Ile Pro Val Cys
1               5

<210> SEQ ID NO 18
<211> LENGTH: 9
<212> TYPE: PRT
<213> ORGANISM: Homo sapiens

<400> SEQUENCE: 18

Cys Leu Tyr Ala Asn Ser Pro Phe Cys
1               5

<210> SEQ ID NO 19
<211> LENGTH: 7
<212> TYPE: PRT
<213> ORGANISM: Homo sapiens

<400> SEQUENCE: 19

Trp Asn Tyr Pro Phe Arg Leu
1               5

<210> SEQ ID NO 20
<211> LENGTH: 7
<212> TYPE: PRT
<213> ORGANISM: Homo sapiens

```
<400> SEQUENCE: 20

Ser Asn Thr Ser Tyr Val Asn
1               5

<210> SEQ ID NO 21
<211> LENGTH: 7
<212> TYPE: PRT
<213> ORGANISM: Homo sapiens

<400> SEQUENCE: 21

Ser Phe Ser Tyr Thr Ser Gly
1               5

<210> SEQ ID NO 22
<211> LENGTH: 7
<212> TYPE: PRT
<213> ORGANISM: Homo sapiens

<400> SEQUENCE: 22

Trp Ser Pro Ala Pro Met Ser
1               5

<210> SEQ ID NO 23
<211> LENGTH: 7
<212> TYPE: PRT
<213> ORGANISM: Homo sapiens

<400> SEQUENCE: 23

Thr Arg Glu His Pro Ala Gln
1               5

<210> SEQ ID NO 24
<211> LENGTH: 7
<212> TYPE: PRT
<213> ORGANISM: Homo sapiens

<400> SEQUENCE: 24

Ala Arg Ile Ile Asp Asn Ala
1               5

<210> SEQ ID NO 25
<211> LENGTH: 9
<212> TYPE: PRT
<213> ORGANISM: Homo sapiens

<400> SEQUENCE: 25

Cys Trp Asn Tyr Pro Phe Arg Leu Cys
1               5

<210> SEQ ID NO 26
<211> LENGTH: 9
<212> TYPE: PRT
<213> ORGANISM: Homo sapiens

<400> SEQUENCE: 26

Cys Ser Asn Thr Ser Tyr Val Asn Cys
1               5

<210> SEQ ID NO 27
<211> LENGTH: 9
<212> TYPE: PRT
<213> ORGANISM: Homo sapiens

<400> SEQUENCE: 27
```

Cys Ser Phe Ser Tyr Thr Ser Gly Cys
1               5

<210> SEQ ID NO 28
<211> LENGTH: 9
<212> TYPE: PRT
<213> ORGANISM: Homo sapiens

<400> SEQUENCE: 28

Cys Trp Ser Pro Ala Pro Met Ser Cys
1               5

<210> SEQ ID NO 29
<211> LENGTH: 9
<212> TYPE: PRT
<213> ORGANISM: Homo sapiens

<400> SEQUENCE: 29

Cys Thr Arg Glu His Pro Ala Gln Cys
1               5

<210> SEQ ID NO 30
<211> LENGTH: 9
<212> TYPE: PRT
<213> ORGANISM: Homo sapiens

<400> SEQUENCE: 30

Cys Ala Arg Ile Ile Asp Asn Ala Cys
1               5

<210> SEQ ID NO 31
<211> LENGTH: 19
<212> TYPE: DNA
<213> ORGANISM: Homo sapiens

<400> SEQUENCE: 31
gcagcccaca gtggagtat                                            19

<210> SEQ ID NO 32
<211> LENGTH: 20
<212> TYPE: DNA
<213> ORGANISM: Homo sapiens

<400> SEQUENCE: 32
ggagcaaggt tgatttcttt                                           20

<210> SEQ ID NO 33
<211> LENGTH: 19
<212> TYPE: DNA
<213> ORGANISM: Homo sapiens

<400> SEQUENCE: 33
gcagcccaca gtggagtat                                            19

<210> SEQ ID NO 34
<211> LENGTH: 20
<212> TYPE: DNA
<213> ORGANISM: Homo sapiens

<400> SEQUENCE: 34
ggagcaaggt tgatttcttt                                           20

<210> SEQ ID NO 35
<211> LENGTH: 20

```
<212> TYPE: DNA
<213> ORGANISM: Homo sapiens

<400> SEQUENCE: 35
acccagaaga ctgtggatgg                                                20

<210> SEQ ID NO 36
<211> LENGTH: 20
<212> TYPE: DNA
<213> ORGANISM: Homo sapiens

<400> SEQUENCE: 36
tctagacggc aggtcaggtc                                                20

<210> SEQ ID NO 37
<211> LENGTH: 20
<212> TYPE: DNA
<213> ORGANISM: Homo sapiens

<400> SEQUENCE: 37
tgcccagaaa atgaaaaagg                                                20

<210> SEQ ID NO 38
<211> LENGTH: 20
<212> TYPE: DNA
<213> ORGANISM: Homo sapiens

<400> SEQUENCE: 38
gtgtatgtgg caatgcgttc                                                20

<210> SEQ ID NO 39
<211> LENGTH: 20
<212> TYPE: DNA
<213> ORGANISM: Homo sapiens

<400> SEQUENCE: 39
acagtggcca cctacaaagg                                                20

<210> SEQ ID NO 40
<211> LENGTH: 20
<212> TYPE: DNA
<213> ORGANISM: Homo sapiens

<400> SEQUENCE: 40
ccgagatggg gttgataatg                                                20

<210> SEQ ID NO 41
<211> LENGTH: 9
<212> TYPE: PRT
<213> ORGANISM: Homo sapiens

<400> SEQUENCE: 41

Thr Val Arg Thr Ser Ala Asp Cys Cys
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Constructs

<400> SEQUENCE: 42

Cys Thr Val Arg Thr Ser Ala Asp
```

```
<210> SEQ ID NO 43
<211> LENGTH: 8
<212> TYPE: PRT
<213> ORGANISM: Artificial Sequence
<220> FEATURE:
<223> OTHER INFORMATION: Synthetic Construct

<400> SEQUENCE: 43

Cys Asn Trp Gly Asp Arg Ile Leu
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic Construct

<400> SEQUENCE: 44

Cys Asn Trp Gly Lys Pro Ile Lys
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic Construct

<400> SEQUENCE: 45

Cys Ser Gly Val Lys Ser Ala Phe
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic Construct

<400> SEQUENCE: 46

Cys Gly Val Lys Ser Tyr Asn Glu
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic Construct

<400> SEQUENCE: 47

Cys Ile Gly Lys Thr Asn Thr Leu
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic Construct

<400> SEQUENCE: 48

Cys Ile Gly Asn Ser Asn Thr Leu
1               5
```

<210> SEQ ID NO 49
<211> LENGTH: 8
<212> TYPE: PRT
<213> ORGANISM: Artificial Sequence
<220> FEATURE:
<223> OTHER INFORMATION: Synthetic Construct

<400> SEQUENCE: 49

Cys Ile Gly Asn Thr Ile Pro Val
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct

<400> SEQUENCE: 50

Cys Leu Tyr Ala Asn Ser Pro Phe
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic Construct

<400> SEQUENCE: 51

Cys Thr Val Arg Thr Ser Ala Asp
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic Construct

<400> SEQUENCE: 52

Cys Asn Trp Gly Asp Arg Ile Leu
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic Construct

<400> SEQUENCE: 53

Cys Asn Trp Gly Lys Pro Ile Lys
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic Construct

<400> SEQUENCE: 54

Cys Ser Gly Val Lys Ser Ala Phe
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic Construct

<400> SEQUENCE: 55

Cys Gly Val Lys Ser Tyr Asn Glu
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic Construct

<400> SEQUENCE: 56

Cys Ile Gly Lys Thr Asn Thr Leu
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic Construct

<400> SEQUENCE: 57

Cys Ile Gly Asn Ser Asn Thr Leu
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic Construct

<400> SEQUENCE: 58

Cys Ile Gly Asn Thr Ile Pro Val
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic Construct

<400> SEQUENCE: 59

Cys Leu Tyr Ala Asn Ser Pro Phe
1               5

MOLECULAR PROBES AND METHODS OF USE

RELATED APPLICATION

This application claims priority from U.S. Provisional Application No. 62/425,805 filed Nov. 23, 2016. This application is also a Continuation-in-Part of U.S. Ser. No. 15/502,160, filed Feb. 6, 2017, which is a National Phase Filing of PCT/US2015/043668, filed Aug. 4, 2015, which claims priority to U.S. Provisional Application Ser. No. 62/032,945, filed Aug. 4, 2014, the subject matter of which is incorporated herein by reference in its entirety.

BACKGROUND

Cancer detection and treatment are hindered by the inability to differentiate between cancer cells and normal cells. Better detection tools for cancer or tumor imaging are needed for earlier diagnosis of cancers. Molecular recognition of tumor cells would facilitate guided surgical resection. In order to improve surgical resection, targeted imaging tools must specifically label tumor cells, not only in the main tumor but also along the edge of the tumor and in the small tumor cell clusters that disperse throughout the body. Targeted imaging tools designed to label molecules that accumulate in the tumor microenvironment may also be advantageous as therapeutic targeting agents, as they can identify both the main tumor cell population and areas with infiltrating cells that contribute to tumor recurrence. The ability to directly target the tumor cell and/or its microenvironment would increase both the specificity and sensitivity of current treatments, therefore reducing non-specific side effects of chemotherapeutics that affect cells throughout the body.

SUMMARY

Embodiments described herein relate to a molecular probe that can be used to detect the location and/or distribution of cancer cells in tissue of a subject, the aggressiveness of cancer in a subject, and/or the efficacy of a cancer therapeutic and/or cancer therapy administered to a subject in need thereof.

In some embodiments, the molecular probe can include the following formula:

P-L-C wherein P is a peptide that includes an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9; C is a contrast agent; and L is a non-peptide linker that covalently links the peptide to the contrast agent. The linker can include a carboxylic acid that forms a carboxamide with an amine of the peptide or a maleimide that forms a thioester with a cysteine residue of the peptide.

In some embodiments, the non-peptide linker is a non-peptide aliphatic or heteroaliphatic linker. The non-peptide linker can include an alkylene dicarboxamide that covalently links the peptide and contrast agent.

In some embodiments, the contrast agent is a magnetic resonance imaging (MRI), positron emission tomography (PET), or single photon emission computed tomography (SPECT) contrast agent.

The MRI, PET, or SPECT contrast agent can include at least one of a metal chelating agent or a metallofullerene.

The metal chelating agent can include, for example, at least one of diethylenetriaminepentaacetate (DTPA) or its derivatives, 1,4,7,10-tetraazadodecanetetraacetate (DOTA) and its derivatives, 1,4,7,10-tetraazadodecane-1,4,7-triacetate (DO3A) and its derivatives, ethylenediaminetetraacetate (EDTA) and its derivatives, 1,4,7,10-tetraazacyclotridecanetetraacetic acid (TRITA) and its derivatives, 1,4,8,11-tetraazacyclotetradecane-1,4,8,11-tetraacetic acid (TETA) and its derivatives, 1,4,7,10-tetraazadodecanetetramethylacetate (DOTMA) and its derivatives, 1,4,7,10-tetraazadodecane-1,4,7-trimethylacetate (DO3MA) and its derivatives, N,N',N'',N'''-tetraphosphonatomethyl-1,4,7,10-tetraazacyclododecane (DOTP) and its derivatives, 1,4,7,10-tetraazacyclododecane-1,4,7,10-tetrakis(methylene methylphosphonic acid) (DOTMP) and its derivatives, 1,4,7,10-tetraazacyclododecane-1,4,7,10-tetrakis(methylene phenylphosphonic acid) (DOTPP) and its derivatives, or N,N'-ethylenedi-L-cysteine and its derivatives. The metallofullerene can include, for example, Gd3N@C80.

In some embodiments, the molecular probe can having the formula:

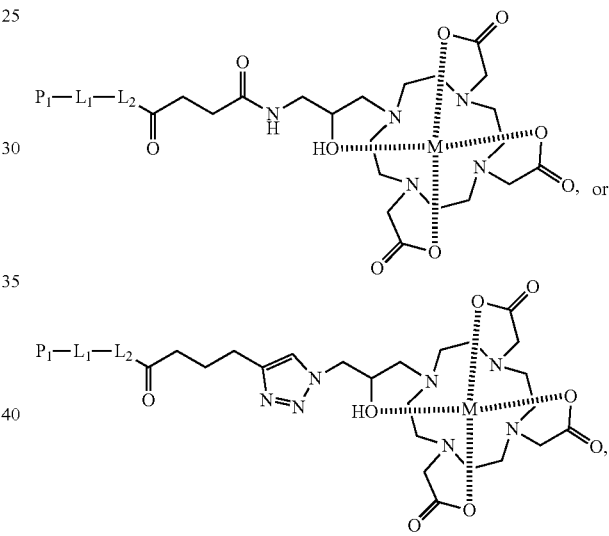

wherein:

$P_1$ is a peptide that includes an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9;

$L_1$ is an optional spacer, $L_2$ is an amino group of the peptide $P_1$ or the spacer, and M is a metal selected from the group consisting of $Gd^{+3}$, $Eu^{+3}$, $Tm^{+3}$, $Dy^{+3}$, $Yb^{+3}$, $Mn^{+2}$, $Fe^{+3}$, $^{55}Co$, $^{64}Cu$, $^{67}Cu$, $^{47}Sc$, $^{66}Ga$, $^{68}Ga$, $^{90}Y$, $^{97}Ru$, $^{99m}Tc$, $^{111}h$, $^{109}Pd$, $^{153}Sm$, $^{177}Lu$, $^{186}Re$, and $^{133}Re$; or salts thereof.

In some embodiments, can include at least one of a polyalkyleneoxide, polyvinyl alcohol, polyethylene glycol (PEG), polypropylene glycol (PPG), co-poly (ethylene/propylene) glycol, polyoxyethylene (POE), polyurethane, polyphosphazene, polysaccharides, dextran, polyvinylpyrrolidones, polyvinyl ethyl ether, polyacryl amide, polyacrylate, or polycyanoacrylates.

In other embodiments, the probe can have the formula:

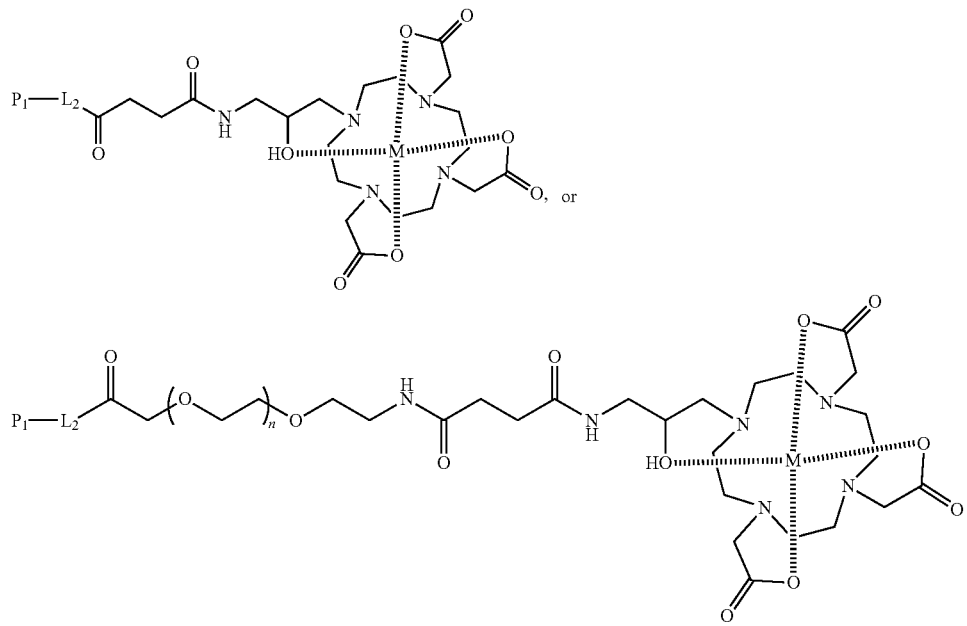

wherein:
P₁ is a peptide having an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9;

L₂ is an amino group of the peptide P₁, and

M is a metal selected from the group consisting of $Gd^{+3}$, $Eu^{+3}$, $Tm^{+3}$, $Dy^{+3}$, $Yb^{+3}$, $Mn^{+2}$, $Fe^{+3}$, $^{55}Co$, $^{64}Cu$, $^{67}Cu$, $^{47}Sc$, $^{66}Ga$, $^{68}Ga$, $^{90}Y$, $^{97}Ru$, $^{99m}Tc$, $^{111}h$, $^{109}Pd$, $^{153}Sm$, $^{177}Lu$, $^{186}Re$, and $^{188}Re$, and n is an integer from 0 to 100; or salts thereof.

In still other embodiments, the molecular probe can be administered systematically to the subject to detect the distribution and/or location of cancer in the subject as well as the cancer aggressiveness. The cancer can include, for example, at least one of breast cancer, liver cancer, stomach cancer, colon cancer, pancreatic cancer, ovarian cancer, lung cancer, kidney cancer, prostate cancer, testicular cancer, glioblastoma, sarcoma, bone cancer, brain cancer, head and neck cancers, or skin cancer.

BRIEF DESCRIPTION OF THE DRAWINGS

FIGS. 1(A-D) illustrate: (A) A schematic drawing showing the construction of EDB expressing plasmid. DNA encoding EDB fragment was inserted under the control of 17 promoter, with infusion of 10×His tags on the N-terminal. Lac operator (lacO) allows control of EDB expression with IPTG induction. B) SDS-PAGE of lysates from EDB expressing E. coli. Lanes were labeled as follows: M: protein ladder; 1. E. coli cell lysate before induction with IPTG; 2, 1.5 h post induction; 3, 3 h post induction; 4, purified EDB solution from lysate acquired 3 hours after induction). C) MALDI-TOF mass spectrum of ZD2 peptide with the sequence of CTVRTSADC, [m/z M+]=954.23 (observed), 954.39 (calculated). D) Peptide ELISA for quantification of binding affinity between ZD2 and EDB protein.

FIGS. 2(A-D) illustrate: A) Morphology of PC3 cells with and without TGFβ1 induction. Images were taken by phage-contrast microscopy at 10× and 40× (insert). B) RT-PCR analysis of EDA, EDB, E-Cad, and N-Cad expression in cells after TGFβ1 induction relative to those without induction. C) Representative images of ZD2-Cy5 binding to cell periphery when TGFβ1 inducted PC3 cells were growing in growth medium containing 0.25 μM of ZD2-Cy5. Non-inducted cells were used as a control. Images were taken with confocal fluorescence microscopy at 40× and 100× (insert). D) Comparison of live cell staining between ZD2-Cy5 and free Cy5 dye (100× magnification).

FIGS. 3(A-D) illustrate: A) Representative fluorescence images of PC3 bearing mouse at 1.5 h after intravenous injection of 10 nmol ZD2-Cy5 or non-specific control CERAK-Cy5 (Cy5, left panel; GFP; right panel; white arrows point to tumors). B) Fluorescence intensity ratio between tumor and normal tissues (T/N ratio) as a function of time from mice injected with ZD2-Cy5 or CERAK-Cy5 (N=3). C) Representative fluorescence images of organs harvested from PC3-GFP tumor bearing mouse 5 h post-injection with ZD2-Cy5 or CERAK-Cy5. Cy5 channel (left). GFP channel (middle), and bright field images (right) were shown. Organs are represented with numbers: 1, tumor; 2, liver; 3, muscle; 4, heart; 5, brain; 6, lung; 7, spleen. D) Western blot analysis of tumor, liver, and lung lysates harvested from PC3 tumor bearing mouse.

FIGS. 4(A-C) illustrate A) Representative fluorescence images of tumor sections from PC3 tumor model injected with ZD2-Cy5 or CERAK-Cy5. B) Representative fluorescence images of the liver and lung sections from the same mice. Scale bar: 20 μm. C) Correlation of ZD2 distribution with EDB-FN (BC-1) distribution and blood vessel distribution (anti-CD31) in PC3 tumor sections. Scale bar: 20 μm.

FIGS. 5(A-E) illustrate: A) H&E staining, immunofluorescence staining with BC-1, and ZD2-Cy5 staining of human prostate BPH section and prostate tumor sections of GS7 (3+4) and GS9 (4+5). Scale bar: 100 μm. B) Representative Cy5 histograms indicate distribution of Cy5 pixel intensities in images shown in A. Labeled portion of the histograms is the percent pixel counts of Cy5 pixel value ranging from 50 to 255 (upper panel). Analysis of histogram distribution in each prostate section of different Gleason scores was also shown. Box chart represents distribution of data acquired in the histogram analysis (lower panel). C) The image of a region of GS7 prostate that contains both high staining glandular areas and low staining areas, showing the relationship between staining level and gland morphology. Low staining glands were labeled with white arrows and high staining glands are labeled with arrowheads. Image was acquired with Olympus Virtual Slide Microscopy system. Scale bar: 40 μm. D) Western blot analysis of prostate lysates from normal or cancerous prostate tissues GS7 (3+4). EDB-FN expression was determined by BC-1, β-actin expression was used as loading control. Column graph indicates difference in levels of expression of EDB-FN indicated by western blot (n=3; ***, p<0.001). E) Competitive staining with BC-1 (green) and ZD2 (red). BC-1 binding blocked the binding of ZD2-Cy5. Scale bar: 100 μm.

FIGS. 6(A-B) illustrate: A) A graph showing relative mRNA expression of EDB FN in 4T1 cell line with TGFβ compared with non-induced cells (control). B) Western blot analysis of EDB FN expression in tumor tissues collected from different organs. β-actin was used as a loading control.

FIGS. 9(A-C) illustrate: A) Bioluminescent images of a representative mouse developed metastatic tumors in lymph nodes, adrenal glands, and chest and corresponding tumors identified in MRI images. B) Colocalization of MRI and BLI to verify the targeting of l-zd2-Gd(HP-DO3A) to metastatic tumors on different organs. C. MRI of metastatic tumor of CERAK-Gd(HP-DO3A).

FIGS. 16(A-B) illustrate in vitro complexation stability and transmetallation analysis of ZD2-Gd(HP-DO3A). A) relative Gd content of ZD2-Gd(HP-DO3A) assayed during 200-min incubation of the agent in phosphate buffer saline (PBS) with and without Cu$^{2+}$, Ca$^{2+}$, or Zn$^{2+}$ ions. No decrease in Gd content is observed, demonstrating high chelation stability. B) In vitro transmetallation analysis of MultiHance, OmniScan, ProHance (abbreviated as Pro.), and ZD2-Gd(HP-DO3A) (abbreviated as ZD2) in mouse senim.

FIGS. 17(A-G) illustrate upregulated EDB-FN expression is a promising biomarker for high-risk prostate cancer. A) comparison of the relative mRNA expression of prostate cancer biomarkers, including EDB-FN (EDB), Vimentin, E-Cadherin (E-Cad), N-Cadherin (N-Cad), epidermal growth factor receptor (EGFR), and prostate-specific membrane antigen (PSMA) between PC3 and LNCaP cells (n=3, unpaired two-tailed t-test. *: P<0.05, : P<0.01, *: P<0.001). All gene expression was normalized to β-actin mRNA levels. B) western blot analysis of EDB-FN expression in PC3 and LNCaP tumors. Actin expression was used as a loading control. C) representative phase contrast images of LNCaP and PC3 cells grown in 3D matrigel. Scale bar: 40 μm. D) representative fluorescence images of 3D cultures of LNCaP and PC3 cells incubated with 250 nM ZD2-Cy5.5, using confocal microscopy. E) ex vivo fluorescent Cy5.5 and bright field (BF) images of tumors and organs from PC3 and LNCaP mouse models, 3 h post-injection of 10 nmol ZD2-Cy5.5. Numbers denote: 1, lung; 2, tumor, 3, spleen; 4, muscle; 5, brain; 6, heart; 7, kidney; 8, liver. F) confocal fluorescence microscopy images of PC3 and LNCaP tumor sections stained with ZD2-Cy5.5 and anti-EDB-FN antibody. Colors: blue, DAPI; red, ZD2-Cy5.5; yellow, EDB-FN. Overlay: addition of DAPI, ZD2-Cy5.5, and EDB-FN channels. Scale bar: 20 μm. G) immunohistochemical (IHC) staining for EDB-FN and H&E staining on PC3 and LNCaP tumor sections. The brown color in THC staining indicates EDB-FN distribution only in PC3 but not in the LNCaP sections. Scale bar: 20 μm.

FIGS. 18(A-C) illustrate the EDB-FN targeting contrast agent, ZD2-Gd(HP-DO3A), is capable of differentiating between PC3 and LNCaP tumors in T1-weighted MRI. A) plot of 1/T1 value versus concentration of ZD2-Gd(HP-DO3A) for calculating r1 relaxivity in PBS at 7T. Inset: T1 color-coded maps of phantoms containing ZD2-Gd(HP-DO3A) solution at different concentrations. Numbers close to each phantom denote: 1, 50 µM; 2, 25 µM; 3, 12.5 µM; 4, 6.25 µM; 5, 3.12 µM. B) Axial MRI images of PC3 and LNCaP tumor models at the indicated tumor positions acquired with a T1-weighted sequence. Images of mice at pre-contrast (abbreviated as pre) and at 10 min, 20 min, and 30 min post-injection are shown. The names of the contrast agents are abbreviated as: ZD2, ZD2-Gd(HP-DO3A); Pro., ProHance. Competitive: injection of 0.1 mmol/kg ZD2-Gd (HP-DO3A) mixed with 0.5 mmol/kg ZD2 peptide in mice with PC3 tumors. C) change in contrast-to-noise ratio of tumors in the experiments shown in B. Data represent the mean±s.e.m. of 5 mice in all experimental groups except for the competitive group (n=3) (unpaired two-tailed t-test: P<0.05 for comparison of ZD2-PC3 vs. all other groups at 10 min, 20 min and 30 min). Legends: ZD2-PC3, PC3 tumor model injected with ZD2-Gd(HP-DO3A); ZD2-LNCaP, LNCaP tumor model injected with ZD2-Gd(HP-DO3A); Pro.-PC3, PC3 tumor model injected with ProHance; Pro.-LNCaP, LNCaP tumor model injected with ProHance.

FIGS. 19(A-B) illustrate contrast enhanced MRI with CREKA-Gd(HP-DO3A) in the PC3 and LNCaP tumors. A, axial images of PC3 and LNCaP tumor locations. B, quantification of the change in CNR in the PC3 and LNCaP tumors up to 30 min after CREKA-Gd(HP-DO3A) injection. No significant difference is seen between the two groups.

FIGS. 20(A-C) illustrate T1 maps and accumulation of ZD2-Gd(HP-DO3A) validate its specific binding in PC3 tumors. A) T1 and $\Delta R1$ maps showing the tumor T1 and $\Delta R1$ values in PC3 or LNCaP tumor models injected with ZD2-Gd(HP-DO3A) (abbreviated as ZD2) or ProHance (abbreviated as Pro.) at pre-contrast (pre) or 30 min post-injection. Images are displayed as overlay of tumor color-coded maps with axial T1-weighted images. B) quantification of average $\Delta R1$ after contrast injection in the groups shown in A (n=4; *, P<0.05, **, P<0.01). C) comparison of contrast agent accumulation in the tumors, as measured by ICP-OES at 30 min after contrast agent injection (unpaired two-tailed t-test: n=4; *, P<0.05; NS: not significant).

FIGS. 22(A-D) illustrate electrostatic surface of EDB fragment and 3D stick molecular models of linear peptides GVK (a), IGK (b), SGV (c), and ZD2 (d) fitted to the protein. For the surface of EDB, blue indicates positive charged residues, red represents negative areas and white are neutral regions. Active residues for docking calculations are numbered.

FIGS. 29(A-C) illustrates contrast to noise ratio of kidney (a), liver (b) and tumor (c). (n=5) Error bars represent±standard deviation.

FIGS. 30(A-B) illustrate an EDB-FN-targeting gadofullerene for molecular MRI of breast cancer. A) Schematic of synthesis of ZD2-Gd$_3$N@C80. Cyan, Gd; blue, nitrogen; red, oxygen; grey, hydrogen. B) Illustration of tumour targeting with ZD2-Gd$_3$N@C80 for detection and characterization of breast cancer in mouse models. MCF-7 and MDA-MB-231 cells were used to obtain low-risk and high-risk breast cancer xenografts, respectively. Intravenous injection of the EDB-FN-targeting agent, ZD2-Gd$_3$N@C80, results in different binding levels, corresponding to the EDB-FN expression and tumour aggressiveness, for tumour detection and characterization with molecular MRI.

FIGS. 31(A-E) illustrate a characterization of ZD2-Gd$_3$N@C80. A) Fourier transform infrared spectroscopy (FTIR) of ZD2-Gd$_3$N@C80. Inset: photograph of ZD2-Gd$_3$N@C80 solution (0.083 mM). Plots of $1/T_1$ and $1/T_2$ versus contrast agent concentrations for calculation of $r_1$ and $r_2$ relaxivities of B) hydroxylated Gd$_3$N@C80 ($r_1$=171.3 mM$^{-1}$ s$^{-1}$; $r_2$=295.5 mM$^{-1}$ s$^{-1}$) and C) ZD2-Gd$_3$N@C80 ($r_1$=223.8 mM$^{-1}$ s$^{-1}$) and $r_2$=344.7 mM$^{-1}$s$^{-1}$) at 1.5 Tesla. D) TEM images (Scale bar: 5 nm) and E) DLS size distribution of ZD2-Gd$_3$N@C80 (average radius: 1.40 nm; polydispersity: 132%).

FIGS. 32(A-F) illustrate EDB-FN overexpression is a signature of aggressive breast cancer. A) RT-PCR analysis of EDB-FN mRNA levels in MCF-7 and MDA-MB-231 cells, showing increased EDB-FN expression in MDA-MB-231 cells (Data are presented as mean±s.e.m. n=3; two-tailed t-test: P<0.05). The data are presented as ratios to the mRNA level of MCF-7. The mRNA level of β-actin was used for normalization. B) Western blot analysis of EDB-FN expression in MCF-7 and MDA-MB-231 tumours. β-actin was used as a loading control. C) Representative fluorescence images of ZD2-Cy5.5 (red) binding, bright field images of 3D culture of MCF-7 and MDA-MB-231 cells, and the overlay of fluorescence images with bright fled images. Scale bar: 50 µm. D) Ex vivo fluorescence images of tumour and organs collected from mice bearing MCF-7 and MDA-MB-231 tumours at 3 h after injection of 10 nmol ZD2-Cy5.5. Numbers in the images indicate the following tissues: 1, tumour, 2, muscle; 3, spleen; 4, liver, 5, brain; 6, heart; 7, kidney; 8, lung. E) Analysis of EDB-FN expression and ZD2-Cy5.5 binding in MCF-7 and MDA-MB-231 tumour sections. DAPI was used for staining nuclei. Scale bar: 25 µm. F) H&E staining showing the morphology of MCF-7 and MDA-MB-231 tumour sections. Scale bar: 50 µm. Inset: enlarged images of the tumour sections (Scale bar: 10 µm).

FIGS. 33(A-C) illustrate a contrast enhanced MRI with ZD2-Gd$_3$N@C80 of MDA-MB-231 and MCF-7 tumours in mice. A) Representative axial T$_1$-weighted 2D spin-echo MRI images of MDA-MB-231 and MCF-7 tumours in mice. Images were acquired before and at 10, 20, and 30 min after injection of ZD2-Gd$_3$N@C80 and hydroxylated Gd$_3$N@C80 at a dose of 1.67 µmol, or a mixture of 25 µmol/kg free ZD2 and 1.67 µmol ZD2-Gd$_3$N@C80 (competitive group). Tumour locations are indicated by white arrow heads. B) Analysis of percentage increase of tumour contrast-to-noise ratio (CNR) from images acquired in groups indicated in (A) (Data are presented as mean±s.e.m. n=4 for MDA-MB-231 tumours and n=3 for MCF-7 tumours. *: $P<0.05$ for comparison of the increased CNR ratio of ZD2-Gd$_3$N@C80 in MDA-MB-231 group with that in all the other groups). C) Gd biodistribution at 1 week after injection of ZD2-Gd$_3$N@C80 or hydroxylated Gd$_3$N@C80 in MDA-MB-231 tumour models. There was no statistical difference between retention of the contrast agents in all the tested tissues (Data are presented as mean±s.e.m. n=3).

FIGS. 34(A-D) illustrate a contrast enhanced MRI with ZD2-Gd$_3$N@C80 of other breast tumors in mice. Representative axial MR images (7 Tesla) and tumour CNR analysis of mice bearing Hs578T and ZR-75-1 (A and B), BT549 and T47D (C and D) xenografts in flanks. Images were acquired at pre and 30 min post-injection of 20 µmol Gd/kg ZD2-Gd$_3$N@C80 (Data are presented as mean±s.e.m. n=3, two-tailed t-test; *, $P<0.05$). Tumour locations are indicated with white arrows.

DETAILED DESCRIPTION

Figure 7A:
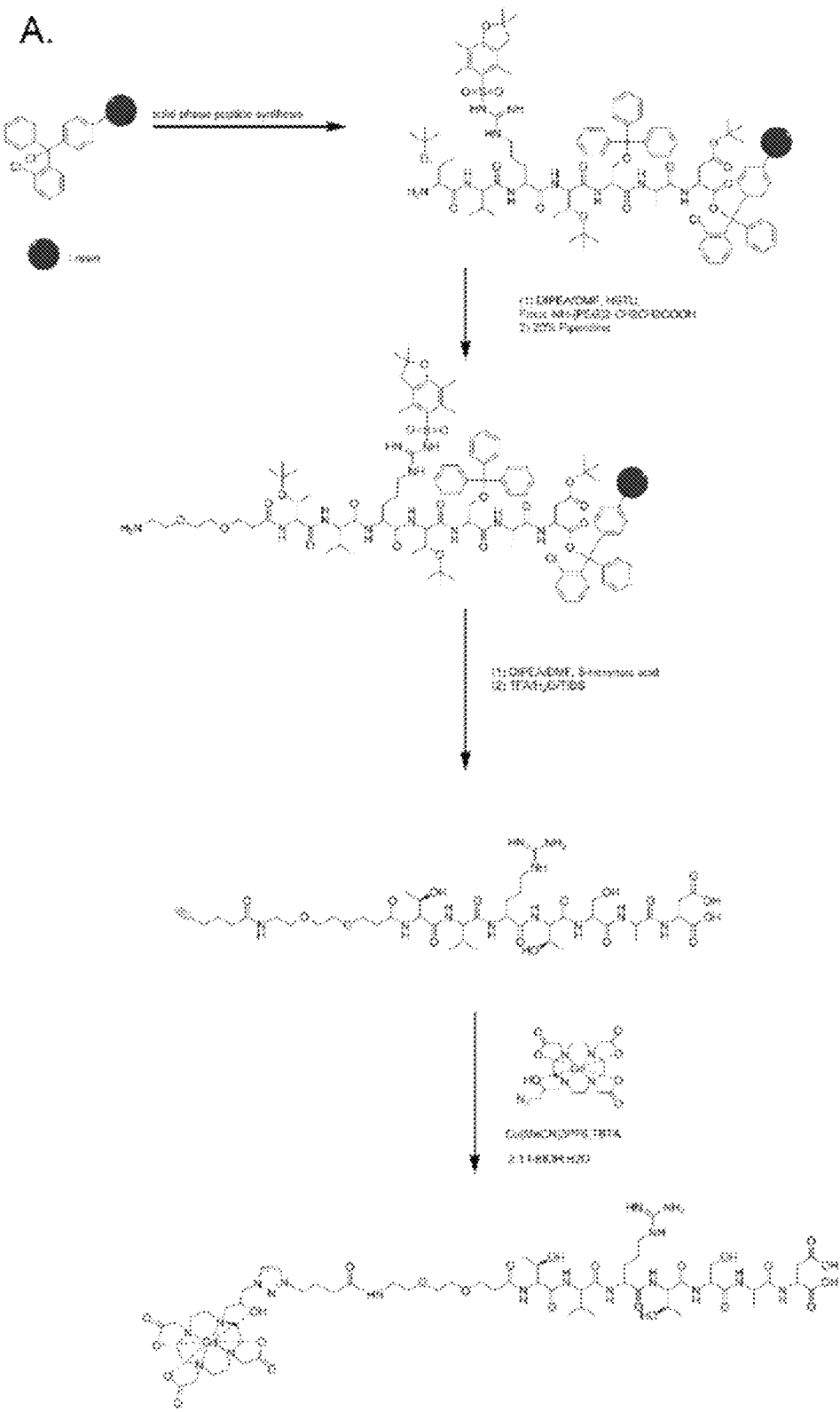
FIGS. 7(A-C) illustrate: A) A synthesis method of l-ZD2-Gd(HP-DO3A). B) Maldi-Tof mass spectrum of l-ZD2-Gd(HP-DO3A). C) Measurement of relaxivities ($T_1$, and $T_2$) of l-ZD2-Gd(HP-DO3A).

Methods involving conventional molecular biology techniques are described herein. Such techniques are generally known in the art and are described in detail in methodology treatises, such as *Current Protocols in Molecular Biology*, ed. Ausubel el al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The term "agent" is used herein to denote a chemical compound, a mixture of chemical compounds, a biological macromolecule, or an extract made from biological materials.

The terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

The terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

The term "chimeric protein" or "fusion protein" is a fusion of a first amino acid sequence encoding a polypeptide with a second amino acid sequence defining a domain (e.g. polypeptide portion) foreign to and not substantially homologous with any domain of the first polypeptide. A chimeric protein may present a foreign domain, which is found (albeit in a different protein) in an organism, which also expresses the first protein, or it may be an "interspecies", "intergenic", etc. fusion of protein structures expressed by different kinds of organisms.

The term "isolated" as used herein with respect to nucleic acids, such as DNA or RNA, or amino acids refers to molecules separated from other DNAs, or RNAs, polypeptides or protein respectively, which are present in the natural source of the macromolecule. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" or "isolated peptide" is meant to include nucleic acid fragments or peptide fragments, which are not naturally occurring as fragments and would not be found in the natural state.

The term "mutant" refers to any change in the genetic material of an organism, in particular a change (i.e., deletion, substitution, addition, or alteration) in a wild type polynucleotide sequence or any change in a wild type protein. The term "variant" is used interchangeably with "mutant". Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

The term "nucleic acid" refers to polynucleotides, such as deoxyribonucleic acid (DNA), and, where appropriate, ribonucleic acid (RNA). The term should also be understood to include, as equivalents, analogs of RNA or DNA made from nucleotide analogs, and, as applicable to the embodiment being described, single (sense or antisense) and double-stranded polynucleotides.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The terms "patient", "subject", "mammalian host," and the like are used interchangeably herein, and refer to mammals, including human and veterinary subjects.

The terms "peptide(s)", "protein(s)" and "polypeptide(s)" are used interchangeably herein. As used herein, "polypeptide" refers to any peptide or protein comprising two or more amino acids joined to each other by peptide bonds or modified peptide bonds (i.e., peptide isomers). "Polypeptide(s)" refers to both short chains, commonly referred as peptides, oligopeptides or oligomers, and to longer chains generally referred to as proteins.

The terms "polynucleotide sequence" and "nucleotide sequence" are also used interchangeably herein.

"Recombinant," as used herein, means that a protein is derived from a prokaryotic or eukaryotic expression system.

The phrases "systemic administration," "administered systemically," "peripheral administration" and "administered peripherally" as used herein mean the administration of a compound, agent or other material other than directly into a specific tissue, organ, or region of the subject being treated (e.g., brain), such that it enters the animal's system and, thus, is subject to metabolism and other like processes, for example, subcutaneous administration.

The term "wild type" refers to the naturally-occurring polynucleotide sequence encoding a protein, or a portion thereof, or protein sequence, or portion thereof, respectively, as it normally exists in vivo.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

Embodiments described herein relate to molecular probes for use in detecting, monitoring, and/or imaging cancer cell distribution and/or location and/or cancer cell metastasis, migration, and/or invasion in a subject, detecting and/or monitoring cancer cell aggressiveness and/or malignancy in a subject, and/or determining and/or monitoring the efficacy of a cancer therapeutic and/or cancer therapy administered to a subject in need thereof.

The molecular probes described herein include targeting peptides with a peptide sequence that specifically binds to and/or complexes with oncofetal fibronectin (onfFN) isoforms, extradomain-B fibronectin (EDB-FN) or extradomain-A (EDA-FN) fibronectin. Cancer, and particularly, malignant cancer has a unique tumor microenvironment that facilitates cancer cell survival, proliferation, and metastasis. The presence of onfFN has been shown in various human cancer types, including prostate and breast cancer. High expression of onfFN, EDB-FN and/or EDA-FN, inversely correlated with cancer aggressiveness and patient survival. It was found that contrast agents or molecular probes that include target peptides, which specifically bind to EDB-FN and/or EDB-FN, can be used for detecting, monitoring, and/or imaging cancer cells in tissue of a subject as well as to determine cancer cell aggressiveness, malignancy, metastasis, migration, dispersal, and/or invasion.

Molecular probes including the targeting peptides can be administered systemically to a subject, such as by intravenous or parenteral administration, and readily target the extracellular matrix proteins EDB-FN and/or EDA-FN to define cancer cell location, distribution, and/or aggressiveness as well as tumor cell margins in the subject.

In some embodiments, the molecular probe can include the following formula:

P-L-C wherein P is a targeting peptide C is a contrast agent; and L is a non-peptide linker that covalently links the peptide to the contrast agent. The linker can include a carboxylic acid that forms a carboxamide with an amine of the peptide or a maeimide that forms a thioester bond with a cysteine residue of the peptide.

In some embodiments, the targeting peptide can specifically bind to EDB-FN. Targeting peptides that specifically bind EDB-FN can include linear peptides having the amino acid sequences of TVRTSAD (SEQ ID NO: 1), NWGDRIL (SEQ ID NO: 2), NWGKPIK (SEQ ID NO: 3), SGVKSAF (SEQ ID NO: 4), GVKSYNE (SEQ ID NO: 5), IGKTNTL (SEQ ID NO: 6), IGNSNTL (SEQ ID NO: 7), IGNTIPV (SEQ ID NO: 8), and LYANSPF (SEQ ID NO: 9), cyclic peptides having the amino acid sequences of CTVRTSADC (SEQ ID NO: 10), CNWGDRILC (SEQ ID NO: 11), CNWGKPIKC (SEQ ID NO: 12), CSGVKSAFC (SEQ ID NO: 13), CGVKSYNEC (SEQ ID NO: 14), CIGKTNTLC (SEQ ID NO: 15), CIGNSNTLC (SEQ ID NO: 16), CIGNTIPVC (SEQ ID NO: 17), or CLYANSPFC (SEQ ID NO:

18), or linear peptides with cysteine linkers CTVRTSAD (SEQ ID NO: 42), CNWGDRIL (SEQ ID NO: 43), CNWGKPIK (SEQ ID NO: 44), CSGVKSAF (SEQ ID NO: 45), CGVKSYNE (SEQ ID NO: 46), CIGKTNTL (SEQ ID NO: 47), CIGNSNTL (SEQ ID NO: 48), CIGNTIPV (SEQ ID NO: 49), and CLYANSPF (SEQ ID NO: 50). In other embodiments, the targeting peptide can specifically bind to EDA-FN. Targeting peptides that specifically bind EDA-FN can include linear peptides having the amino acid sequences of WNYPFRL (SEQ ID NO: 19), SNTSYVN (SEQ ID NO: 20), SFSYTSG (SEQ ID NO: 21), WSPAPMS (SEQ ID NO: 22), TREHPAQ (SEQ ID NO: 23), or ARIIDNA (SEQ ID NO: 24), cyclic peptides having the amino acid sequences of CWNYPFRLC (SEQ ID NO: 25), CSNTSYVNC (SEQ ID NO: 26), CSFSYTSGC (SEQ ID NO: 27). CWSPAPMSC (SEQ ID NO: 28). CTREHPAQC (SEQ ID NO: 29), or CARHDNAC (SEQ ID NO: 30), or linear peptides with cysteine linkers CTVRTSAD (SEQ ID NO: 51), CNWGDRTL (SEQ ID NO: 52), CNWGKPTK (SEQ ID NO: 53), CSGVKSAF (SEQ ID NO: 54), CGVKSYNE (SEQ ID NO: 55), CIGKTNTL (SEQ ID NO: 56), CIGNSNTL (SEQ ID NO: 57), CIGNTIPV (SEQ ID NO: 58), and CLYANSPF (SEQ ID NO: 59).

The targeting peptides can be subject to various changes, substitutions, insertions, and deletions where such changes provide for certain advantages in its use. In this regard, targeting peptides that bind to and/or complex with EDB-FN and/or EDA-FN can be substantially homologous with, rather than be identical to, the sequence of a recited peptide where one or more changes are made and it retains the ability to function as specifically binding to and/or complexing with EDB-FN and/or EDA-FN.

The targeting peptides can be in any of a variety of forms of polypeptide derivatives, that include amides, conjugates with proteins, cyclized polypeptides, polymerized polypeptides, analogs, fragments, chemically modified polypeptides, and the like derivatives.

The term "analog" includes any peptide having an amino acid residue sequence substantially identical to a sequence specifically shown herein in which one or more residues have been conservatively substituted with a functionally similar residue and that specifically binds to and/or complexes with EDB-FN and/or EDA-FN as described herein. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such peptide displays the requisite binding activity.

"Chemical derivative" refers to a subject peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-benzylhistidine. Also included as chemical derivatives are those polypeptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Peptides described herein also include any peptide having one or more additions and/or deletions or residues relative to the sequence of a peptide whose sequence is shown herein, so long as the requisite binding specificity or activity is maintained.

The term "fragment" refers to any subject peptide having an amino acid residue sequence shorter than that of a polypeptide whose amino acid residue sequence is shown herein.

The targeting peptides can be synthesized by any of the techniques that are known to those skilled in the polypeptide art, including recombinant DNA techniques. Synthetic chemistry techniques, such as a solid-phase Merrifield-type synthesis, can be used for reasons of purity, antigenic specificity, freedom from undesired side products, ease of production and the like. A summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer. "Hormonal Proteins and Peptides", Vol. 2, p. 46, Academic Press (New York), 1983; Merrifield, Adv. Enzymol., 32:221-96, 1969; Fields et al., int. J. Peptide Protein Res., 35:161-214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry". Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid can be attached to an inert solid support through its unprotected carboxyl or amino group. The protecting group of the amino or carboxyl group can then be selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group can then be removed from this newly added amino acid residue, and the next amino acid (suitably protected) is then added, and so forth. After all the desired amino acids have been linked in the proper sequence, any remaining terminal and side group protecting groups (and solid support) can be removed sequentially or concurrently, to afford the final linear polypeptide.

Furthermore, the targeting peptides described herein can be used as a starting point to develop higher affinity small molecules, peptides, antibodies, and/or antibody fragments with similar ligand binding capabilities. The development and screening of small molecules from pharmacophores of the peptides using, for example, in silico screening, can be readily performed, and the binding affinity of such identified molecules can be readily screened against targeting peptides using assays described herein to select small molecule agents.

Additional residues may also be added at either terminus of a peptide for the purpose of providing a "linker" by which the peptides can be conveniently linked and/or affixed to other polypeptides, proteins, detectable moieties, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. In addition, a subject targeting peptide agent can differ by the sequence being modified by terminal-NH$_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the non-peptide linker is a non-peptide aliphatic or heteroaliphatic linker. The non-peptide linker can include an alkylene dicarboxamide that covalently links the peptide and contrast agent.

In some embodiments, the non-peptide linker can include a first portion that is about 1 to about 10 atoms in lengths and second portion that acts as a spacer. The portion of the linker that acts a spacer can include a non-peptide polymer that includes but is not limited to a polyalkyleneoxide, polyvinyl alcohol, polyethylene glycol (PEG), polypropylene glycol (PPG), co-poly (ethylene/propylene) glycol, polyoxyethylene (POE), polyurethane, polyphosphazene, polysaccharides, dextran, polyvinylpyrrolidones, polyvinyl ethyl ether, polyacryl amide, polyacrylate, polycyanoacrylates, lipid polymers, chitins, hyaluronic acid, and heparin. For more detailed descriptions of spacers for non-peptide linkers, see, for example, WO/2006/107124, which is incorporated by reference herein. Typically such linkers will have a range of molecular weight of from about 1 kDa to 50 kDa, depending upon a particular linker. For example, a typical PEG has a molecular weight of about 1 to 5 kDa, and polyethylene glycol has a molecular weight of about 5 kDa to 50 kDa, and more preferably about 10 kDa to 40 kDa.

The contrast agent is directly conjugated to the targeting peptide with the linker. The role of the contrast agent is to facilitate the detection step of a detection or diagnostic method by allowing visualization of the complex formed by binding of a molecular probe comprising a targeting peptide to EDB-FN and/or EDA-FN. The contrast agent can be selected such that it generates a signal, which can be measured and whose intensity is related (preferably proportional) to the amount of the molecular probe bound to the tissue being analyzed.

In certain embodiments, the contrast agent includes a chelating agent and a metal ion. The chelating agent generally possesses one or more groups capable of forming a covalent bond with the linker. A number of different chelating agents known in the art can be used herein. In one aspect, the chelating agent comprises an acyclic or cyclic compound comprising at least one heteroatom (e.g., oxygen, nitrogen, sulfur, phosphorous) that has lone-pair electrons capable of coordinating with the imaging agent. An example of an acyclic chelating agent includes ethylenediamine. Examples of cyclic chelating agents include diethylenetriaminepentaacetate (DTPA) or its derivatives, 1,4,7,10-tetraazadodecanetetraacetate (DOTA) and its derivatives, 1,4,7,10-tetraazadodecane-1,4,7-triacetate (DO3A) and its derivatives (e.g., HP-DO3A), ethylenediaminetetraacetate (EDTA) and its derivatives, 1,4,7,10-tetraazacyclotridecanetetraacetic acid (TRITA) and its derivatives, 1,4,8,11-tetraazacyclotetradecane-1,4,8,11-tetraacetic acid (TETA) and its derivatives, 1,4,7,10-tetraazadodecanetetramethylacetate (DOTMA) and its derivatives, 1,4,7,10-tetraazadodecane-1,4,7-trimethylacetate (DO3MA) and its derivatives, N,N',N'',N'''-tetraphosphonatomethyl-1,4,7,10-tetraazacyclododecane (DOTP) and its derivatives, 1,4,7,10-tetraazacyclododecane-1,4,7,10-tetrakis(methylene methylphosphonic acid) (DOTMP) and its derivatives, 1,4,7,10-tetraaracyclododecane-1,4,7,10-tetrakis(methylene phenylphosphonic acid) (DOTPP) and its derivatives, or N,N'-ethylenedi-L-cysteine or its derivatives. The term "derivative" is defined herein as the corresponding salt and ester thereof of the chelating agent.

The selection of the metal ion can vary depending upon the detection technique (e.g., MRI, PET, etc.). Metal ions useful in magnetic resonance imaging can include $Gd^{+3}$, $Eu^{+3}$, $Tm^{+3}$, $Dy^{+3}$, $Yb^{+3}$, $Mn^{+2}$, or $Fe^{+3}$ ions. Metal ions useful in PET and SPECT imaging can include $^{55}Co$, $^{64}Cu$, $^{67}Cu$, $^{47}Sc$, $^{66}Ga$, $^{68}Ga$, $^{90}Y$, $^{97}Ru$, $^{99}mTc$, $^{111}h$, $^{109}Pd$, $^{153}Sm$, $^{177}Lu$, $^{186}Re$, or $^{188}Re$.

In other embodiments, the contrast agent can include a metallofullerene, such as Gd3N@C80.

In some embodiments, the molecular probe can have the formula:
wherein:
$P_1$ is a peptide including an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9;
$L_1$ is an optional spacer,
$L_2$ is an amino group of the peptide $P_1$ or the spacer, and
M is a metal selected from the group consisting of $Gd^{+3}$, $Eu^{43}$, $Tm^{+3}$, $Dy^{+3}$, $Yb^{+3}$, $Mn^{+2}$, $Fe^{+3}$, $^{55}Co$, $^{64}Cu$, $^{67}Cu$, $^{47}Sc$, $^{66}Ga$, $^{68}G$, $^{90}Y$, $^{97}Ru$, $^{99}mTc$, $^{111}h$, $^{109}Pd$, $^{153}Sm$, $^{177}Lu$, $^{186}Re$, and $^{133}Re$; or salts thereof.

In some embodiments, $L_1$ can include at least one of a polyalkyleneoxide, polyvinyl alcohol, polyethylene glycol (PEG), polypropylene glycol (PPG), co-poly (ethylene/propylene) glycol, polyoxyethylene (POE), polyurethane, polyphosphazene, polysaccharides, dextran, polyvinylpyrrolidones, polyvinyl ethyl ether, polyacryl amide, polyacrylate, or polycyanoacrylates.

In other embodiments, the probe can have the formula:

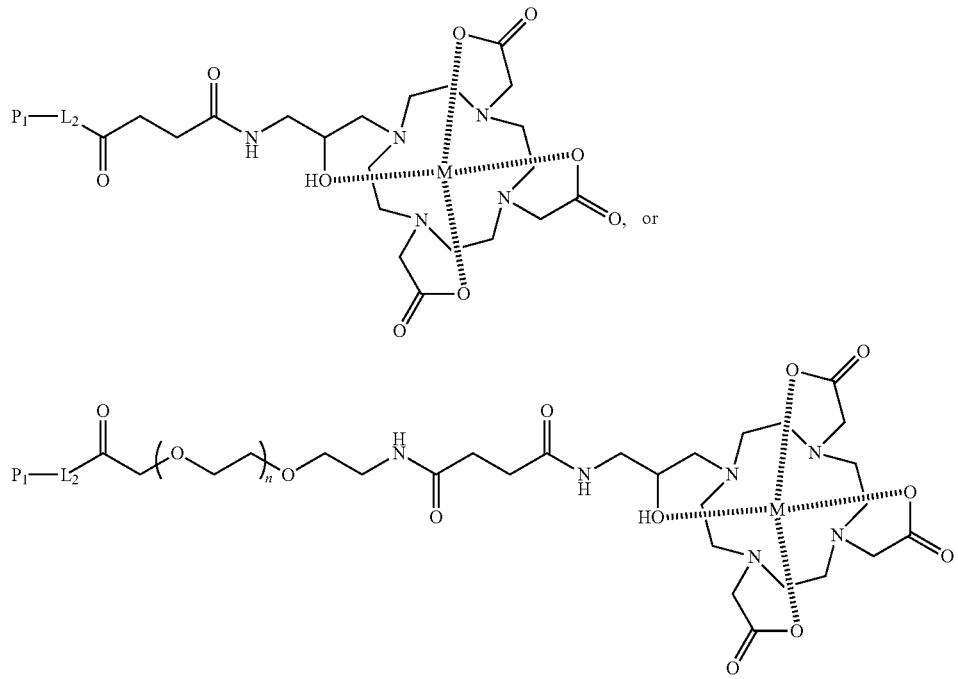

wherein:
P₁ is a peptide having an amino acid sequence selected from the group consisting of SEQ ID NO: 1. SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9;
L₂ is an amino group of the peptide P₁, and
M is a metal selected from the group consisting of $Gd^{+3}$, $Eu^{+3}$, $Tm^{+3}$ $Dy^{+3}$, $Yb^{+3}$, $Mn^{+3}$, $Fe^{+3}$, $^{55}Co$, $^{64}Cu$, $^{67}Cu$, $^{47}Sc$, $^{66}Ga$, $^{68}Ga$, $^{90}Y$, $^{97}Ru$, $^{99}mTc$, $^{111}h$, $^{109}Pd$, $^{153}Sm$. $^{177}Lu$, $^{186}Re$, and $^{188}Re$, and
n is an integer from 0 to 100; or salts thereof.

The molecular probe described herein can be administered to the subject by, for example, systemic, topical, and/or parenteral methods of administration. These methods include, e.g., injection, infusion, deposition, implantation, or topical administration, or any other method of administration where access to the tissue by the molecular probe is desired. In one example, administration of the molecular probe can be by intravenous injection of the molecular probe in the subject. Single or multiple administrations of the probe can be given. "Administered", as used herein, means provision or delivery of a molecular probe in an amount(s) and for a period of time(s) effective to label cancer cells in the subject.

Molecular probes comprising the targeting peptides described herein can be administered to a subject in a detectable quantity of a pharmaceutical composition containing a molecular probe or a pharmaceutically acceptable water-soluble salt thereof, to a patient.

A "detectable quantity" means that the amount of the molecular probe that is administered is sufficient to enable detection of binding or complexing of the probe to EDB-FN and/or EDA-FN expressed by the cancer cells or other cells in the cancer cell microenvironment. An "imaging effective quantity" means that the amount of the molecular probe that is administered is sufficient to enable imaging of binding or complexing of the molecular probe to the EDB-FN and/or EDA-FN of the cancer cells or other cells in the cancer cell microenvironment.

Formulation of the molecular probe to be administered will vary according to the route of administration selected (e.g., solution, emulsion, capsule, and the like). Suitable pharmaceutically acceptable carriers may contain inert ingredients which do not unduly inhibit the biological activity of the compounds. The pharmaceutically acceptable carriers should be biocompatible, e.g., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. Formulation will vary according to the route of administration selected (e.g., solution, emulsion, capsule).

Any polypeptide or compound may also be used in the form of a pharmaceutically acceptable salt. Acids, which are capable of forming salts with the polypeptides, include inorganic acids such as trifluoroacetic acid (TFA) hydrochloric acid (HC), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Bases capable of forming salts with the polypeptides include inorganic bases, such as sodium hydroxide, ammonium hydroxide, potassium hydroxide and the like; and organic bases such as mono-, di- and tri-alkyl and arylamines (e.g., triethylamine, diisopropylamine, methylamine, dimethylamine and the like) and optionally substituted ethanolamines (e.g., ethanolamine, diethanolamine and the like).

The molecular probes can be used in a method to detect and/or determine the presence, location, and/or distribution of cancer cells expressing EDB-FN and/or EDA-FN, in an organ, tissue, or body area of a subject. The presence, location, and/or distribution of the molecular probe in the animal's tissue, e.g., prostate tissue, can be visualized (e.g., with an in vivo imaging modality described above). "Distribution" as used herein is the spatial property of being scattered about over an area or volume. In this case, "the distribution of cancer cells" is the spatial property of cancer cells being scattered about over an area or volume included in the animal's tissue, e.g., prostate tissue. The distribution of the molecular probe may then be correlated with the presence or absence of cancer cells in the tissue. A distribution may be dispositive for the presence or absence of a cancer cells or may be combined with other factors and symptoms by one skilled in the art to positively detect the presence or absence of migrating or dispersing cancer cells, cancer metastases or define a tumor margin in the subject.

In one aspect, the molecular probes may be administered to a subject to assess the distribution of malignant or metastatic cancer cells in a subject and correlate the distribution to a specific location. Surgeons routinely use stereotactic techniques and intra-operative MRI (iMRI) in surgical resections. This allows them to specifically identify and sample tissue from distinct regions of the tumor such as the tumor edge or tumor center. Frequently, they also sample regions of tissue on the tumor margin that are outside the tumor edge that appear to be grossly normal but are infiltrated by dispersing tumor cells upon histological examination.

Molecular probes that specifically bind to and/or complex with EDB-FN and/or EDA-FN associated with malignant or metastatic cells can be used in intra-operative imaging techniques to guide surgical resection and eliminate the "educated guess" of the location of the tumor margin by the surgeon. Previous studies have determined that more extensive surgical resection improves patient survival. Thus, molecular probes that function as diagnostic molecular imaging agents have the potential to increase patient survival rates.

In some embodiments, to identify and facilitate removal of cancers cells, microscopic intra-operative imaging (IOI) techniques can be combined with systemically administered or locally administered molecular probes described herein. The molecular probe upon administration to the subject can target and detect and/or determine the presence, location, and/or distribution of cancer cells, i.e., cancer cells associated with EDB-FN and/or EDA-FN expression, in an organ or body area of a patient. In one example, the molecular probe can be combined with IOI to identify malignant cells that have infiltrated and/or are beginning to infiltrate at a tumor margin. The method can be performed in real-time during surgery. The method can include local or systemic application of the molecular probe that includes a detectable moiety, such as a PET, fluorescent, or MRI contrast moiety. An imaging modality can then be used to detect and subsequently gather image data. The resultant image data may be used to determine, at least in part, a surgical and/or radiological treatment. Alternatively, this image data may be used to control, at least in part, an automated surgical device (e.g., laser, scalpel, micromachine) or to aid in manual guidance of surgery. Further, the image data may be used to plan and/or control the delivery of a therapeutic agent (e.g., by a micro-electronic machine or micro-machine).

Another embodiment described herein relates to a method of determining the aggressiveness or malignancy of cancer cells in a subject. It was found that the binding intensity of the molecular probes to a cancer correlated with the cancer aggressiveness. Enhanced binding correlated with more aggressive cancer whereas lower or reduced binding correlated with less aggressive or benign tumors. In one example, binding of the molecular probe to prostate tumor sections correlated with to Gleason score based on tumor aggressiveness, where enhanced binding intensity of the molecular probe correlated to aggressive or malignant prostate cancer and which was distinguished from benign prostatic hyperplasia, which displayed lower binding intensity of the probe. The methods and molecular probes described herein can be used to monitor and/or compare the aggressiveness a cancer in a subject prior to administration of a cancer therapeutic or cancer therapy, during administration, or post therapeutic regimen.

Another embodiment described herein relates to a method of monitoring the efficacy of a cancer therapeutic or cancer therapy administered to a subject. The methods and molecular probes described herein can be used to monitor and/or compare the aggressiveness, invasion, migration, dispersal, and metastases of a cancer in a subject prior to administration of a cancer therapeutic or cancer therapy, during administration, or post therapeutic regimen.

A "cancer therapeutic" or "cancer therapy", as used herein, can include any agent or treatment regimen that is capable of negatively affecting cancer in an animal, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of an animal with cancer. Cancer therapeutics can include one or more therapies such as, but not limited to, chemotherapies, radiation therapies, hormonal therapies, and/or biological therapies/immunotherapies. A reduction, for example, in cancer volume, growth, migration, and/or dispersal in a subject may be indicative of the efficacy of a given therapy. This can provide a direct clinical efficacy endpoint measure of a cancer therapeutic. Therefore, in another aspect, a method of monitoring the efficacy of a cancer therapeutic is provided. More specifically, embodiments of the application provide for a method of monitoring the efficacy of a cancer therapy.

The method of monitoring the efficacy of a cancer therapeutic can include the steps of administering in vivo to the animal a molecular probe as described herein, then visualizing a distribution of the molecular probe in the animal (e.g., with an in vivo imaging modality as described herein), and then correlating the distribution of the molecular probe with the efficacy of the cancer therapeutic. It is contemplated that the administering step can occur before, during, and after the course of a therapeutic regimen in order to determine the efficacy of a chosen therapeutic regimen. One way to assess the efficacy of the cancer therapeutic is to compare the distribution of a molecular probe pre and post cancer therapy.

In some embodiments, the molecular probe bound to and/or complexed with the EDB-FN and/or EDA-FN is detected in the subject to detect and/or provide the aggressiveness, location and/or distribution of the cancer cells in the subject. The aggressiveness, location and/or distribution of the cancer cells in the subject can then be compared to a control to determine the efficacy of the cancer therapeutic and/or cancer therapy. The control can be the location and/or distribution of the cancer cells in the subject prior to the administration of the cancer therapeutic and/or cancer therapy. The location and/or distribution of the cancer cells in the subject prior to the administration of the cancer therapeutic and/or cancer therapy can be determined by administering the molecular probe to the subject and detecting the molecular probe bound to and/or complexed with cancer cells in the subject prior to administration of the cancer therapeutic and/or cancer therapy.

In certain embodiments, the methods and molecular probes described herein can be used to measure the efficacy of a therapeutic administered to a subject for treating a metastatic or aggressive cancer. In this embodiment, the molecular probe can be administered to the subject prior to, during, or post administration of the therapeutic regimen and the distribution of cancer cells can be imaged to determine the efficacy of the therapeutic regimen. In one example, the therapeutic regimen can include a surgical resection of the metastatic cancer and the molecular probe can be used to define the distribution of the metastatic cancer pre-operative and post-operative to determine the efficacy of the surgical resection. Optionally, the methods and molecular probes can be used in an intra-operative surgical procedure, such as a surgical tumor resection, to more readily define and/or image the cancer cell mass or volume during the surgery.

In other embodiments, the targeting peptides can be conjugated to a therapeutic agent and administered to a subject for treating a cancer, such as a metastatic cancer. In this embodiment, the targeting peptides can be administered to the subject prior to, during, or post administration of the therapeutic agent and the distribution of metastatic cells can be targeted with the therapeutic agent.

The therapeutic agent can include an anti-proliferative agent that exerts an antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in preclinical development. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

In some embodiments, the targeting peptides can be coupled to the therapeutic agent using a linking molecule. The linking molecule may be a peptide linker. Alternatively, a linking molecule may be a non-peptide linker.

EXAMPLES

Example 1

We identified small peptide sequences that specifically bind to onfFN isoforms for molecular imaging of prostate cancer. Although antibodies specific to the protein has been reported in the literature, small peptides are advantageous for their lack of immunogenicity, cost effectiveness of manufacture, and readiness for translational development. In this Example, we describe a small peptide specific to EDB-FN identified by phage display. A peptide-Cy5 conjugate was synthesized for molecular imaging of the biomarker. The binding property of the peptide to EDB-FN was investigated in vitro, in vivo, and in human prostate cancer specimens using the peptide-Cy5 conjugate.

Materials and Methods

Material

All reagents were used without further purification unless otherwise stated. 2-Chlorotrityl chloride resin and all of the Fmoc protected amino acids were purchased from Chem-Impex International, Inc. Fmoc-12-amino-4,7,10-trioxadodecanoic acid were purchased from EMD Chemicals Inc. (Gibbstown, N.J., USA). Sulfo-Cy5.0 NHS ester was purchased from Lumiprobe (Hallandale Beach, Fla.). Anhydrous N, N-diisopropylethyl amine (DIPEA) and N,N-dimethylformamide (DMF) were purchased from alfa Aesar (Ward Hill, Mass., USA). Trifluoroacetic acid (TFA) was purchased from Oakwood Products, Inc (West Columbia, S.C.). FastDigest enzymes for plasmid construction were purchased from Fermantas (Thermo Scientific Co., Rockford, Ill., USA)

EDB Expression with *E. coli*

DNA sequence of EDB was optimized and synthesized (GeneArt, Regensburg, Germany) before being cloned into pQE-T7-1 expression vector (Qiagen, Valencia, Calif., USA) with NdeI and PstI restriction sites according to user's manual. Production of EDB was induced by 1 mM IPTG at the mid-log phage of growing *E. coli* strain BL21 (Sigma-Aldrich, St Louis, Mo., USA). Purification of EDB through 10×His tag was carried out with Ni Sepharose 6 Fast Flow (GE healthcare, Waukesha, Wis., USA), followed by dialysis against water and lyophilization. Expression and purification were evaluated with SDS-PAGE.

Phage Screening

The Ph.D C7C library (New England Biolabs, Beverly, Mass., USA) was used for screen EDB specific nonapeptides. Candidate peptides were selected by carrying out panning procedures for 4 rounds. In each round, purified EDB fragment (100 μg/ml) was immobilized on non-treated 96-well plates (Corning Costar, Tewksbury, Mass., USA) with overnight coating at 4° C. 0.5% BSA was used to block non-specific binding (1 hr, room temperature) followed by incubating with phages for 1 hr at room temperature. Extensive washing with PBST (0.1%, 0.3%, 0.5% BSA, respectively, for round 1-3) was used to remove non-binding phages before eluting bound phages by 0.1M Glycine-HC (pH 2.2) and neutralizing with Tris-HCl (pH 9.1). Eluted phages are tittered and amplified with *E. coli* (ER2758) according to the user's manual. Amplified phages in medium were purified by ultrafiltration and PEG/NaCl precipitation. At the end of round 4, properly diluted phages were cultured on LB/IPTG/Xgal plates and DNA from 29 randomly picked blue plaques were used for sequencing with supplied primers (New England Biolabs). Peptide sequences were resulted from translating of corresponding DNA sequences.

Peptide Synthesis

ZD2 peptide with the sequence of CTVRTSADC was synthesized based on standard solid-phase synthesis from Fmoc-protected amino on a 2-chlorotrityl chloride resin. PEG (Fmoc-12-amino-4,7,10-trioxadode-canoic acid), and Sulfo-Cy5.0 NHS ester were sequentially conjugated to the N terminal of the peptide to form fluorescent ZD2 probe (ZD2-Cy5). Cyclization of the peptide was carried out by exposing the peptide to air in 10% DMSO/PBS. Purification of the cyclic peptide was done using RP-HPLC followed by lyophilization. The peptide and peptide ZD-2 conjugate were characterized by MALDI-TOF mass spectrometry.

Peptide ELISA

A linear version of ZD2 (CTVRTSADA) SEQ ID NO: 42 was synthesized so that sulfhydryl group on cysteine could be used for conjugation with maleimide-activated peroxide (Sigma-Aldrich). Conjugation was carried out as instructed in the manual. The product of conjugation, ZD2-HRP, was used for peptide ELISA assay after coating a 96-well plate with purified EDB. 0.5% BSA in PBS was used to block non-specific binding for later steps. 0.39 µM to 50 µM of ZD2-HRP was incubated with coated EDB for an hour followed by extensive washing with TBST (0.1%). ABTS substrate was added subsequently and allowed to react for 30 min before the absorbance of solution in each well were measured at 415 nm. Non-coated wells added with ABTS were used as blank.

In Vitro Cellular Binding

PC3 cell line was purchased from American Type Culture Collection (ATCC, Manassas, Va., USA), and maintained in RPMI/10% FBS medium. The cells were transfected with lentivirus to express green fluorescent protein (GFP) at least 48 h prior to harvesting. To induce EMT, PC3 cells were cultured in the presence of TGFβ1 (5 ng/ml) for 5 days. For in vitro binding assay, nuclei of cells were stained with Hoechst 33342 (Life Technologies, Brooklyn, N.Y., USA) 24 h prior to adding 500 nM ZD2-Cy5. Cells were maintained in medium containing ZD2-Cy5 for 24 h and monitored with confocal microscopy. Intense shaking was avoided for live-cell binding study to retain secreted EDB-FN on the glass.

In Vivo Binding in a Mouse Tumor Model

NIH athymic male nude mice, age 4-5 weeks, were maintained at the Athymic Animal Core Facility at Case Western Reserve University according to the animal protocols approved by the Institutional Animal Care and Use Committee (IACUC). For whole-body fluorescent imaging study, a flank tumor model was constructed. Each mouse was subcutaneously implanted in both flanks with $2\times10^6$ PC3-GFP cells mixed with an equal volume of in a mixture of PBS (50 µL culture medium and 50 µL PBS). Two to three weeks after inoculation, tumors reached an average size of 0.5 cm in diameter. The mice were used for imaging with Maestro FLEX In vivo Imaging System (Cambridge Research & Instrumentation, Inc. Woburn, Mass., USA) to monitor the targeting effect of ZD2 from 0 to 24 hours. Mice were intravenously injected with ZD2-Cy5 or CERAK-Cy5 (0.3 µmol/kg body weight). After 5 h, the mice were sacrificed and the tumor and various organs were imaged with the Maestro FLEX In vivo Imaging System.

Histological Staining of Human Prostate Sections

Human prostate sections were acquired from OriGene (Rockville, Md., USA). Antibodies used in this study include mouse monoclonal anti-Fibronectin antibody (BC-1, ab154210, Abcam, Cambridge, UK), Rhodamine-Red-X conjugated goat polyclonal anti-rabbit IgG (H+L) (Jackson Immuno Research Lab. West Grove, Pa., USA), and FITC conjugated goat polyclonal anti-mouse Fc (ab97264, Abcam). Frozen tissue section (5 nm) imbedded in OCT was used for immunostaining and peptide staining. Paraffin embedded samples were de-paraffinized and processed with antigen retrieval using general methods. Sections were permeabilized and fixed with cold acetone followed by 0.5% BSA blocking for 1 hr at room temperature. Peptide staining was carried at the concentration of 5 uM. Slides were counter-stained with DAPI and mounted with coverslip using Prolong Gold regent (Invitrogen) before imaging. Stained tissue was imaged on an Olympus FV1000 confocal laser scanning microscope. GFP was observed using 405 nm laser and the emission wavelength was read from 480 to 495 nm and represented as green. DAPI was observed using 405 nm laser and the emission wavelength was read from 450 to 470 nm and expressed as blue. Cy5.0 was observed using 635 nm laser and the emission wavelength was read from 655 to 755 nm and expressed as red.

qPCR

Total RNA was collected from cell samples and isolated using an RNeasy Plus Kit (Qiagen). RNA was then reversely transcribed into cDNA using the High Capacity cDNA Transcription Kit (Applied Biosystems, Foster City, Calif.). Semiquantitative real-time PCR was carried out using a SYBR Green Master Mix (Life Technologies) according to the manufacturer's recommendations. RNA concentration for individual genes examined was normalized to their corresponding GAPDH RNA signals. Both cDNA synthesis and real-time PCR were carried out on the Mastercycler realplex2 (VWR International, West Chester, Pa., USA). Relative mRNA expression levels were calculated using the $2^{-\Delta\Delta CT}$ method. The oligonucleotide primer pair sequences were 5'-GCAGCCCACAGTGGAGTAT-3' (SEQ ID NO: 31) for EDB sense and 5'-GGAGCAAGGTITGATCTTT-3' (SEQ ID NO: 32) for antisense, 5'-GCAGCCCACAGTG-GAGTAT-3' (SEQ ID NO: 33) for EDA sense and 5'-GGA GCAAGGTGATTTCTT-3' (SEQ ID NO: 34) for antisense, 5'-ACCCAGAAGACTGTGGATGG-3' (SEQ ID NO: 35) for GAPDH sense and 5'-TCTA-GACGGCAGGTCAGGTC-3' (SEQ ID NO:36) for antisense, 5'-TGCCCAGAAAATGAAAAAGG-3' (SEQ ID NO: 37) for E-cadherin sense and 5'-GTGTATGTGGCAATGCGTTC-3' (SEQ ID NO: 38) for antisense, and 5'-ACAGTGGCCACCTACAAAGG-3' (SEQ ID NO: 39) for N-cadherin sense and 5'-CCGAGATGGGGTTGATAATG-3' (SEQ ID NO: 40) for antisense. The primers were purchased from Invitrogen.

Western Blot

Tissues from mice were lysed with T-PER Tissue Protein Extraction Reagent (Thermo scientific) supplemented with PMSF (Sigma) and protease inhibitors (Sigma) according to manufacturer's instructions. Human prostate lysates were acquired from OriGene and used under manufacturer's instruction. 20 µg proteins were loaded for electrophoresis and blotting. Gels, PVDF membranes and other related reagents were purchased from Biorad (Hercules, Calif., USA) and used according to manufacturer's instructions. General Electric Typhoon Phosphor imager was used for processing membrane blotted with FITC conjugated secondary antibody.

Statistical Analysis

All data are presented as mean±SEM except stated. When two groups were compared, the two-tailed Student's t test was used (p<0.05 was considered significant).

Results

EDB-FN Binding Peptide

EDB is a type-III-homology repeat with a sequence of 91 amino acids encoded by a single exon, which are identical in vertebrates. The EDB fragment was expressed in E. coli by cloning codon optimized DNA sequence of EDB into an expression plasmid, pQE-T7-1, under the regulation of T7 promoter, as shown in FIG. 1A. The ligation of EDB DNA in the plasmid was verified by DNA sequencing. Expression and purification of EDB fragment were confirmed by SDS-PAGE as shown in FIG. 1B. A M13 phage library displaying cyclic nonapeptide flanked by two cysteine residues on its pIII protein was used for screening EDB binding peptides. Four rounds of panning yielded an enriched phage library containing phages with high EDB binding ability, which was determined by phage ELISA assay. Out of 29 identified phage clones, the peptide sequence of CTVRTSADC (SEQ ID NO: 10) appeared 5 times and was named ZD2.

Cyclic ZD2 peptide (CTVRTSADC) (SEQ ID NO: 10) was synthesized using standard solid phase peptide chemistry and was characterized by MALDI-TOF mass spectrometry (FIG. 1C). The peptide was then labeled with a fluorescence chromophore cyanine 5 (Cy5) through a short PEG linker ($NH_2$—($CH_2CH_2O$)—$CH_2CH_2COOH$) to give a peptide fluorescence probe ZD2-Cy5. The peptide was also conjugated to peroxidase (ZD2-HRP) and the binding affinity of the peptide to EDB fragment was determined using peptide ELISA assay. FIG. 1D shows the concentration-dependent binding curve of ZD2-HRP to the EDB fragment, which gave the binding affinity ($K_D$, the equilibrium dissociation constant) of 4.52±2.68 µM between ZD2-HRP and EDB.

In Vitro Peptide Binding to EDB-FN Excreted by TGFβ1-Induced PC3 Cancer Cells

Elevated expression of onfFN is a marker of EMT of prostate cancer cells. The treatment of PC3 human prostate cancer cells with TGFβ1 resulted in an elongated mesenchymal phenotype as compared with cells without induction, as shown in FIG. 2A. Up-regulation of EDB-FN expression was companied with E-Cad down-regulation and N-Cad up-regulation as determined by quantitative PCR (FIG. 2B). As a result, ZD2-Cy5 showed substantially more binding to the periphery of the PC3 cells treated with TGFβ1 than the untreated cells because of the production and secretion of EDB-FN by the TGFβ1-induced cells as shown in FIG. 2C.

In Vivo Binding of ZD2-Cy5 in a Mouse PC3 Prostate Tumor Model

Whole-body fluorescence imaging of mice bearing PC3-GFP flank tumor xenografts showed significantly high accumulation of ZD2-Cy5 in tumor (FIG. 3A). Tumor of mice injected with ZD2-Cy5 was clearly highlighted in the Cy5 fluorescence image at 1.5 h after intravenous injection. Relatively high tumor to normal (T/N) ratio of Cy5 signal could be maintained for up to 24 hours for mice injected with ZD2-Cy5, compared with mice injected with a non-specific control CERAK-Cy5 (FIG. 3B). Tumor and major organs were collected to image the Cy5 signal 5 hours after injection. The result verified the specific accumulation of Cy5 labeled ZD2 in tumor, while little tumor accumulation was seen for mice injected with CERAK-Cy5 (FIG. 3C). Western blot analysis of protein lysates from tumor, liver, and lung indicated that PC3 tumor expresses substantially more EDB-FN than in the liver and lung, as shown in FIG. 3D.

Imaging of the tissue sections from the tumor bearing mice injected with ZD2-Cy5 or CERAK-Cy5 further verified the specific binding of ZD2-Cy5 in the tumor, and the Cy5 signal was distributed in the ECM of the tumor. Little accumulation of ZD2-Cy5 was found in the liver or lung (FIG. 4A). Since EDB-FN is a biomarker for angiogenesis, we did immunofluorescence staining on those tumor sections using antibodies specific to EDB-FN and CD31. BC-1 was chosen as a reference to correlate ZD2 distribution with EDB-FN expression, while anti-CD31 antibody was used to correlate angiogenesis. Immunofluorescence images in FIG. 4B confirmed the overlap between ZD2-Cy5 binding with both FN expression and angiogenesis.

ZD2-Cy5 Binding in Prostate Cancer of Different Aggressiveness

The binding activity of ZD2-Cy5 was further assessed in human prostate tumor sections of different Gleason scores. A human prostate BPH section was used as a control. As shown in FIG. 5A and FIG. 5C, tumor with high Gleason score exhibited strong staining with ZD2-Cy5 in both stromal and glandular areas, while normal glands were unstained. Similar trend was also observed with BC-1 immunofluorescence staining. Histogram analysis of Cy5 fluorescence images acquired from the ZD2 stained sections indicated a shift of pixel value distribution from low intensity values to high intensity values as the Gleason score of tumor increases from GS 7 to GS 9 (FIG. 5B). In histogram analysis, measuring the pixel intensity ranging from 50 to 255 on the 8-unit images clarified the increase in ZD2 binding on sections of higher Gleason score. Protein lysates from normal prostate and cancerous prostate (GS=3+4) were also analyzed with Western blot in order to confirm the high expression of EDB-FN in cancer samples (FIG. 5D). Competitive staining by blocking sections with BC-1 inhibited the tumor binding ZD2-Cy5 (FIG. 5E). This result indicates that BC-1 and ZD2 share the same molecular target.

We have identified cyclic nonapeptide ZD2 with good binding affinity to EDB-FN using phage display. The binding specificity of the peptide was first verified using a fluorescence probe ZD2-Cy5 in vitro in post-EMT PC3 prostate cancer cells. ZD2-Cy5 showed strong binding of in post-EMT PC3 cells and non-binding in uninduced cells. Strong binding of ZD2-Cy5 to induced PC3 cells was localized at cell periphery, which was in agreement with the fact that FN was an ECM protein. EMT induction of PC3 cells by TGFβ1 resulted in substantial up-regulation of EDB-FN in post-EMT PC3 prostate cancer cells and strong binding. EMT is generally associated with invasive cancer types. The results suggest that EDB-FN is a potential biomarker of aggressive prostate cancer and ZD2 peptide is a viable probe for the biomarker. The tumor binding specificity was further demonstrated in mice bearing PC3-GFP prostate cancer xenografts.

The binding activity of ZD2 was further tested in human prostate tumor sections of different Gleason score. Gleason score is the most commonly used pathological grading system in clinical management of prostate cancer. Our histological staining experiment showed that ZD2-Cy5 had strong binding prostate tumors (GS7 and GS9), not in BPH tumor sections. The binding intensity of ZD2-Cy5 in the tumor sections appears correlated to Gleason score based tumor aggressiveness, which is in agreement with the previous study that showed an overexpression of EDB-FN in prostate carcinoma compared with BPH. The results suggest EDB-FN as a desirable marker for differentiating prostate cancer from BPH.

Currently, the needle-biopsy Gleason scoring is routinely used in the risk-stratified management of prostate cancer and decision making. The goal of this risk-stratified management strategy is to minimize the treatment-related harm to patients who do not benefit from treatment. However, the accuracy of diagnostic procedure is often compromised by the heterogeneity of cancer within the same prostate and the inadequacy of prostate sampling from needle-biopsy. Therefore, a molecular imaging technology with the potential of non-invasively mapping the aggressiveness of prostate cancer throughout the prostate is advantageous over invasive biopsy and could provide more accurate differential diagnosis. A number of molecular targets have been tested for prostate cancer molecular diagnosis. For example, cell-surface biomarkers PSMA, N-Cadherin and hepsin, and intracellular markers DD3/PCA3 and GalNAc-T3 have been investigated as markers for prostate cancer. However, it is still uncertain whether these targets could be used as indicators for cancer aggressiveness. EDB-FN is a molecular marker prostate cancer angiogenesis and EMT, characteristics of cancer aggressiveness. Molecular imaging EDB-FN could provide non-invasive differential diagnosis of prostate cancer. The abundant expression of EDB-FN in tumor ECM would be more accessible to molecular probes, which lead to improved binding of imaging probe.

Example 2

In this Example, we developed an EDB-FN targeted contrast agent, l-ZD2-Gd(HP-DO3A) for molecular imaging of micrometastases. This contrast agent is rationally designed based on an EDB targeting peptide, ZD2, discovered by phage display technique. The linear version of this peptide, l-ZD2, has been evaluated for its targeting capacity. A modular system for gadolinium complexation is used in conjugation with l-ZD2. This small gadolinium-based contrast agent targets to EDB-FN secreted by cancer cells and fibroblasts, etc., with minimal accumulation in normal tissues. Overexpression of EDB-FN in cellular level may considerably contribute to early and sensitive detection of micrometastases. In this Example, we assessed the effectiveness of l-ZD2-Gd(HP-DO3A) in detecting micrometastases at early stage following tumor inoculation. These results demonstrate that EDB-FN targeted contrast agent can more efficiently detect micrometastases with a smaller size, thus increasing detecting sensitivity for a better diagnosis.
The Use of Linear ZD2 for EDB-FN Targeting We previously reported the discovery of a cyclic nonapeptide, ZD2 (CTVRTSADC) (SEQ ID NO: 10) that specifically targets EDB-FN. However, cyclization of ZD2 with disulfide bond tends to complicate further chemical modification with the possibility of intermolecular linkage. Thus, we assessed the capability of the linear version, l-ZD2 (TVRTSAD) (SEQ ID NO: 1), with the expectation that l-ZD2 would perform similarly to cyclic ZD2. To measure binding affinity between l-ZD2 and EDB protein, the peptide with a sequence of $NH_2$-TVRTSADC-COOH (SEQ ID NO: 41) is synthesized in solid phase. The thiol group on the cysteine is used to conjugate maleimide activated horseradish peroxidase (HRP), resulting in l-ZD2-HRP. Similarly, CERAK-HRP is synthesized as a control. ELISA (Enzyme linked immunosorbent assay) showed that l-ZD2-HRP bound to EDB protein with an affinity of xxx $\mu mol^{-1}$, which is comparable to cyclic ZD2 with a slight increase in affinity, while CERAK-HRP showed no observable binding to EDB. No binding between l-zd2-HRP and EDA was seen. Since it is believed that cyclized peptide possesses more structural stableness in vivo, we evaluated the stableness of l-ZD2 in human serum within 24 hours with HPLC. No degradation was seen of l-ZD2 at 24 hours from the spectrum. Therefore, we can conclude that the linear version of ZD2 can also be used for EDB-FN targeting.
Upregulation of EDB-FN is a Hallmark of Breast Cancer Metastasis 4T1 cells have been shown to upregulate fibronectin expression as a result of transforming growth factor-beta (TGFβ) induction. TGFβ is a key regulator of epithelial-to-mesenchymal transition (EMT), which is believed as the driving force of metastasis. To demonstrate the use of EDB-FN as a biomarker for metastases targeting, we compared the mRNA level of EDB-FN in normal 4T1 cells and 4T1 cells with 5 days of TGFβ induction. Notably, there is a three-fold upregulation of EDB-FN in 4T1 cells as a result of TGFβ induction. (FIG. 6A). Western blot analysis of protein extracts of metastatic tumors from different organ compared with primary tumor also showed the upregulation of EDB-FN in tissue level. (FIG. 6B). Minimal EDB-FN expression is seen in normal tissues, such as brain, lung and liver. Together, these results supported the hypothesis that EDB-FN can be used as an efficient biomarker for targeting metastatic tumors.

Figure 8A:
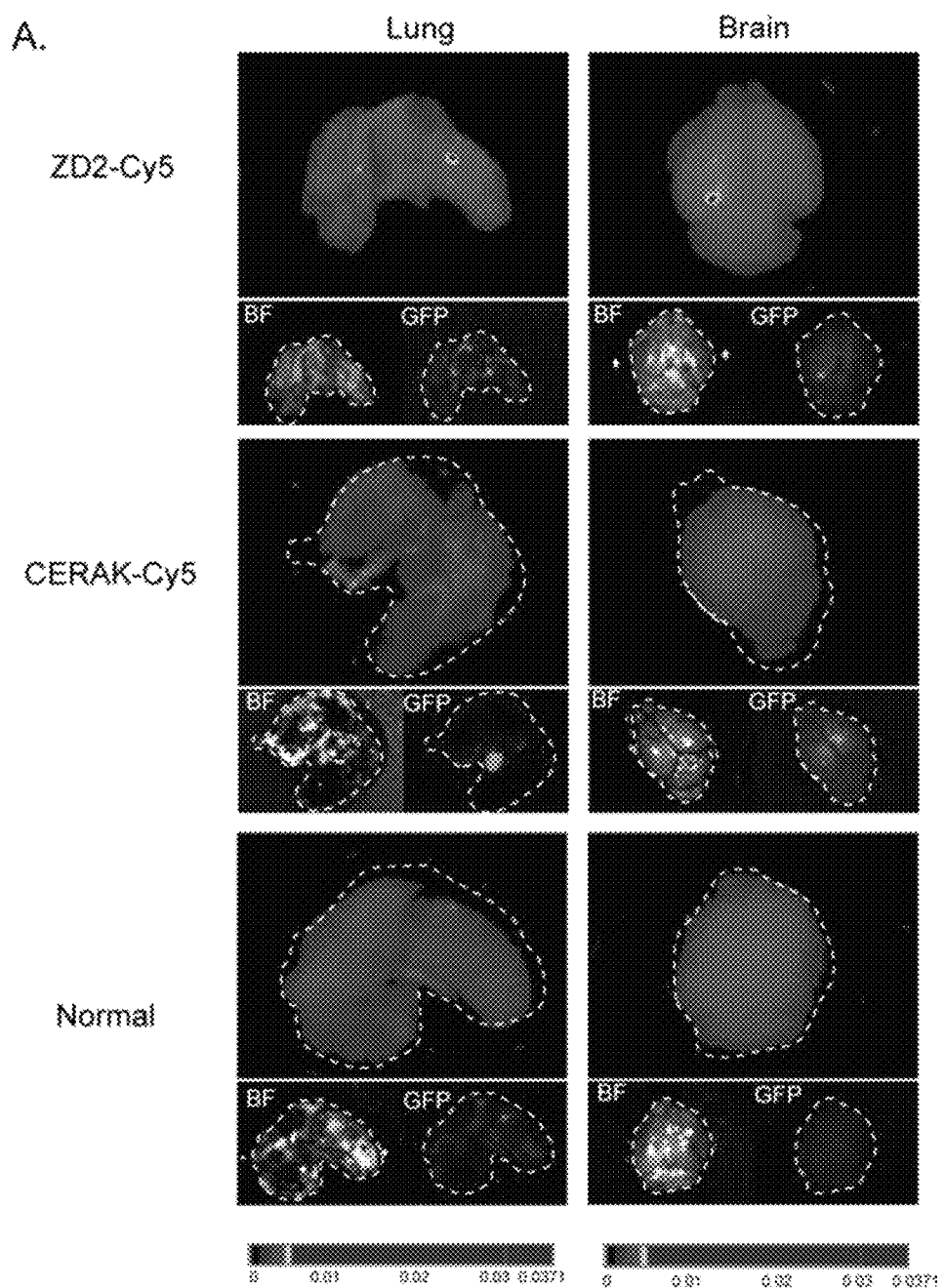
FIGS. 8(A-C) illustrate: A) Bright field, GFP and Cy5 images of lung and brain harvested from mice injected with ZD2-Cy5 or CREKA-Cy5. Normal mice bearing no tumors were used as a control. Cy5 signal was presented with jetblack colormap. Display keys for the colormaps of each group were shown in below. B) Maestro fluorescent images of muscle, lymph node metastatic tumor (LN Mets), and adrenal gland tumor (AG Mets). Cy5 signal was represented with jetblack colormap. Display keys were shown in below. GFP images were also shown. C) Confocal microscopic images of the cryosections of tumor from mice injected with l-ZD2-Cy5. Nucleus staining (DAPI, a), GFP (b), Cy5 (c), and merged images were shown.

As tumor cells produce EDB-FN to promote its migration, we further validated if Cy5 labeled l-ZD2 (l-ZD2-Cy5) can bind to TGFβ induced 4T1 cells in vitro. Our result suggested that l-ZD2-Cy5 is bound to induced 4T1 cells within 3 hours, but no binding between CREKA-Cy5 on induced 4T1 cells was seen. To explain this, we hypothesize that in this form of cell culture, no clot formation can take action to provide binding sites for CREKA-Cy5. To validate our hypothesis, we further produced a 3D culture system that mimics the "soil" of metastatic tumor. In the 3D culture system, 4T1 cells were cultured in a microenvironment containing TGFβ, collagen, and fibrin. It was found out that l-ZD2-Cy5 accumulated in the cell periphery starting from day 1. In overall, these evidences point to the conclusion that the use of EDB-FN for targeting micrometastasis may be advantageous compared with Fibronectin-Fibrin complexes in that EDB-FN appears earlier than Fibronectin-Fibrin in the pre-metastatic niche.
Design of an EDB-FN Targeted Gadolinium-Based Magnetic Resonance Probe The design of the EDB-FN targeted MRI agent was based on a modular system that forms small molecular contrast agent in conjugation with l-ZD2. Compound 1 in FIG. 7A was prepared by adding a short PEG linker, followed by reacting with 5-hexynoic acid, resulting in an alkyne group for conjugation through click chemistry. The final product from reaction of compound 1 and 2 was purified with HPLC and characterized with Maldi-Tof spectrum. (FIG. 7B) Measurement of relaxivities (T1 and T2) showed that the resulting compound possess relatively high relaxivities at 3T (FIG. 7C).
In Vivo Detection of Micrometastasis with l-Zd2-Cy5 in a Breast Cancer Metastatic Tumor Model In order to construct a metastatic tumor model, $0.2 \times 10^6$ 4T1 tumor cells undergone 5 days of TGFβ induction were injected through left ventricle of heart, resulting in the spread of tumor cells primarily in brain, lung, liver, lymph node, adrenal gland, chest, and bone marrow. Bioluminescent images of the mice at two weeks were used to monitor the growth of tumors. To assess the targeting capacity of l-ZD2-Cy5, brain and lung were harvested from the mice three hours after 10 nmol l-ZD2-Cy5 were injected. Signal from l-ZD2-Cy5 clearly outlined the micrometastases grown on brain and lung, with GFP signal from 4T1 consolidating the positions of tumors. (FIG. 8A) CERAK-Cy5, in contrary, didn't show binding on small metastatic tumors. Normal brain and lung harvested from normal mice injected with l-ZD2-Cy5 were used as negative controls. Examination of bigger metastatic tumors in lymph nodes and adrenal gland, as shown in FIG. 8B further backed up the targeting efficiency of l-ZD2-Cy5. Confocal laser scanning microscopy of cryosectioned tumor demonstrated that l-ZD2-Cy5 distributed in the ECM of the cells and forms a fibrillary network. Together, these results pave the path towards testing MRI probe based on l-zd2 for in vivo imaging of metastasis.

In Vivo Magnetic Resonance Imaging of Breast Cancer Metastasis with l-ZD2-Gd(HP-DO3A)

Breast cancer metastatic tumor model was imaged at two weeks in order to validate the properties of l-ZD2-Gd(HP-DO3A) in detecting breast cancer micrometastases. In FIG. 9A, a mouse developed with metastatic tumors in lymph nodes, adrenal glands, and chest was imaged in MRI after l-ZD2-Gd(HP-DO3A) injection, in conjugation with BLI validation of tumor positions. All five tumors indicated in BLI showed enhancement in MRI, with all the tumor positions accurately reflected. Representative images of tumors in the leg, shoulder, and lung were shown in FIG. 9B. Imaging of mice injected with CERAK-Gd(HP-DO3A) showed minimal tumor enhancement. CNR measurement of tumor, liver, kidney, bladder, and muscle demonstrated a significant higher signal enhancement of l-ZD2-Gd(HP-DO3A) in tumor (FIG. 9C).

Figure 10:
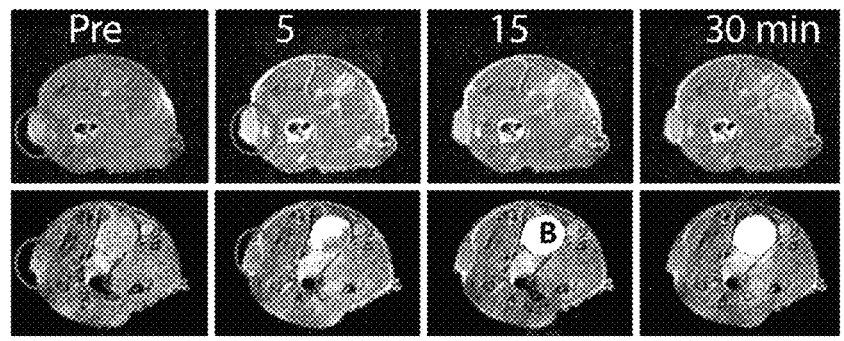
FIG. 10 illustrates T1-weighted 2D axial spin-echo MR images before (pre) and at 5, 15, 30 min after i.v. injection of ZD2-Gd(HP-DO3A) and Gd-(HP-DO3A) at 0.1 mmol-Gd/kg in mice bearing PC-3 prostate cancer xenograft. Circle, tumor, B, bladder.
Figure 11:
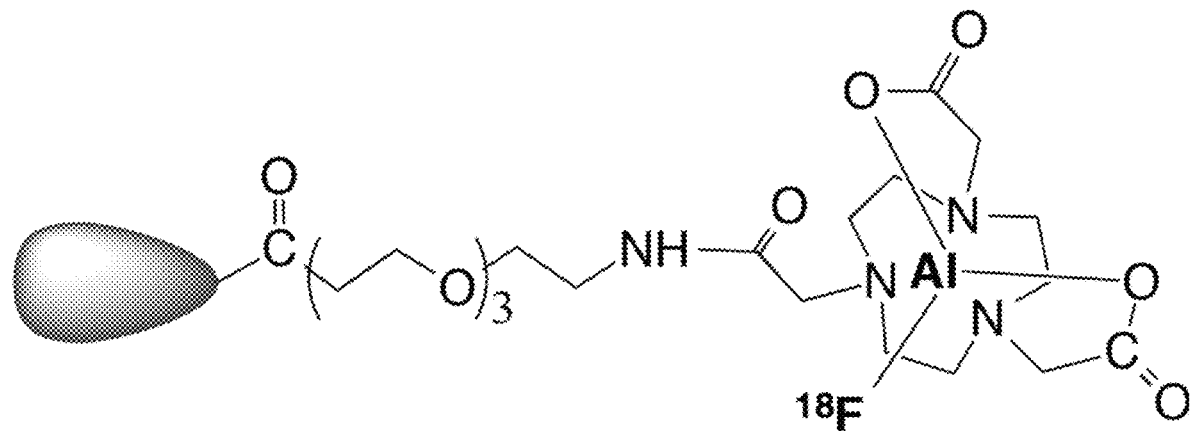
FIG. 11 is a schematic illustration of a molecular probe in accordance with an embodiment of the application.

The same contrast agent also works for prostate cancer imaging. We then tested the effectiveness of targeting EDB-FN with the contrast agent for prostate cancer MRI in male nude mice bearing primary PC-3 human prostate cancer xenograft. As shown in FIG. 10, the targeted agent produced robust tumor enhancement for at least 30 min after intravenous injection at a dose of 0.1 mmol-Gd/kg, while a clinical control Gd(HP-DO3A) generated little contrast enhancement under in the tumor under the same condition. The result indicates that the small molecular peptide targeted contrast agent specific to EDB-FN in tumor ECM is effective for contrast enhanced MRI of prostate cancer and EDB-FN is a viable molecular target for non-invasive detection of prostate cancer with molecular MRI.

Example 3

This example discloses design and synthesis route of a versatile molecular probe for magnetic resonance imaging (MRI) and positron emission tomography (PET). This probe allows for facile and fast chelation of gadolinium (Gd) or Copper-64 ($^{64}$Cu) ions for synthesis of MRI or PET probes. The probe described herein utilize a small peptide, named ZD2 (sequence: Thr-Val-Arg-Thr-Ser-Ala-Asp) (SEQ ID NO: 1), to direct the MRI or PET probe to diseases characterized by extradomain-B fibronectin (EDB-FN) overexpression, which induces image contrast in malignant sites, to improve diagnosis sensitivity and specificity of the disease and monitor disease progression and therapeutic responses. The contrast agent may be used for diagnosis of prostate cancer, breast cancer, etc. In this application, synthesis and characterization of the precursor (ZD2-HP-DO3A), MRI probe (ZD2-Gd(HP-DO3A)), PET probe (ZD2-Cu(HP-DO3A)), have been given. Further, preclinical testing of the MRI probe for differential diagnosis of prostate cancer is included.

General Structure

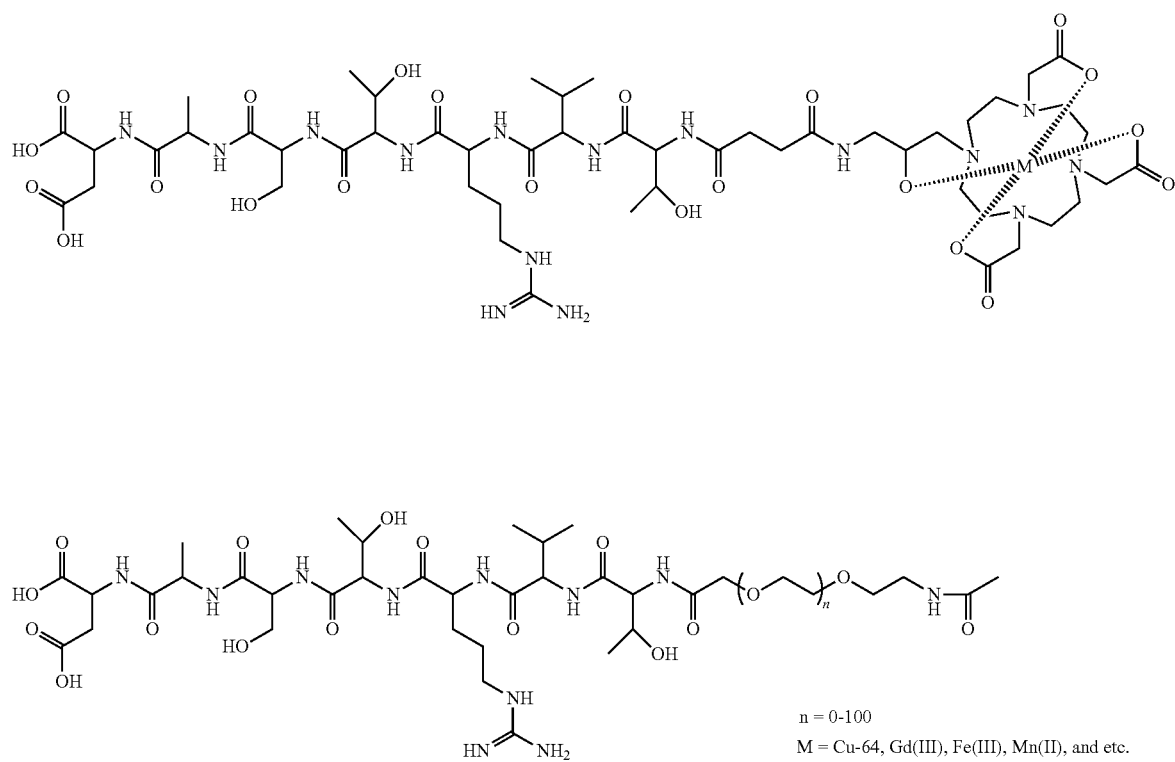

n = 0-100
M = Cu-64, Gd(III), Fe(III), Mn(II), and etc.

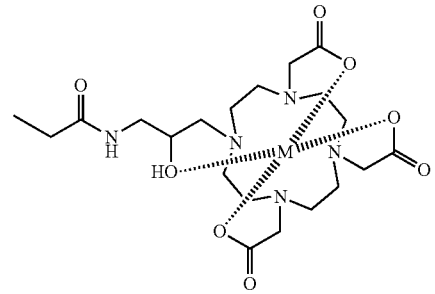

Figure 12:
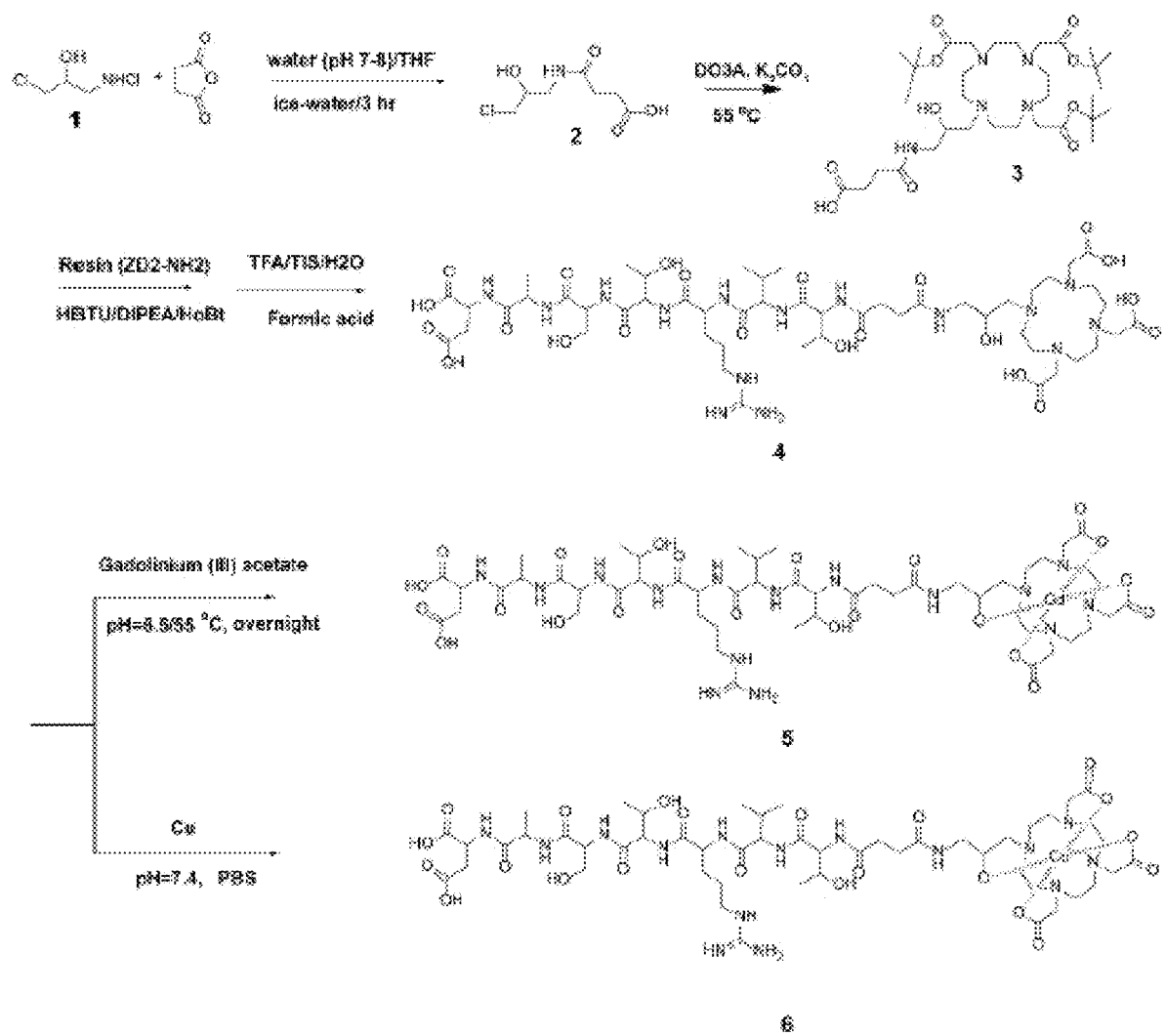
FIG. 12 illustrates the synthesis route of ZD2-Gd(HP-DO3A) and ZD2-Cu(HP-DO3A) as MRI and PET probes, respectively.

Chemical Synthesis (FIG. 12)

(1) Synthesis of 2 Amino-3-chloro-2-propanol hydrochloride (2.9 g, 20 mmol) was dissolved in pure water (20 mL). Succinic anhydride (2.1 g, 21 mmol) was dissolved in THF (20 mL) and dropwise added to the solution (pH 7-8, adjusted by $Na_2CO_3$ aqueous solution) at 0° C. Then the magnetic stirring and reaction continued overnight. THF was removed under reduced pressure and the mixture was cold-dried. Finally, the product was purified by silica gel column (methanol:DCM=1:5) to have 2 (yield 86%).

(2) Synthesis of DO3A-Boc-1-Amino-2-propanol, 3 to a 250 mL round-bottom was added 1.5 g (1.4 mmol) of tris-t-butyl-DO3A and 0.87 g (6.3 mmol) of $K_2CO_3$. The flask was charged with 40 mL of DMF (Change this to acetonitrile). The flask was sealed and placed under a nitrogen atmosphere. 0.63 g (3.0 mmol) of 2 was dissolved in 2 mL of DMF (Change this to acetonitrile) and added to the solution of tris-t-butyl-DO3A. The reaction was heated to 50 degree and stirred overnight. The reaction was monitored by mass spectrometry to follow the disappearance of the starting material. The reaction was checked by MALDI-TOF to determine the disappearance of tris-t-butyl-DO3A. Once all of the tris-t-butyl-DO3A had disappeared, the reaction was filtered and evaporated to provide a yellow oil. The oil was dissolved in minimal methanol and 100 ml of diethyl ether was added and the flask was placed at −20 degree overnight. The white precipitate was filtered and washed with cold ether. M/Z observed: 688.589, calculated: 687.44 [M].

(3) Synthesis of DO3A-ZD2, 4 After ZD2 was synthesized through solid phase chemistry and deported with piperidin/DMF (20% v/v), compound 3 (4 eqiv) was dissolved in DMF and added to the solid phase column with DIPEA, followed by reaction for 2 h. the resulting product was cleaved from resin using TFA/TIS/H2O (v/v 96.5:1:2.5) and stirred at room temperature for 3 hours. Then the product was precipitated in cold ether twice and dried under reduced vacuum to have 4. M/Z observed: 1249.886, calculated: 1249.62 [M]. (yield: 95%).

(4) Synthesis of Gd-DO3A-ZD2, 5 Compound 4 was redissolved in water 30 ml and $Gd(OAc)_3 \cdot 6H_2O$ was added. The pH was adjusted to ~6.5 with 1M NaOH and the reaction was heated to 50 degree. The pH was adjusted back to 6.5 every 6-10 h until no further change occurred (typically 1-2 days). The reaction was evaporated and purified by reverse phase HPLC, retention time of 18.77 min and 95% purity to yield 5 as a white powder after cold-dry. M/Z observed: 1403.645 [M]+ and 1425.73 [M+Na]+, calculated: 1403.51[M]+ and 1425.61 [M+Na]+.

Materials and Methods

Animals

Male athymic nude mice were purchased from Case Comprehensive Cancer Center (Cleveland, Ohio, USA) and housed in the Animal Core Facility at Case Western Reserve University. All animal experiments were performed in accordance with the animal protocol approved by the CWRU Institutional Animal Care and Use Committee. Athymic nude male mice were subcutaneously injected with 100 μL cell suspension ($4 \times 10^7$ cells/mL) in matrigel matrix (Corning Bioscience, Corning, N.Y.) to initiate tumors. Mice with tumors of 5-8 mm in diameter were used for imaging studies.

MR Imaging

MR images of tumor bearing mice were acquired on an Aspect M3 small animal MRI scanner (1 Tesla). Mice were placed on a holder with the temperature maintained at 37° C., with isoflurane/oxygen mixture supplied to the mice through a nose cone. A thin catheter filled with PBS was connected to a tail vein of the mice. After mice were placed in the coil, a pilot scan was performed to adjust mice to the proper location in the coil. An axial T1 weighted sequence (TR=500 ms; TE=9 ms; Flip angle=90°; Field of view=3 cm×3 cm; Matrix size=128×128×8; slice thickness=2 mm; interslice distance=1 mm) was then used to acquire the images of the tumors before and 10 min, 20 min and 30 min after contrast injection. Images were exported into DICOM data, which were then processed and analyzed using Matlab (Natick, Mass., USA). The contrast to-noise ratio of tumors in the images were calculated as the difference between tumor mean intensity minus muscle mean intensity, divided by the noise.

Results

Differential Imaging Based on T1-Weighted MR Molecular Imaging

Figure 13A:
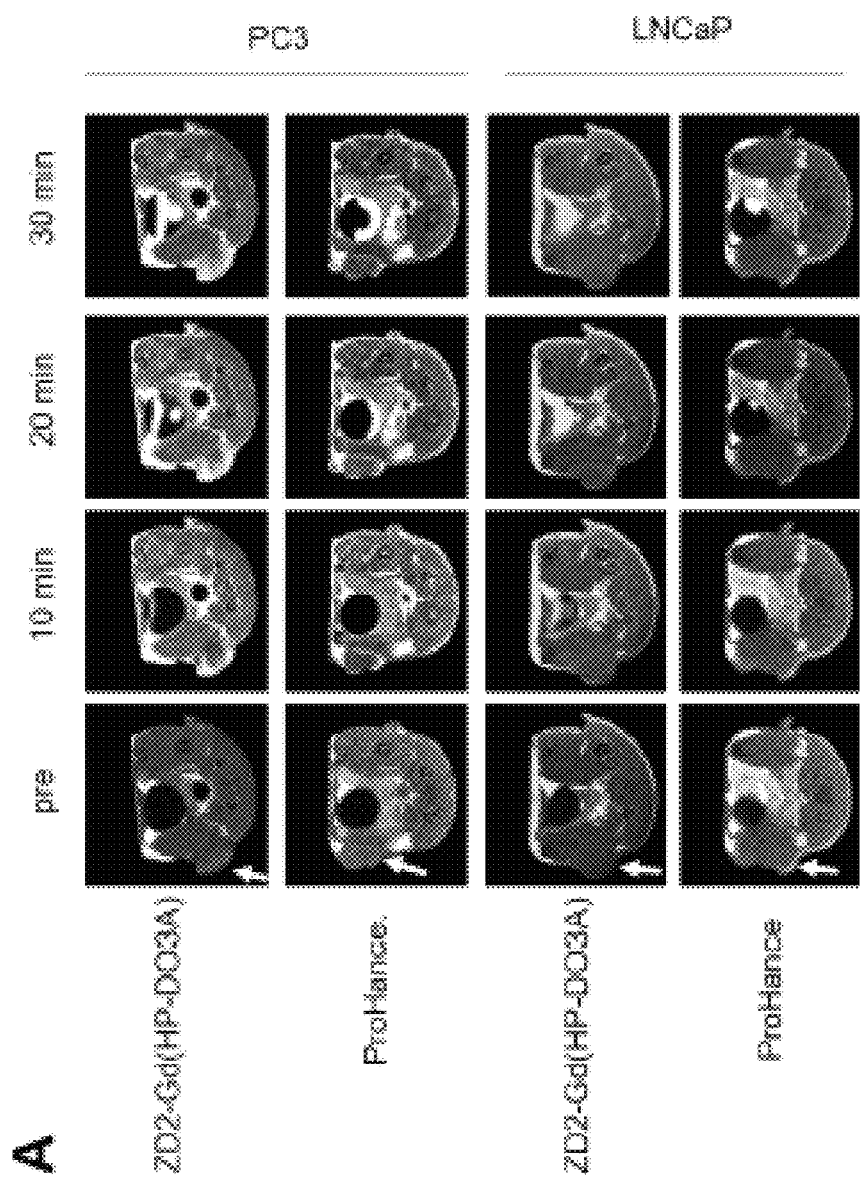
FIGS. 13(A-B) illustrate A. Representative axial MRI images of PC3 and LNCaP tumor models at tumor location. White arrows indicate tumors. B. Quantitative analysis of tumor contrast to-noise ratio (CNR) before and 10 min, 20 min and 30 min after injection of 0.1 mmol/kg ZD2-Gd(HP-DO3A).
Figure 14:
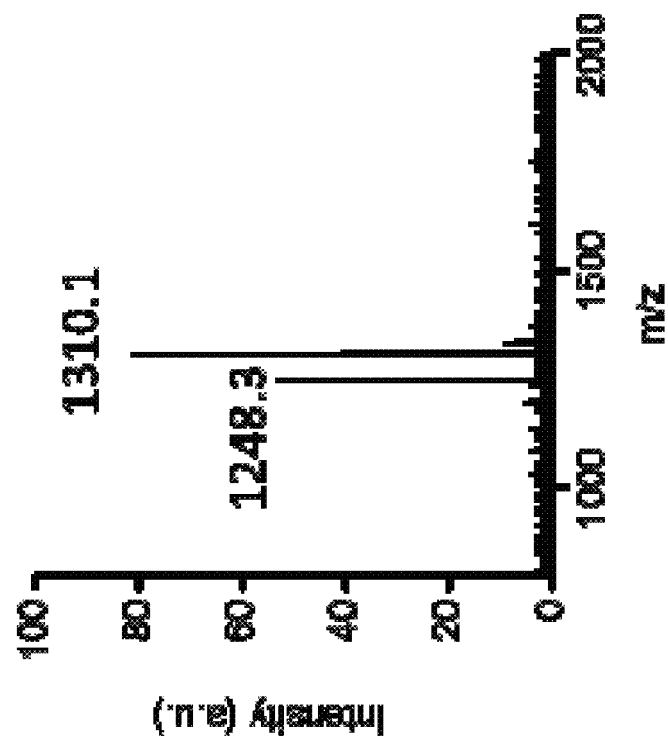
FIG. 14 illustrates representative PET images of PC3 and LNCaP tumor models at tumor location with ZD2-Cu64 (HP-DO3A). Arrows indicate tumors B FIGS. 15(A-G) illustrate synthesis and characterization of ZD2-Gd(HP-DO3A). A) synthesis route of ZD2-Gd(HP-DO3A). Briefly, ZD2 peptide was synthesized (yielding compound 1) and conjugated with Fmoc-NH-(PEG)-CH$_2$CH$_2$COOH (yielding compound 2) and 5-hexynoic acid (yielding compound 3) in solid phase. Compound 3 and 4 were reacted using click chemistry to produce ZD2-Gd(HP-DO3A). B) MALDI-TOF mass spectrum (detected molecular weight: 1600.2 Da; calculated molecular weight: 1601.79 Da) of ZD2-Gd(HP-DO3A). C) reversed-phase high performance liquid chromatography (RP-HPLC) analysis of ZD2-Gd(HP-DO3A). D) Sensorgram measured by surface plasma resonance (SPR) analysis of varying concentrations of ZD2-Gd(DO3A). E) Plot of response/concentration versus response for the Sensorgram shown in (c) yields the binding affinity of 1.7 μM between ZD2-Gd(HP-DO3A) and EDB protein (organ trend line). Data that represent a weak binding site was also shown (blue trend line). F) Plot of 1/T1 measured by T1 mapping in phantom containing increasing concentration of ZD2-Gd(HP-DO3A) (abbreviated as ZD2) in PC3 tumor lysates. G) Plot of 1/T1 measured by T1 mapping in phantom containing increasing concentration of ProHance (abbreviated as Pro.) in PC3 tumor lysates. Fitting of the data yielded r1 relaxivities of 4.12 mM$^{-1}$ s$^{-1}$ for ZD2-Gd(HP-DO3A) and 3.17 mM$^{-1}$s$^{-1}$ for ProHance.
Figure 13B:
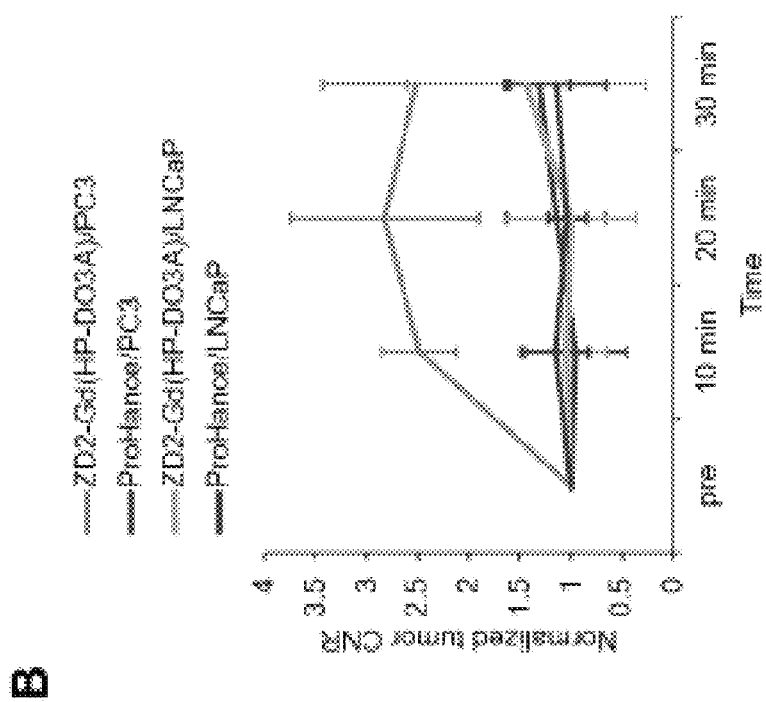

We determined the effectiveness of contrast enhanced MRI with ZD2-Gd(HP-DO3A) in differential imaging of prostate cancer in mice bearing subcutaneous PC3 and LNCaP prostate tumor xenografts. T1-weighted MR images of the tumor models were obtained before and at different time points after intravenous administration of 0.1 mmol/kg ZD2-Gd(HP-DO3A). Strong signal enhancement was observed in the PC3 tumors with ZD2-Gd(HP-DO3A) and remained prominent for at least 30 min post-injection (FIG. 13A). In contrast, the LNCaP tumors showed a significantly lower signal enhancement with ZD2-Gd(HP-DO3A) (FIG. 13A). The non-targeted clinical control ProHance only resulted in modest contrast enhancement in both the PC3 and LNCaP tumors (FIG. 13A). As shown in FIG. 13B, the contrast-to-noise ratio (CNR) in the PC3 tumors showed an over two-fold increase at 10 min after ZD2-GD(HP-DO3A) injection. ZD2-Gd(HP-DO3A) did not produce significant contrast enhancement in LNCaP tumors. These results suggest that molecular MRI of EDB-FN with ZD2-Gd(HP- DO3A) can effectively and specifically differentiate high-risk prostate tumors from low-risk ones.

PET Imaging Agent

PET imaging agents can be easily prepared using compound 4 (ZD2-HP-DO3A) as the precursor. Copper-64 labeling can be performed in a plastic sealed tube, heated to 45° C. in phosphate buffer saline (pH 7.4), for 30 min with intermittent shaking. Compound 4 of 200 µg is sufficient for complete chelation of 10 mCi of Copper 64, and the resulting solution can directly be used for injection.

Example 4

Materials and Cell Culture

All reagents for chemical synthesis were purchased from Sigma Aldrich unless stated otherwise. PC3 and LNCaP cells were purchased from American Type Culture Collection (ATCC, Manassas, Va., USA), and grown in RPMI medium (Thermo Fisher Scientific, Waltham, Mass., USA) supplemented with 10% Fetal Bovine Serum (FBS) and 1% Penn/Strep at 37° C. in 5% $CO_2$. To construct GFP-expressing cell lines, cells were transfected with lentivirus as previously reported. Matrigel 3D culture was formed following the 3D "on-top" protocol. Briefly, a glass-bottom plate was coated with a thick layer of freshly thawed matrigel, followed by solidifying the matrigel at 37° C. for 15-30 min. Cells were then plated onto the coated plate with medium containing 5% matrigel. The culture was maintained for at least 4-6 days and then ZD2-Cy5.5 (250 nM) was added to the culture medium. After 1 h, cells in the 3D matrigel were imaged with confocal laser fluorescence microscopy.

Animals

Male athymic nude mice were purchased from Case Comprehensive Cancer Center (Cleveland, Ohio, USA) and housed in the Animal Core Facility at Case Western Reserve University. All animal experiments were performed in accordance with the animal protocol approved by the CWRU Institutional Animal Care and Use Committee. Athymic nude male mice were subcutaneously injected with 100 µL cell suspension ($4 \times 10^7$ cells/mL) in matrigel matrix (Corning Bioscience, Corning, N.Y.) to initiate tumors. Mice with tumors of 5-8 mm in diameter were used for imaging studies.

Quantitative PCR Analysis of Cancer Cells

Total RNA were isolated from cells using RNeasy Plus Kit and reverse-transcribed into cDNA using high capacity cDNA Transcription Kit. Semiquantitative real-time PCR was performed using a SYBR Green Master Mix (Life Technologies, Carlsbad, Calif.).

Western Blotting

Tumors and normal murine tissues were homogenized in 200-500 µL T-PER buffer (Thermo Fisher Scientific, Rockford, Ill., USA) mixed with protease inhibitor cocktail (Sigma-Aldrich, St. Louis, Mo., USA) and the resulting lysates were centrifuged for 10 min at 10,000 g at 4° C. The supernatants were collected and protein content was determined by BCA assay (Bio-rad). Protein extracts (20 µg) were subjected to SDS-PAGE, followed by blotting onto a PVDF membrane. The blots were washed and incubated with 1:1000 anti-EDB-FN BC-1 antibody (Abcam, Cambridge, Mass., USA). HRP-conjugated anti-mouse IgG antibody was used as secondary antibody. Anti-β-actin antibody was used as loading control. The blots were developed using the ChemiDoc XRS System (Bio-rad).

MRI Contrast Agent Synthesis

The ZD2 peptide sequence, TVRTSAD (SEQ ID NO: 1), was synthesized in solid phase using Fmoc chemistry. A short spacer, Fmoc-9-amino-4,7-dioxanonanoic acid (Fmoc-NH-$PEG_2$-$CH_2CH_2$COOH), and 5-hexynoic acid, were also sequentially conjugated in solid phase followed by trifluoroacetic acid (TFA) treatment, which yielded ZD2-PEG-propargyl. Azido-Gd(HP-DO3A) was synthesized as reported previously. Click chemistry reaction between ZD2-PEG-propargyl (1 Eq) and azido-Gd(HP-DO3A) (1.1 Eq) was performed in a 2:1 mixture of t-butanol and water under nitrogen following addition of $[Cu(MeCN)_4]PF_6$ (0.02 Eq) and TBTA (Tris[(1-benzyl-1H-1,2,3-triazol-4-yl)methyl]amine, 0.02 Eq). The final product, named ZD2-Gd(HP-DO3A), was purified by high performance liquid chromatography (HPLC) on an Agilent 1100 HPLC system equipped with a semi-preparative C18 column. The gradient of HPLC was 100% water for 10 min and 0-20% acetonitrile in water for another 20 min and 50-100% acetonitrile in water for 5 min. The Gd(III) content was measured by inductively coupled plasma optical emission spectroscopy (ICP-OES Optima 3100XL, Perkin-Elmer, Norwalk, Conn.). ZD2-Gd(HP-DO3A) was characterized by matrix-assisted laser desorption/ionization time-of-flight (MALDI-TOF) mass spectrometry on a Voyager DE-STR spectrometer (PerSeptive BioSystems) in linear mode with R 2,5-dihydroxybenzoic acid as a matrix (M+1: 1600.2 Da; 1601.79 Da (calc.). HPLC was used to characterize the purity of the product using the same gradient for production. The fibrin-FN clot targeting contrast agent, CREKA-Gd (HP-DO3A), was synthesized with a similar approach. It was characterized by MALDI-TOF mass spectrometry (M+1: 1457.87 Da; 1459.56 Da (calc.)). The binding affinity of the contrast agent to EDB protein was measured using surface plasma resonance (SPR) according to a previous protocol. Briefly, different concentrations of the contrast agent were injected to a CM5 series S chip surface (GE Healthcare Life Science, Ohio, USA) coated with immobilized EDB proteins. Sensorgrams generated from the binding between contrast agents and EDB were recorded with Biacore T100 (GE healthcare, Waukesha, Wis.), and analyzed using Scatchard plot. Affinity was calculated by fitting data into a linear line, with the slope of the line representing $-1/K_d$.

Fluorescence Probe Synthesis

Synthesis of the fluorescent probe, ZD2-PEG-Cy5.5 was achieved by conjugating ZD2-PEG on resin to Cy5.5 NHS ester (Lumiprobe, Hallandale Beach, Fla., USA), followed by TFA treatment. The product was precipitated in cold ether and freeze dried and characterized by MALDI-TOF mass spectrometry (M=1: 1473.76 Da: 1472.78 Da (calc.)). Concentration of ZD2-PEG-Cy5.5 in PBS was quantified by measuring the absorbance at 450 nm.

Relaxivity Measurement at 7T

To accurately capture T1 maps, a fast T1 mapping method was developed. This accelerated multi-slice T1-mapping method combines a saturation recovery look-locker sequence and spiral k-space sampling[40]. The NMR tubes filled with 3.12-50 µM ZD2-Gd(HP-DO3A) were positioned in a mouse coil and scanned with T1-weighted spin echo sequence, cartesian T1-mapping sequence, and spiral T1-mapping sequence. Axial images were acquired. CNR values from the T1-weighted sequence were calculated from signal from the samples subtracting surrounding water signal, and divided by noise. T1 values of the samples were reconstructed by fitting signal change during the acquisition time to the adapted T1-relaxation curve.

In Vitro Transmetallation

Aqueous solutions (0.1 mL, 2 mM-Gd) of ZD2-Gd(HP-DO3A) and ProHance were mixed with 0.9 mL human serum and incubated at room temperature for 2 h. The plasma mixtures were transferred to CF-10 centrifugal filters (molecular weight cut-off 10 KDa) and centrifuged at 4,000 rpm and 25° C. for 150 min. During centrifugation, the solution in the upper reservoir was agitated using a pipette every 20 min for the plasma mixtures. The content of metal ions in both the upper reservoir and the filtrates was determined by ICP-OES after appropriate dilution. The degree of transmetallation of the contrast agents with Zn(II) or Cu(II) ions in the plasma was evaluated using the percentage of Zn(II) or Cu(II) ions filtered through the membrane, calculated as Zn(Cu) %=(concentration of Zn(II) or Cu(II) in the filtrates)/(total Zn(II) or Cu(II) concentration before centrifugal filtration)×100. Human serum was used a control.

In Vivo Transmetallation

Balb/c mice (Charles River Laboratories, Wilmington, Mass., USA) were randomly divided into groups of ZD2-Gd(HP-DO3A) and ProHance (n=5) and placed in the metabolism cages, 48 hours prior to injection. After acclimatization, the mice were injected with either ZD2-Gd(HP-DO3A) or ProHance at a dose of 0.1 mmol-Gd/kg via tail vein. Urine samples were collected at 12 h pre-injection, and then 8, 24, 48, and 72 h post-injection from the metabolic box. The collected urine samples were centrifuged at 4,000 rpm for 15 min. The concentration of Gd(III), Zn(II), Cu(II), and Ca(II) in the supernatant of the urine samples was determined by ICP-OES after appropriate dilutions.

Biodistribution

PC3 tumor-bearing athymic nude mice (sixteen mice) were randomly divided into 4 groups (four mice each group). Then two of the groups were injected with either ZD2-Gd(HP-DO3A) or ProHance at a dose of 0.1 mmol-Gd/kg via tail vein. The animals were sacrificed at 2 and 7 days after injection. The blood and tissue samples, including brain, femur, heart, lung, liver, muscle, spleen, and kidney, were collected and weighed. The tissue samples were then cut into small pieces and mixed with ultra-pure nitric acid (1.0 mL, 70%, EMD, Gibbstown, N.J.). The tissue samples were liquefied within 2 weeks and the solution was transferred to a centrifuge tube and centrifuged at 14,000 rpm for 15 min. The supernatant (0.2 mL) was diluted with 9.8 mL deionized water and further centrifuged at 14,000 rpm for 15 min. The Gd(III) concentration in the final supernatant was measured by ICP-OES. The average Gd(I) content in each organ or tissue was calculated from the measured Gd(III). In addition, 8 LNCaP tumor-bearing mice were also tested with similar injections of ZD2-Gd(HP-DO3A) and ProHance (n=4). The Gd content in different organ/tissues was calculated as the percentage of injected dose per gram of organ/tissues (% Dose/g).

Histological Analysis

After fluorescence imaging of the organs, they were embedded in O.C.T and sectioned at 5 μm thickness, and mounted on to glass slides. The slides were fixed and permeabilized with cold acetone, followed by blocking with 1% BSA for 1 hour. DAPI or EDB-FN specific antibody, BC-1 (Abcam, Cambridge, Mass.), were applied subsequently for staining. Unbound antibodies were washed with TBS-T (0.1%). Alexa Fluor 594-conjugated goat anti-mouse IgG H&L (Abcam) was used as the secondary antibody. Prolong Gold antifade solution (Invitrogen, Grand Island, N.Y.), was used to cover the slides. The stained tissue sections were imaged using confocal laser scanning microscopy.

Ex Vivo Fluorescence Imaging

The targeted binding of ZD2-Cy5.5 to the prostate tumor was assessed ex vivo using Maestro FLEX In vivo Imaging System (Caliper Life Sciences, Hopkinton, Mass.) using a red filter set (spectral range of 630-910 nm, 1000 ms exposure time). ZD2-Cy5.5 (10 nmol) was administered to study the in vivo distribution of ZD2-based probes. At 3 h post-injection, the mice were sacrificed to image the tumors and the organs.

In Vivo MRI

All MRI experiments were performed on a horizontal 7T Bruker scanner (Bruker Biospin Co., Billerica, Mass.). Imaging experiments were performed when the tumor size reached 5-8 mm in diameter. ZD2-Gd(HP-DO3A) was administered intravenously at the dose of 0.1 mmol/kg after acquiring pre-contrast images. Post-contrast images were obtained at 10 min interval up to 30 min. The axial slices of mouse at the tumor location were acquired using T1-weighted spin echo sequence with the following parameters: field of view (FOV): 3 cm; slice thickness: 1.2 mm; interslice distance: 1.2 mm; TR: 500 ms, TE: 8.1 ms; flip angle: 90°; average: 2; matrix size: 128×128. Contrast-to-noise ratio (CNR) at each time point was calculated by subtraction of the average signal intensity in the tumor and muscle, divided by the standard deviation of image noise. ProHance® (gadoteridol) was used as a control in the imaging experiments.

T1 Mapping

The following imaging parameters were used for T1 mapping methods: flip angle 10°; echo time 2.09 ms; slice thickness 1 mm; number of average 1; field of view 3×3 cm$^2$; matrix size 128×128. For each slice, 50 images that covered 5 s of the saturation recovery curve were acquired within an interval of 100 ms. Proton density (Mn) images were acquired with repetition time (TR) of 2 s. Cartesian MRSLL images were also acquired as a validation of spiral MRSLL method. Center 64 k-space lines were acquired in Cartesian method as described previously. Other acquisition parameters were the same as spiral MRSLL.

Results and Discussions

Contrast Agent Synthesis and Characterization

The small molecular targeted MRI contrast agent ZD2-Gd(HP-DO3A) was synthesized by conjugating EDB-FN-targeting peptide ZD2 to a clinical macrocyclic agent ProHance® [Gd(HP-DO3A)] (FIG. 15A). The final product was characterized by MALDI-TOF mass spectrometry (FIG. 15B) and HPLC (FIG. 15C). ZD2-Gd(HP-DO3A) exhibited a binding affinity of 1.7 μM (FIGS. 15D and 15E) to EDB fragment, which is sufficient for reversible binding, so as to produce detectable signal enhancement of the molecular target in contrast enhanced MRI, as well as to facilitate rapid clearance from the body post-imaging and minimize potential side-effects. ZD2-Gd(HP-DO3A) demonstrated high chelation stability, comparable to its clinical analog ProHance, with no evident transmetallation during 24 hours of incubation with endogenous metal ions $Cu^{2+}$, $Ca^{2+}$, and $Zn^{2+}$ in PBS (pH=7.4) (FIG. 16A). ZD2-Gd(HP-DO3A) had the same high stability as ProHance over both the linear agents MultiHance® and OmniScan® against transmetallation in blood plasma containing $Cu^{2+}$, $Ca^{2+}$, and $Zn^{2+}$ ions (FIG. 16B). This superior chelation stability is critical to minimizing potential side effects of the targeted contrast agent for its clinical application.

EDB-FN Upregulation is Associated with the Metastatic Phenotype of Prostate Cancers Unlike LNCaP cells, PC3 cells exhibit typical characteristics of post epithelial-to-mesenchymal transition (EMT)

phenotype, including loss of E-cadherin and upregulation of N-cadherin and vimentin (FIG. 17A). This EMT signature is strongly associated with enhanced cancer cell migration, metastasis, and drug resistance. Importantly, EDB-FN expression is significantly upregulated in PC3 cells as compared to LNCaP cells (FIGS. 17A and 17B), indicating that EDB-FN is a molecular marker of high-risk prostate cancer. It is interesting to note that the expression of epidermal growth factor receptor (EGFR) and prostate-specific membrane antigen (PSMA) did not correlate with the metastatic potential of the two cell lines. When cultured on top of a thick layer of matrigel, LNCaP and PC3 cells displayed distinctive spheroid-forming abilities (FIG. 17C). Only PC3 cells were able to penetrate into the matrix and form 3D spheroids, resembling tumors cultured in a native microenvironment, while the LNCaP cells formed cell clusters that distributed primarily on the matrigel surface. Cy5.5-labeled ZD2 peptide (ZD2-Cy5.5) was able to bind EDB-FN secreted by the PC3 spheroids, highlighted by the dispersed red fluorescence signal from the spheroids, whereas no peptide binding was detected on the LNCaP cell clusters (FIG. 17). This specific targeting of ZD2 to aggressive prostate cancer was also validated by examining the Cy5.5 signal in the tumor and organs dissected from mice bearing PC3 and LNCaP prostate tumor xenografts, 3 hours after intravenous injection of ZD2-Cy5.5. As expected, only the PC3, but not the LNCaP tumors, showed an enhanced fluorescence signal from ZD2-Cy5.5, when compared to the respective normal mouse organs (FIG. 17E). Microscopically, ZD2 was found to colocalize with the EDB-FN fibril network in the PC3 tumor sections, whereas EDB-FN and ZD2-Cy5.5 were undetectable in the LNCaP tumor sections (FIG. 17F). The difference in the expression and distribution of EDB-FN in these two tumors was also verified by immunohistochemical (IHC) staining (FIG. 17G), indicating that upregulated EDB-FN is a promising molecular target for differential diagnosis of aggressive prostate cancer and the ZD2 peptide is an effective targeting agent for this marker.

Differential Imaging Based on T1-Weighted MR Molecular Imaging

The effectiveness of contrast enhanced MRI with ZD2-Gd(HP-DO3A) in differential imaging of prostate cancer was determined in mice bearing subcutaneous PC3 and LNCaP prostate tumor xenografts. The T1 relaxivity of ZD2-Gd(HP-DO3A) was 3.7 mM$^{-1}$s$^{-1}$ at 7T, as calculated from the measured T1 values of a multi-compartment phantom containing different concentrations of ZD2-Gd(HP-DO3A) (FIG. 18A). T1-weighted MR images of the tumor models were obtained before and at different time points after intravenous administration of 0.1 mmol/kg ZD2-Gd(HP-DO3A). Strong signal enhancement was observed in the PC3 tumors with ZD2-Gd(HP-DO3A) and remained prominent for at least 30 min post-injection (FIG. 18B). In contrast, the LNCaP tumors showed a significantly lower signal enhancement with ZD2-Gd(HP-DO3A) (FIG. 18B). The non-targeted clinical control ProHance only resulted in modest contrast enhancement in both the PC3 and LNCaP tumors (FIG. 18B). As shown in FIG. 18C, the contrast-to-noise ratio (CNR) in the PC3 tumors showed an over two-fold increase at 10 min after ZD2-GD(HP-DO3A) injection, and peaked at 30 min (CNR=23.7±1.68; n=5; SEM), which is an over five-fold increase due to the contrast agent accumulation in the tumors and clearance in the normal tissues. The CNR in LNCaP tumors only increased about 10-60% during the first 30 min after ZD2-Gd(HP-DO3A) injection (CNR=6-9), and was more than two times lower than that in the PC3 ones (CNR=12-25) (P<0.01 for 10 min and 20 min post-injection; P<0.001 for 30 min post-injection). ProHance resulted in lower CNR in PC3 tumors (CNR=7~11; P<0.05 at all time points compared to the ZD2-Gd(HP-DO3A) group), which is not significantly different from that in LNCaP tumors (CNR=7~10) (P>0.05) (FIG. 18C). ZD2-Gd(HP-DO3A) did not produce significant contrast enhancement in other organs and normal tissues similar as the clinical control ProHance. In addition, co-injection of excess free ZD2 peptide (0.5 mmol/kg) significantly reduced signal enhancement and CNR in the PC3 tumors with ZD2-Gd(HP-DO3A) (0.1 mmol/kg), due to competitive binding of the free peptide to EDB-FN in the PC3 tumors (FIG. 18C). These results suggest that molecular MRI of EDB-FN with ZD2-Gd(HP-DO3A) can effectively and specifically differentiate high-risk prostate tumors from low-risk ones.

Previous reports have shown signal enhancement of pentapeptide CREKA (Cys-Arg-Glu-Lys-Ala) targeted imaging agents specific to fibrin-FN clots in cancer imaging. CREKA-Gd(HP-DO3A) was synthesized by conjugating CREKA to Gd(HP-DO3A) to assess its potential in differential MRI of the prostate tumors and to validate the effectiveness of ZD2-Gd(HP-DO3A). Although CREKA-Gd(HP-DO3A) generated significant contrast enhancement in the periphery of both the tumors, no significant difference was observed in signal enhancement between the PC3 and LNCaP tumors (FIG. 19).

T1-Mapping Analysis

Quantitative T1 maps of the tumors were acquired before and at 30 min after the injection of ZD2-Gd(HP-DO3A) and ProHance. ZD2-Gd(HP-DO3A) resulted in the T1 decrease from 2.75±0.05 s to 1.81±0.07 s and from 3.21±0.12 s to 2.54±0.13 s for PC3 and LNCaP tumors, respectively (FIG. 20A). The maps of the changes in relaxation rate (ΔR1) before and after the contrast agent injection revealed the highest relaxation rate change in the PC3 tumors among all cases, indicating the highest accumulation of the targeted contrast agent only in the PC tumors (FIGS. 20A and 20B). Based on the relaxivity of the contrast agents measured after incubation with tumor homogenates (FIGS. 15F and 15G), the average calculated concentration was 46.7±6.2 and 20.2±2.2 μM for ZD2-Gd(HP-DO3A), and 28.5±4.9 and 32.5±6.4 μM for ProHance in the PC3 and LNCaP tumors, respectively. At the end of the T1 map acquisitions, the mice were sacrificed and the Gd concentration in their tumors was measured by inductively coupled plasma optical emission spectrometry (ICP-OES). The measured Gd concentration was slightly lower than (but still comparable to) the values obtained by the T1 mapping, possibly because of the concentration changes occurring during the time lag between T1 mapping and animal sacrificing. Nevertheless, ZD2-Gd(HP-DO3A) had significantly higher concentration in the PC3 tumors than in the LNCaP tumors and that of ProHance in both the tumors (FIG. 20C), further validating the targeting specificity of ZD2-Gd(HP-DO3A) to the metastatic PC3 tumors.

In Vivo Chelation Stability and Biodistribution of the Targeted Contrast Agent

Figure 21A:
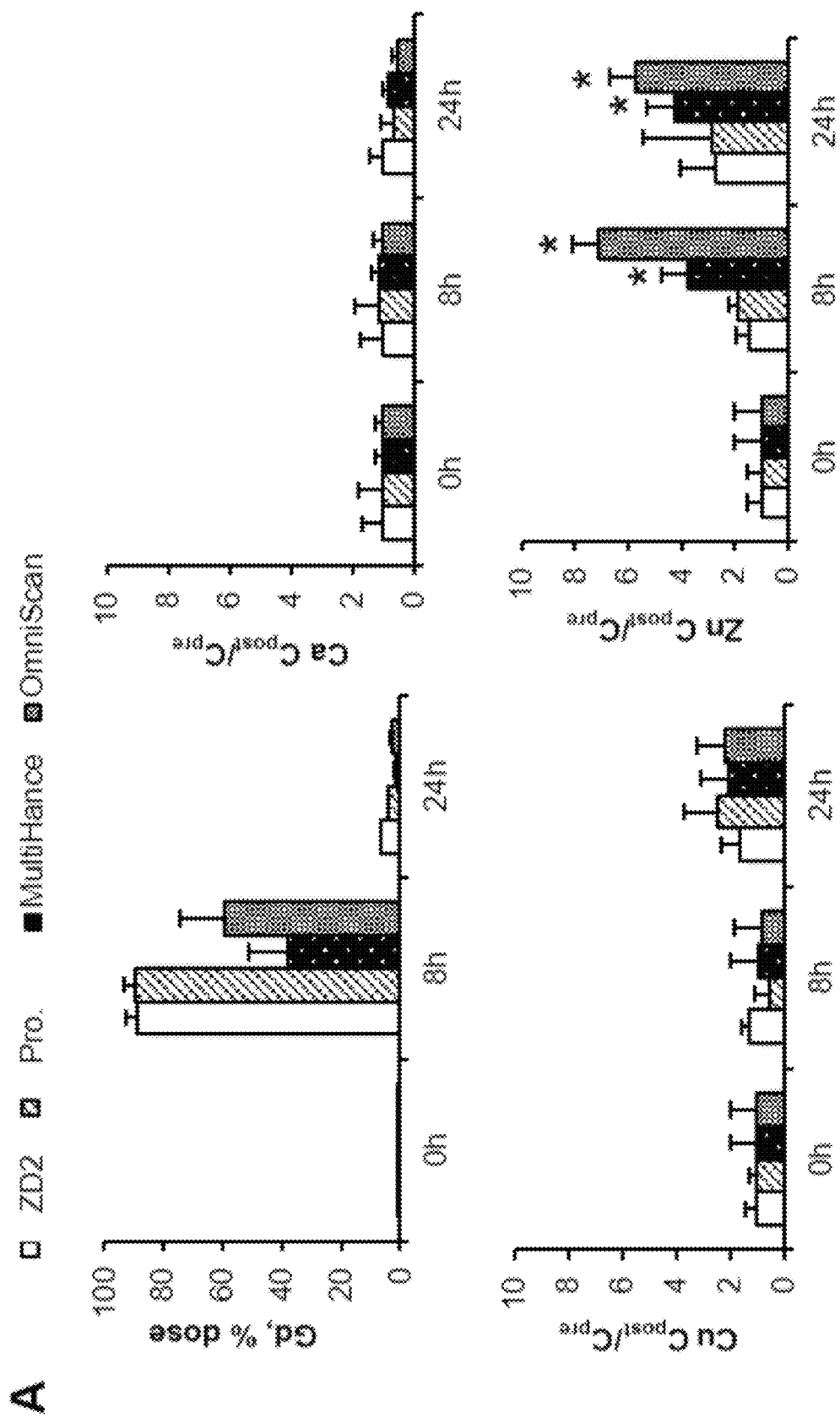
FIGS. 21(A-B) illustrate in vivo transmetallation and biodistribution of MRI contrast agents after intravenous administration. A) Gd content in urine before and at 8 h and 24 h after ZD2-Gd(HP-DO3A), ProHance, MultiHance, or OmniScan injections. B) Gd biodistribution in mouse tissues at 1 week after injection of ZD2-Gd(HP-DO3A) (n=4) or ProHance (n=3). Gd content is represented as the ratio of dose injected to the weight of the tissue. Inset: biodistribution data shown with a shorter-scale on the Y-axis. No significant difference is seen between the two groups.
Figure 21B:
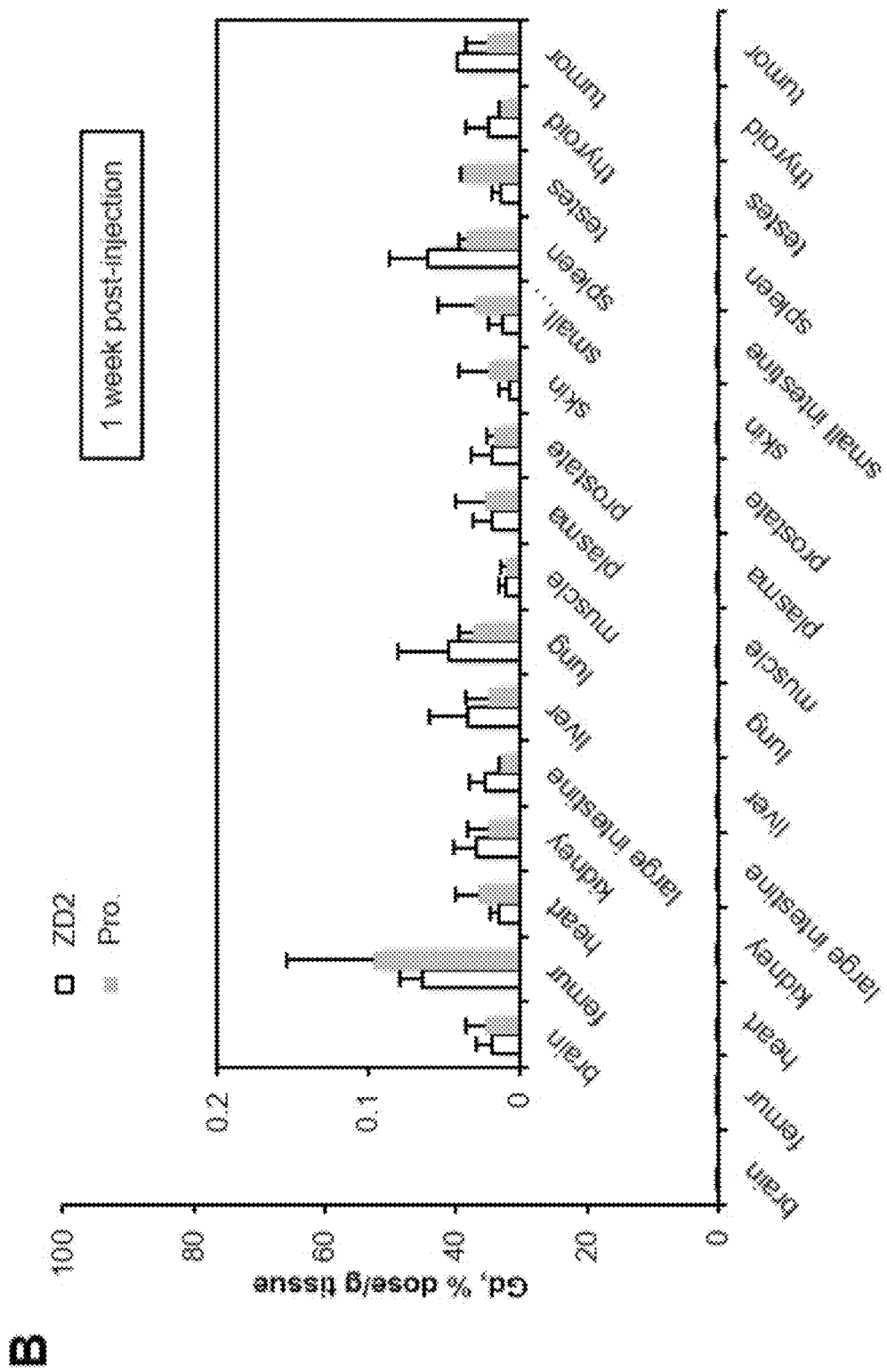

Safety is the primary concern for clinical application of gadolinium-based MRI contrast agents. The release of free Gd(III) ions from contrast agents and long-term tissue retention may cause toxic side-effects. Similar to ProHance, ZD2-Gd(HP-DO3A) underwent a rapid clearance through renal filtration with over 95% of the injected dose excreted in urine within 24 hours post-injection (FIG. 21A). ZD2-Gd(HP-DO3A) exhibited the same chelation stability as ProHance, without any significant increase in the urine concentration of these ions post-injection, when compared to pre-injection ion concentrations (P>0.05). The linear contrast agent Omniscan® resulted in significant increase in Zn(II) concentration (P<0.05). ZD2-Gd(HP-DO3A) exhibited the same low tissue retention as ProHance (FIG. 21B). The Gd(III) concentration was below the detection limit of ICP-OES in most of the organs, including the brain, heart, and skin. These results suggest that ZD2-Gd(HP-DO3A) has the same in vivo chelation stability and minimal tissue retention as well as the same safety profile compared to ProHance, one of the most stable MRI contrast agents.

Molecular imaging of the protein markers associated with tumor aggressiveness has the potential to provide accurate and non-invasive detection and characterization of high-risk tumors. Oncofetal FN subtypes, including EDB-FN, are the well-documented markers for EMT, which involves in cancer invasion, metastasis, and drug resistance. Their expression levels are inversely correlated with the survival of cancer patients. These properties of oncofetal FN imply its potential for cancer differential diagnosis and characterization with imaging. EDB-FN is highly expressed by the aggressive and androgen insensitive PC3 prostate cancer cells, not by slow-growing and androgen sensitive LNCaP cells. The expression of EGFR and PSMA, the protein markers commonly investigated for prostate cancer imaging, did not show obvious correlation with the aggressiveness of the cell lines. EDB-FN seems to be a relevant and promising protein target for characterizating the aggressiveness of prostate cancer.

High-resolution MR molecular imaging has the ability to detect and characterize aggressive tumors in the entire prostate at an early stage. However, clinical application of MR molecular imaging is limited by its low sensitivity. We have shown that this limitation can be overcome by targeting the cancer-related protein markers abundant in the ECM of aggressive tumors. Previously, we showed that molecular MRI of fibrin-FN clots was able to detect tumors, including micrometastasis. However, the clots were mainly formed by plasma FN and fibrin in the angiogenic areas of the tumor and not a specific target for differentiating two tumor models as shown in FIG. 19. The dynamic contrast enhanced MRI revealed that a sufficient amount of ZD2-Gd(HP-DO3A) rapidly bound to abundant EDB-FN in aggressive PC3 tumors to produce strong signal enhancement within first 10 minutes post-injection, which is not evident in slow growing LNCaP tumors and normal tissues, FIG. 18. The clearance of the unbound targeted agent from the non-specific tissues gradually increased the CNR only in the PC3 tumors in the first 30 minutes of contrast administration. Differential characterization of the tumor models was also confirmed by quantitative T1 mapping and quantification of the contrast accumulation in the tumors. The use of an excess of free ZD2 peptide in competitive MRI blocked the binding of the targeted agent and reduced tumor enhancement in the PC3 tumors, which validated its specificity to the protein marker. These results demonstrated the effectiveness and specificity of MR molecular imaging with ZD2-Gd(HP-DO3A) in detection and characterization of high-risk prostate cancers of high expression of EDB-FN.

In this study, a Look-Locker sequence was adopted for fast T1 mapping, and further accelerated the quantitative imaging with spiral trajectory. This method shortened the acquisition time to about 3 min 44 s using both Look-Locker sequence and $M_0$ determination. With $M_0$ determination done once in pre-contrast acquisition, a temporal resolution of 2 min 40 s with a voxel size of 0.23×0.23×1 mm$^3$ was achieved for post-contrast acquisition. This method is inherently more tolerant to Bi inhomogeneity and sensitive to contrast agent induced T1 change. The concentration of the targeted contrast agent in the different tumors determined by the T1 mapping was comparable to the Gd concentrations quantified using ICP-OES as well as consistent to the protein expression levels revealed by the immunohistochemical staining, FIG. 17. Rapid T1 mapping could be a valuable imaging tool to provide non-invasive quantitative measurement of the protein marker with the targeted contrast agent for quantitative characterization of prostate cancers.

Safety is a critical parameter for clinical application of any gadolinium based MRI contrast agent. Stability and complete excretion of the agents are essential to minimize potential toxic side effects. The reported toxic side effects are generally associated with slow excretion and poor chelation stability against transmetallation of some of the gadolinium based contrast agents, mainly DTPA based linear chelates. Macrocyclic MRI contrast agents generally have high chelation stability and good safety profile. We selected one of the most stable macrocyclic clinical contrast agents, Gd(HP-DO3A), in the design of the small peptide targeted contrast agents. The targeted contrast agent possessed the same in vitro and in vivo chelation stability as the clinical agent and the same minimal tissue accumulation, FIG. 16 and FIG. 21. The results indicate that the targeted agent ZD2-Gd(HP-DO3A) could have the same safety profile as the clinical contrast agent.

Because the EDB fragment is completely conserved in all mammalian species, MR molecular imaging of EDB-FN with ZD2-Gd(HP-DO3A) could be readily translated into clinical application in human patients and implemented in the existing clinical protocols of contrast enhanced MRI. Strong signal enhancement was observed in high-risk tumors in first 10 minutes post-injection before strong signal enhancement was observed in the bladder due to clearance of the unbound agent. This may minimize potential interference of the bladder signal enhancement on diagnostic imaging of the prostate. Nevertheless, the bladder enhancement in MRI may not be as a significant issue as in other molecular imaging modalities such as PET and SPECT, due to its high spatial resolution. This molecular imaging technology could be applied to detect, localize, and characterize high-risk tumors in the entire prostate after the initial PSA screening. Accurate detection, localization, and stratification of high-risk tumors would facilitate the earliest possible clinical interventions for the tumors, while sparing patients with indolent tumors from radical procedures. This strategy could also be used for non-invasive active surveillance of the indolent tumors. Further comprehensive preclinical and clinical assessment of the safety and effectiveness of the targeted agent contrast and MR molecular imaging is needed to warrant the clinical application of the imaging technology.

The peptide targeted contrast agent ZD2-Gd(HP-DO3A) specific to EDB-FN resulted in strong signal enhancement in aggressive PC3 prostate cancer and low enhancemeny in LNCaP prostate cancer in mouse models. The targeted contrast agent exhibits the same high in vitro and in vivo chelation stability and minimal body accumulation as a clinical contrast agent, which bode well a good safety profile for clinical translation.

Example 5

In this Example, we have identified three new small peptides specific to EDB-FN with phage display and synthesized four peptide Gd-DOTA conjugates as targeted contrast agents for MR molecular imaging of high-risk PCa. The binding pattern and affinity of ZD2 and three other peptides to the EDB-FN protein was simulated with the AutoDock software package. Specific binding of the peptides to aggressive PCa was further investigated in a mouse tumor model with fluorescence imaging. Macrocyclic chelate Gd-DOTA was used for the new targeted MRI contrast agents because of its high in vivo chelation stability. The efficacy of the targeted contrast agents for MR molecular imaging was assessed in mice with aggressive PC3 prostate tumor xenografts. All targeted contrast agents exhibited stronger tumor enhancement than a clinical contrast agent Gd(HP-DO3A).

Materials

The ligand 2,2',2"-(10-(1-carboxy-4-((4-isothiocyanatobenzyl)amino)-4-oxobutyl)-1,4,7,10-tetraazacyclododecane-1,4,7-triyl)triacetic acid (p-NCS-Bz-DOTA-GA) was purchased from CheMatech, France. All the other reagents for chemical synthesis were bought from Sigma Aldrich unless stated otherwise. PC3 cells were purchased from American Type Culture Collection (ATCC, Manassas, Va., USA) and grown in RPMI medium (Thermo Fisher Scientific, Waltham, Mass., USA) supplemented with 10% fetal bovine serum (Gibco, Gaithersburg, Md., USA) and 1% penicillin and streptomycin (Thermo Fisher) at 37° C. in 5% $CO_2$. To construct GFP-expressing cell lines, cells were transfected with lentivirus as previously reported.

Animals

BALB/c nude mice were purchased from Charles River Laboratories (Ashland, Ohio, USA) and housed in the Animal Resource Center Core Facility at Case Western Reserve University. All animal experiments were performed in accordance with the animal protocol approved by the CWRU Institutional Animal Care and Use Committee. Athymic nude mice (male) were subcutaneously injected with a 100 μL cell suspension ($4 \times 10^7$ cells/mL) in Matrigel (Corning Bioscience, Corning, N.Y.) to initiate tumor growth. Mice with tumors 5-8 mm in diameter were used for imaging studies.

Phage Display

The Ph.D C7C library (New England Biolabs, Beverly, Mass.) was used to screen for EDB-specific cyclic nonapeptides. Candidate peptides were selected by panning for four rounds. In each round, purified EDB fragment (100 μg/mL) was immobilized by overnight coating on non-treated 96-well plates (Corning Costar, Tewksbury, Mass., USA) 4° C. BSA (0.5%) was used to block non-specific binding (1 h, room temperature) followed by incubating with phages for 1 h at room temperature. Extensive washing with PBST (0.1%, 0.3%, 0.5% BSA, respectively, three times) was performed to remove non-binding phages before eluting the bound phages with 0.1 M glycine-HCl (pH 2.2) and neutralizing with Tris-HCl (pH 9.1). The eluted phages were titered and amplified with *E. coli* (ER2758), according to the user's manual. Amplified phages in the medium were purified by ultrafiltration and PEG/NaCl precipitation. At the end of round 4, properly diluted phages were cultured on LB/IPTG/Xgal plates and DNA from 29 random blue plaques was sequenced using supplied primers (New England Biolabs) along with the phage library. Peptide sequences were acquired after translating the corresponding DNA sequences.

Molecular Docking

The molecular binding models were simulated with AutoDock Vina and visualized with Python Molecular Viewer software. Before running the docking command, the receptor (EDB fragment) and all the peptides were prepared as pdbqt files. For the receptor, the nuclear magnetic resonance spectroscopy (NMR) confirmed 3D crystal structure was obtained from RSCB Protein Data Bank (PDB ID: 2fnb) as pdb file. The receptor then was opened in AutoDock Tools. Its coordinates center was set to x=−1.306, y=1.677, z=2.236. The size of the grid was set to 60×66×60. After this, all the $H_2O$ molecules were deleted and polar hydrogens were added to the receptor. At the same time, the non-polar hydrogens were merged. After this, Kollman Charge was added to the receptor. At last, the receptor was saved as pdbqt file.

For the linear peptides, their 3D conformations were converted from the 2D structures via ChemDraw 15.0 3D software. Their conformations were optimized by minimizing the energies with the force field method and then saved as mol2 files. Then the peptides were opened in AutoDock Tools. Polar hydrogens and charges were added in the same manner as described for the receptor. The rotatable bonds were selected and active torsions were set to 9. At last, the ligands were saved as pdbqt files. The AutoDock Vina was run in cmd.exe in Window10 with a configuration script which contains the coordination of the center, size of the grid, number of modes and location of the receptor, ligand and output file. The output files were obtained as txt and pdbqt files containing all the modes.

Fluorescence Probe Synthesis

The peptide was first synthesized in solid phase using Fmoc chemistry, followed by conjugation of a short PEG spacer (Fmoc-12-amino-4,7,10-trioxadode-canoic acid). Synthesis of the fluorescent probes, peptide-Cy5.5, was achieved by conjugating peptide-PEG on resin to Cy5.5 NHS ester (Lumiprobe, Hallandale Beach, Fla., USA). The cleavage cocktail composed of TFA:$H_2O$:triisobutylsilane (96.5:2.5:1) was used to remove the peptide Cy5.5 conjugates from the resin. The product was precipitated in cold ether and freeze dried. The conjugates were purified by preparative HPLC on an Agilent 1100 HPLC system equipped with a semi-preparative C18 column and characterized by matrix-assisted laser desorption/ionization time-of-flight (MALDI-TOF) mass spectrometry on a Voyager DE-STR spectrometer (PerSeptive BioSystems) in linear mode with R 2,5-dihydroxybenzoic acid as a matrix. Concentration of peptide-Cy5.5 was quantified from the absorbance at 450 nm and a fluorphore extinction coefficient of ε=209.000 L·mol$^{-1}$·cm$^{-1}$ as provided by the manufacturer.

Fluorescence Imaging

The peptide-Cy5.5 conjugates in 0.1 mL PBS (10 nmol) was administered by tail vein injection for each mouse. At 3 h post injection, the mice were sacrificed to image the tumors and the organs. The binding of peptide-Cy5.5 to the PC3 tumor and biodistribution were assessed in vivo before sacrifice and ex vivo using Maestro FLEX In vivo Imaging System (Caliper Life Sciences. Hopkinton, Mass.) with a red tilter set (spectral range of 630-910 nm, 1000 ms exposure time).

Synthesis of MRI Contrast Agent

Peptides were synthesized using solid phase chemistry. A short PEG spacer (Fmoc-12-amino-4,7,10-trioxadodecanoic acid) was then conjugated, followed by p-NCS-Bz-DOTA-GA in the presence of N,N-diisopropylethylamine in DMSO for 24 h in dark at room temperature. A cocktail of TFA:$H_2O$:triisobutylsilane (96.5:2.5:1) was applied to harvest the precursor peptide-DOTA from the resin. After the precursors were precipitated in cold ether, centrifuged and freeze-dried. The peptide DOTA conjugates were dissolved in water and complexed with $GdCl_3$ at room temperature overnight to obtain the targeted contrast agents. The peptide-(Gd-DOTA) conjugates were purified by HPLC on an Agilent 1100 HPLC system equipped with a semi-preparative C18 column. The gradient of HPLC was 100% water for 10 min and 0-20% acetonitrile in water for another 20 min and 50-100% acetonitrile in water for 5 min. MALDI-TOF mass spectra were acquired on a Voyager DE-STR spectrometer in linear mode with R 2,5-dihydroxybenzoic acid as a matrix. The lyophilized contrast agents were reconstituted in saline before use.

In Vivo MRI

All MRI experiments were performed on an Aspect M3 compact MRI scanner (1.0 Telsa, Aspect Imaging. Israel). Imaging experiments were performed when the tumor size reached 5-8 mm in diameter. Each contrast agent was administered intravenously at a dose of 0.1 mmol/kg $Gd^{3+}$ after acquiring pre-contrast images. ProHance® (gadoteridol) was used as a control in the imaging experiments. Post-contrast images were obtained at 10 min intervals up to 30 min. Axial slices of the mouse at the tumor location were acquired using a $T_1$-weighted spin echo sequence with the following parameters: TR=500 ms, TE=8.144 ms, slice thickness=1 mm, inter-slice gap=0.1 mm, field of view (FOV)=3 cm×3 cm. The total imaging time is 216 seconds. Contrast-to-noise ratio (CNR) at each time point was calculated by measuring the ratios of signal intensities in manually drawn regions of interest (ROIs) in tumor and muscle, and then normalizing to image noise. A 3D FLASH gradient echo sequence was used for whole-body coronal imaging. Imaging parameters were TR=17.362 ms, TE=6 ms, flip angle=15°, slice thickness=1.5 mm, FOV=3.5 cm×80 cm. The total imaging time is 226 seconds. Each of the 16 slices was acquired immediately after the acquisitions with the $T_1$-weighted spin echo sequence.

Results and Discussion

Receptor-Ligand Interaction Studies

Beside ZD2 (TVRTSAD) (SEQ ID NO: 1) peptide reported previously, three other sequences namely GVKSYNE (GVK), IGKTNTL (IGK), SGVKSAF (SGV) were also identified to bind to EDB-FN from the phage display. To verify the potential for ligand-receptor interactions, in-silico simulation of the binding patterns and affinities of the linear peptides to EDB-FN was investigated with Autodock Vina. The molecular docking generally visualized all the necessary interactions between the peptides and EDB fragment, which may be the binding sites for the ligands. These binding interactions include electrostatic interactions, aromatic-aromatic interactions, lipophilic-lipophilic interactions, hydrogen bond interactions and hydrophobic interactions. Even though the data from simulation is only predictive, it provides a prediction of how the peptide might bind to the receptor. Nine interaction modes for each peptide were generated and the site with the lowest binding energy and zero distance was selected. The best mode of each peptide is shown in FIG. 22. The EDB fragment is highly acidic with negatively charged residues evenly distributed on the surface, as shown in red. The predicted affinity and distance from the best mode, isoelectric point (PI), grand average of hydropathicity (GAH)[37] of the peptides are listed in Table 1. A binding affinity above 5 kcal/mol was predicted for each of the peptides.

TABLE 1

Parameters related to peptide-EDB binding.

| Peptide | Affinity (kcal/mol) | Distance from best model | | Grand average of hydropathicity | Isoelectric point |
|---|---|---|---|---|---|
| | | RMSD/lb | RMSD/ub | | |
| GVK | −7.3 ± 0.18 | 0.000 | 0.000 | −1.31 | 6.00 |
| IGK | −4.96 ± 0.21 | 0.000 | 0.000 | −0.13 | 8.75 |
| SGV | −5.91 ± 0.20 | 0.000 | 0.000 | 0.41 | 8.47 |
| ZD2 | −5.68 ± 0.15 | 0.000 | 0.000 | −0.60 | 5.50 |

Tumor Specific Binding of the Peptides

Figure 23A:
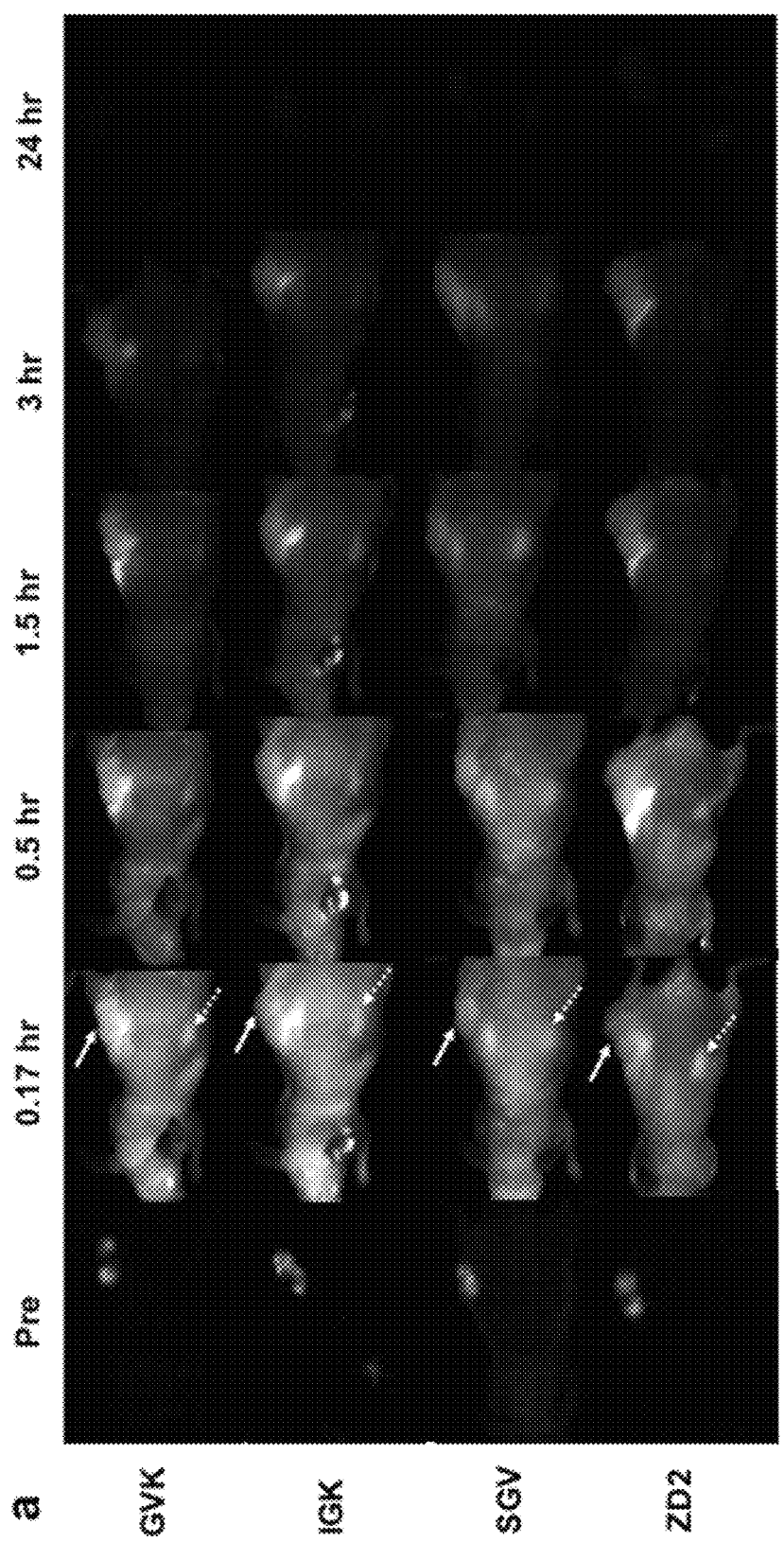
FIGS. 23(A-D) illustrate in vivo fluorescence imaging of PC3-GFP xenograft mice injected with various peptide-Cy5.5 at 10 nmol. Images were taken before and at 0.17, 0.5, 1.5, 3 and 24 hrs after injection (A); in vivo fluorescence intensity of tumors (B) and kidneys (C) under arrows over the period of 24 hrs. Tumor are indicated by full arrows, while kidneys are indicated by dotted arrows; ex vivo fluorescence images of organs at 1.5 hr post injection (D) various peptide-Cy5.5 at 10 nmol. (n=5).
Figure 23B:
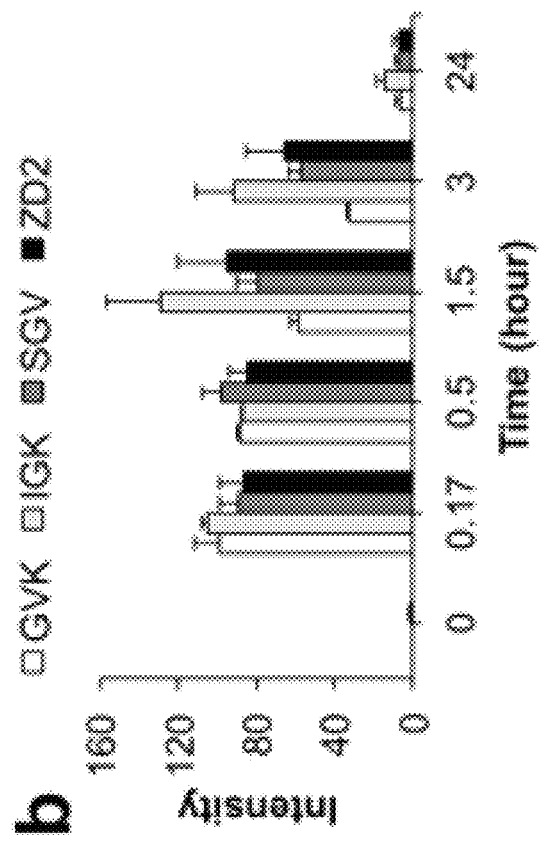
Figure 23C:
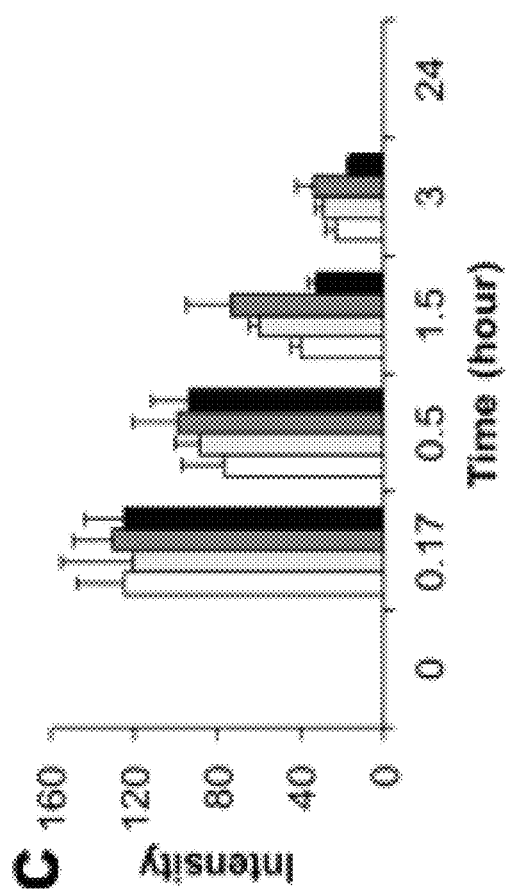

The tumor specific targeting profile and organ distribution of the peptides were investigated with in vivo and ex vivo fluorescence imaging in green fluorescence protein (GFP) labeled PC3 tumor bearing mice. The peptides were labeled with Cy5.5, a far-red emitting dye, via a short PEG spacer for fluorescence detection of the peptide. FIG. 23A shows whole body fluorescence images for in vivo tumor targeting of the peptides. Tumors were located by imaging of green fluorescence prior to injection of fluorescently labeled peptides. Substantial Cy5.5 fluorescence signal was seen in the tumor of all 4 groups at 15 min after injection and lasted for 3 hrs. At 24 hrs post injection, trace amounts of fluorescence still could be observed (FIGS. 23A and B) in the tumors. By comparison, the fluorescence intensity in the kidneys (FIGS. 23A and C) of all groups was increased significantly at 15 min after injection but decreased faster than that in the tumors. At 3 h after injection, the fluorescence intensity decreased to ⅓ of its level at 15 min (FIG. 2C) and no fluorescence could be observed at 24 hr.

Figure 23D:
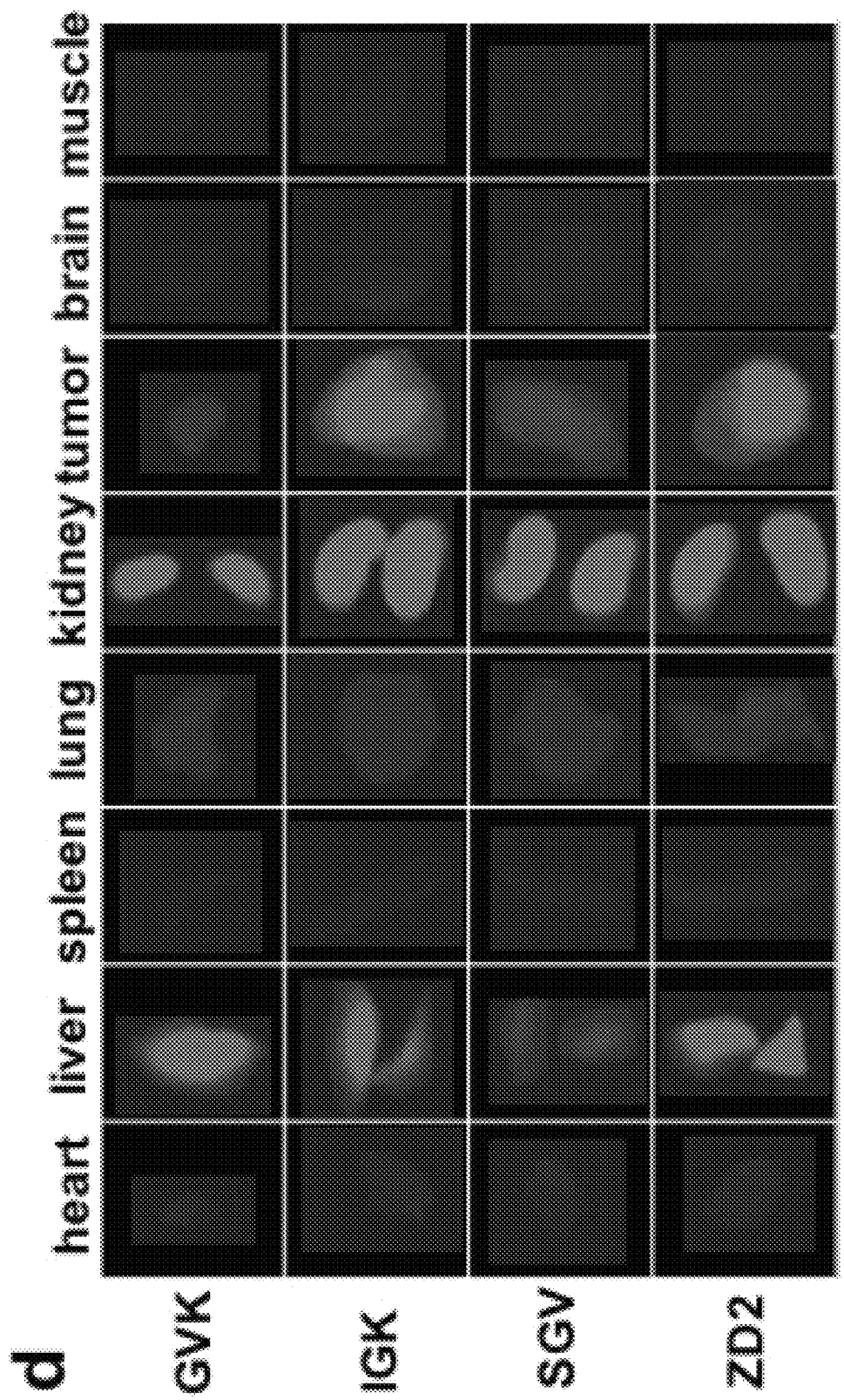

The distribution of Cy5.5 labeled peptides in organs was evaluated by ex vivo fluorescence imaging at 1.5 hr after injection. As shown in FIG. 29D, the kidney exhibited the highest fluorescence intensity, followed by liver, tumor lung and heart. Spleen, brain and muscle showed only trace amount of fluorescence. In the tumor, a difference in intensity was observed among the peptides at 90 min after administration. Specifically, greater fluorescence signals of IGK and ZD2 were seen in tumors compared to SGV, while GVK was the weakest (FIG. 23D). In normal tissues, no EDB-FN is present, so the fluorescence intensity was weak in the brain, muscle, spleen, heart and lung, consistent with our previous finding. Significant fluorescence was observed in the kidneys and liver because the small water soluble peptides with molecular weights around 1.6 kD mainly cleared via the kidneys, and then by the liver. This is logical since the molecular weight cutoff for glomerular filtration is around 30-50 kDa, far beyond these peptides with 7 amino acid residues. The short half-life and fast clearance of small peptide from circulation has been discussed extensively in literature.

Synthesis of the Targeted Contrast Agents

Figure 24:
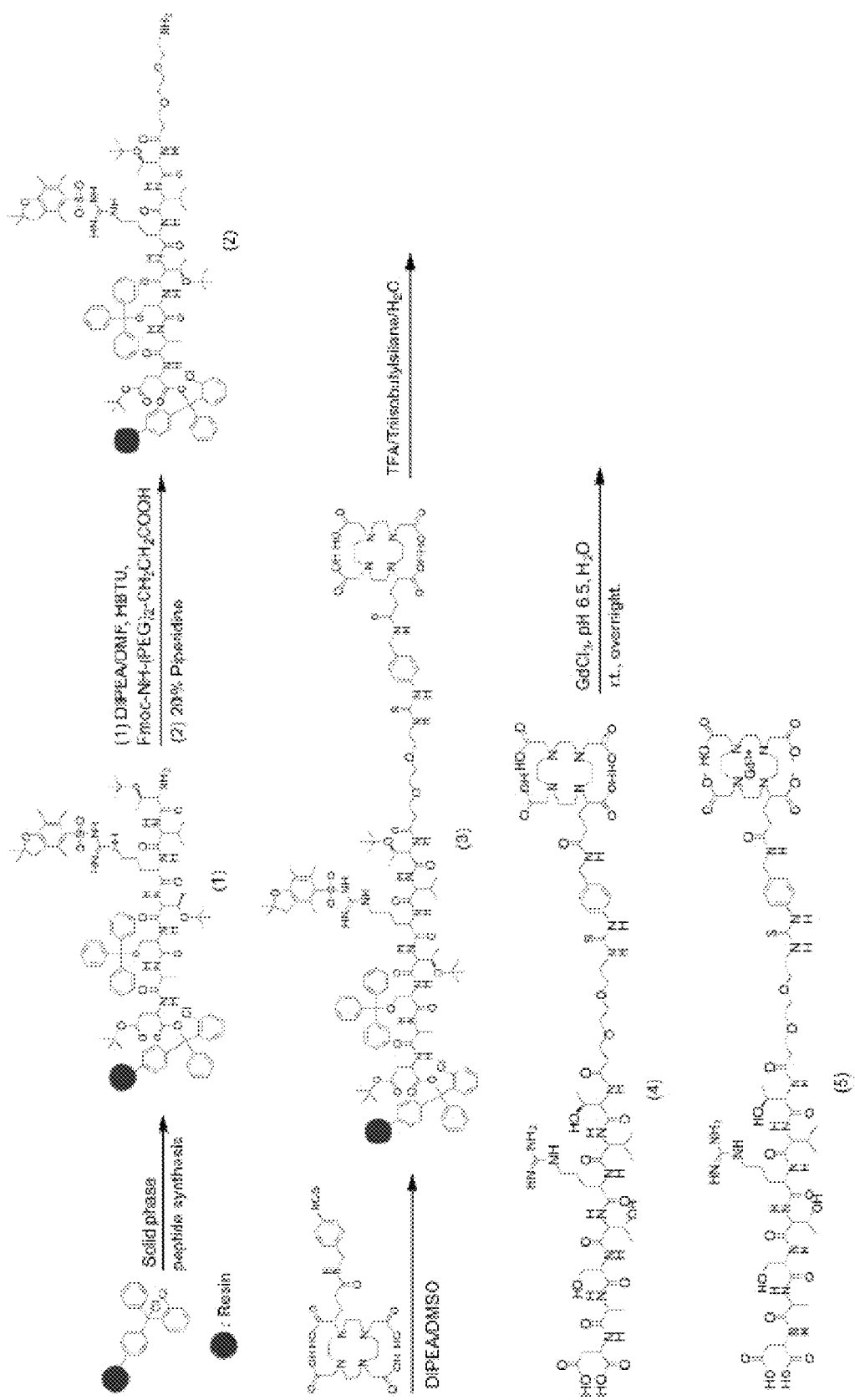
FIG. 24 illustrates a typical synthetic procedure of the targeted contrast agents with ZD2-(Gd-DOTA) as an example.

The synthesis of the MRI contrast agent peptide-(Gd-DOTA) is demonstrated in FIG. 24 with ZD2 as an example peptide. The peptides were first synthesized in the solid phase using standard Fmoc chemistry. The overall yield of compound 1 was greater than 90%. It should be noted that the addition of a spacer between the peptide and DOTA with isothiocyanate is necessary for conjugation in solid phase when TFA is used for cleaving the products from the resin. Directly linking the peptide to DOTA via isothiocyanate was unsuccessful because it underwent a cyclization with isothiocyanate and subsequent removal of the last amino acid. The addition of a small PEG spacer at the N-terminus of the peptides prevented the side reaction during cleavage of the product from the resin with TFA. The final yield of compound 4 was 80% after purification.

Figure 25:
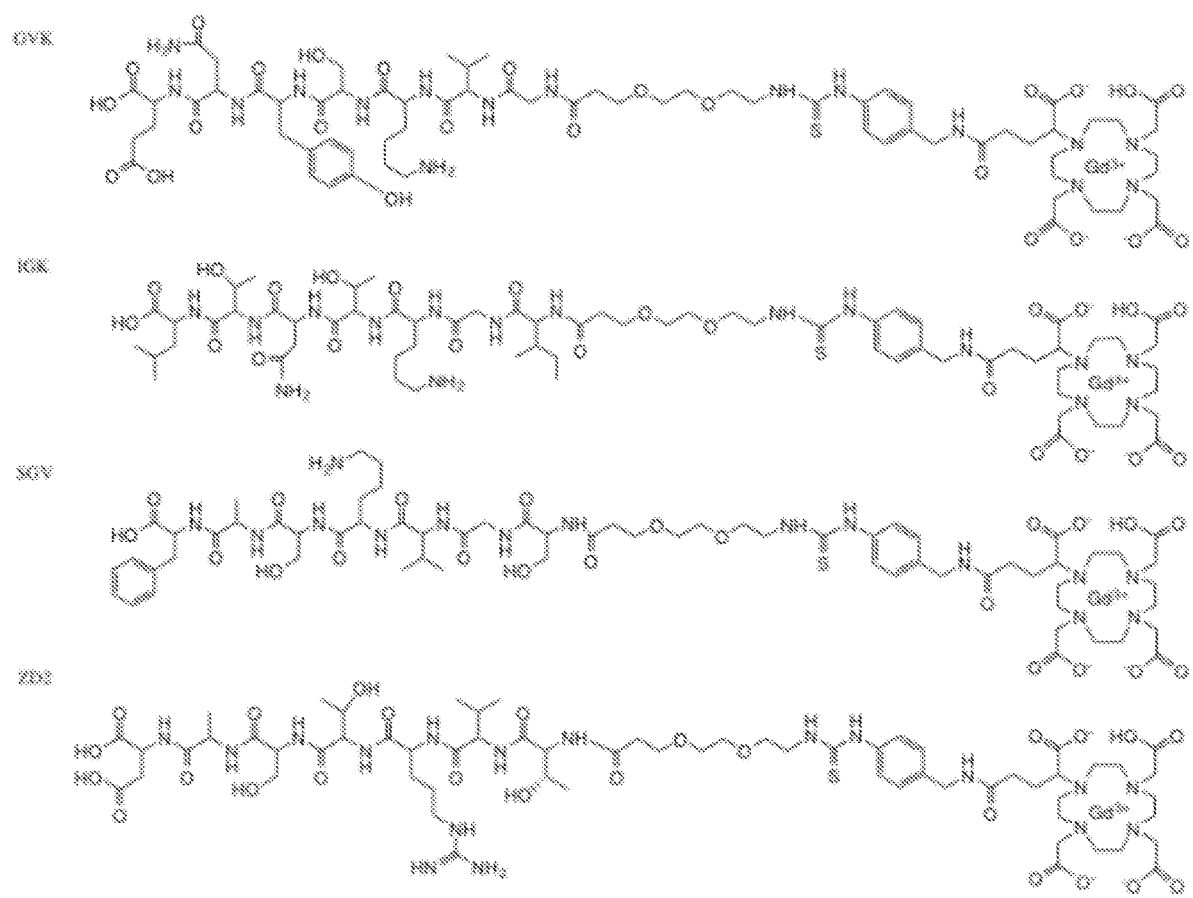
FIG. 25 illustrates the chemical structure of each contrast agent and m/z measurements of the contrast agents, IGK, ZD2, SGV and GVK.

The peptide targeted MRI contrast agents were finally synthesized by complexation of the ligands with gadolinium (III) ions. The structures of the 4 peptide-based GBCAs are shown in FIG. 25. The products were purified by preparative HPLC and characterized by MALDI-TOF mass spectrometry. The MALDI-TOF measured m/z of GVK, IGK, SGV and ZD2 targeted contrast agents were 1731.7, 1681.6, 1630.6 and 1686.5, respectively. The calculated m/z values for the agents were 1731.6, 1681.7, 1630.6 and 1686.5, correspondingly. Although the peptide-(Gd-DOTA) had an increased molecular weight around 1.6 kD as compared to the corresponding peptides, they all had good water solubility. The solid phase reaction conditions were advantageous as they allowed for easy removal of all impurities from the final product. Overall, this synthetic approach provided a facile and efficient way to synthesize the peptide-(Gd-DOTA) with good overall yield.

Relaxivity

Figure 26:
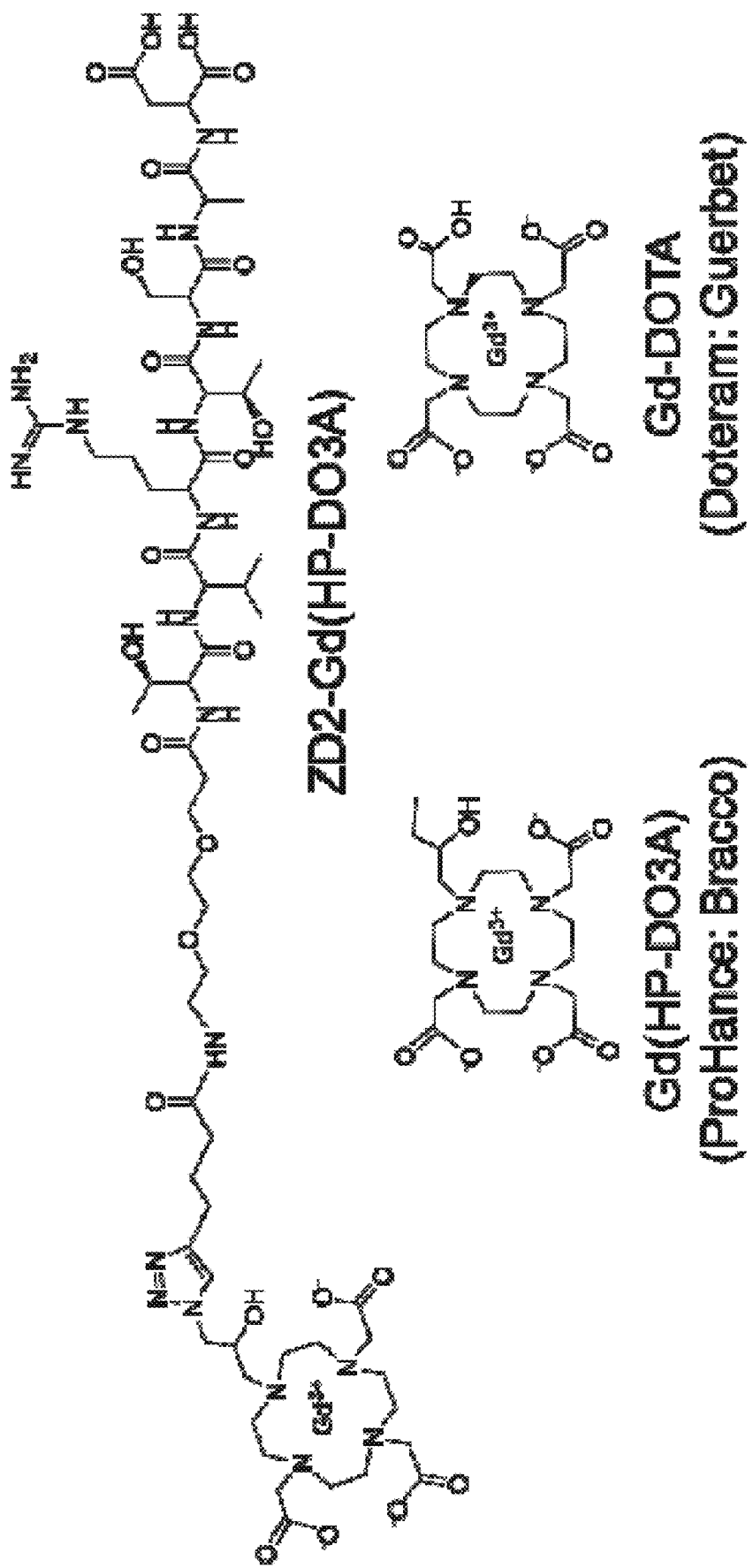
FIG. 26 illustrates the chemical structure of ZD2-Gd(HP-DO3A), Gd(HP-DO3A) and Gd-DOTA.

Relaxivity is an important parameter for an MR contrast agent. It reflects how the relaxation rate of the surrounding water proton changes as a function of concentration, and it is directly associated with the agent's contrast enhancing capability during imaging. The relaxivity of the 4 contrast agents was tested at 37° C. in water and compared to Gd(HP-DO3A), Gd-DOTA and ZD2-Gd(HP-DO3A) (FIG. 26). As shown in Table 2, The $r_1$ relaxivity for the GVK, IGK, SGV and ZD2 Gd-DOTA conjugates was 4.3, 4.6, 4.7 and 4.1 mM$^{-1}$sec$^{-1}$ at 1.5T, respectively, significantly higher than that of Gd-DOTA or Gd(HP-DO3A), which were 2.9 and 3.2 mM$^{-1}$sec$^{-1}$. The $r_2$ relaxivities for GVK, IGK, SGV and ZD2 targeted contrast agents were 5.0, 5.2, 5.6 and 4.8 mM$^{-1}$sec$^{-1}$ at 1.5T, respectively, which were also significantly higher than that of Gd-DOTA or Gd(HP-DO3A) (both 3.2 mM$^{-1}$sec$^{-1}$). ZD2-Gd(HP-DO3A) exhibited high $r_1$ and $r_2$ relaxivities of 5.4 and 6.1 mM$^{-1}$sec$^{-1}$, respectively. Compared to Gd(HP-DO3A), Gd-DOTA, the size increase of the targeted contrast agents due to the peptides and PEG spacer could result in an increase of $\tau_R$,[42, 43] thus leading to higher relaxivities.

TABLE 2

Relaxivities of the contrast agents in 1.5 T in water, 37

| Agents | $r_1$ (mM$^{-1}$sec$^{-1}$) | $r_2$ (mM$^{-1}$sec$^{-1}$) |
|---|---|---|
| Gd(HP-DO3A) | 2.9 | 3.2 |
| Gd-DOTA | 2.9 | 3.2 |
| GVK-(Gd-DOTA) | 4.3 | 5.0 |
| IGK-(Gd-DOTA) | 4.6 | 5.2 |
| SGV-(Gd-DOTA) | 4.7 | 5.6 |
| ZD2-(Gd-DOTA) | 4.1 | 4.8 |
| ZD2-Gd(HP-DO3A) | 5.4 | 6.1 |

Magnetic Resonance Imaging

Figure 27:
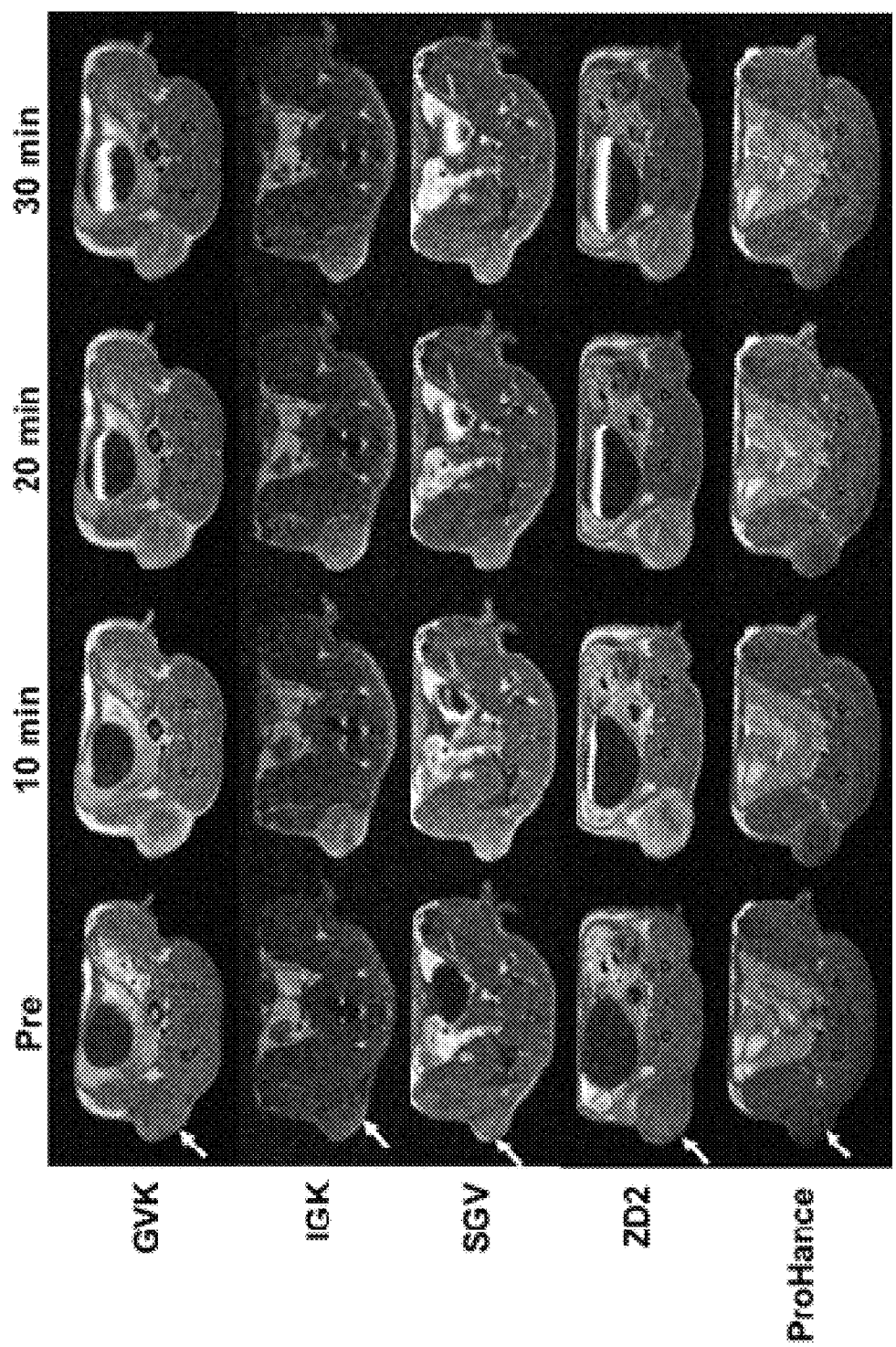
FIG. 27 illustrates $T_1$-weighted axial MRI images of PC3 tumor-bearing mice acquired pre-contrast (pre) and at 10, 20 and 30 min after i.v. injection of each contrast agent at 0.1 mmol/kg. The tumors are indicated by arrows (n=5).

The MRI contrast enhancement of each of the agents was tested in PC3 tumor-bearing mice with different MRI sequences. FIG. 27 shows the high-resolution 2D axial MR images of tumor tissues obtained a $T_1$-weighted spin-echo sequence before (pre) and at 10, 20 and 30 min after i.v. injection at a dose of 0.1 mmol/kg. Strong tumor signal enhancement was observed at 10 minutes and remained for at least 30 min post injection for the all targeted contrast agents. The results were consistent with observation from the fluorescence imaging. The non-specific clinical agent Gd(HP-DO3A) only resulted in modest contrast enhancement in the PC3 tumors. The robust signal enhancement is the tumor remained in the tumors for at least 30 minutes for the targeted contrast agents when background signal were significantly decreased. Prolonged tumor enhancement indicated the binding of the targeted contrast agents to the tumor tissues. Background noise reduction at later time points would provide better tumor delineation. The findings demonstrated the effectiveness of the contrast agents specific to EDB-FN for MR molecular imaging of aggressiveness PCa.

Figure 28:
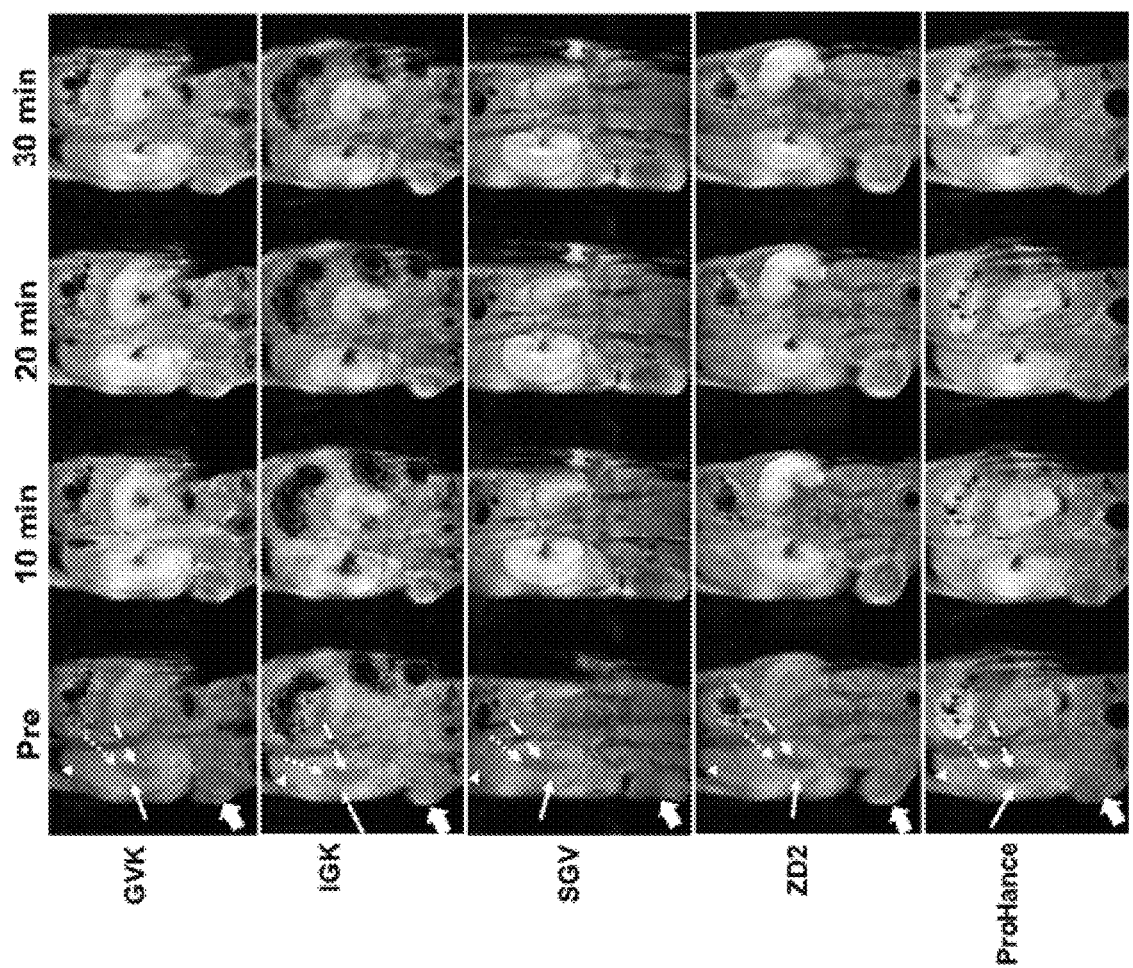
FIG. 28 illustrates $T_1$-weighted 3D FLASH coronal MR images of PC3 tumor-bearing mice acquired pre-contrast (Pre) and at 10, 20 and 30 min after i.v. injection of GVK, IGK, SGV, ZD2 Gd-DOTA conjugates and Gd(HP-DO3A) at 0.1 mmol/kg respectively. In the kidney cortex (full arrow) and outer medulla (round dot arrow), significant signal enhancement was found at 10, 20 and 30 min following injection of all peptide agents. In the inner medulla (dash arrow), high signal enhancement was found at 20 and 30 min as compared to at 10 min for the agents. In the liver, slight increase of signal (arrow head) at 10, 20 and 30 min after injection of the agents; In the tumor (block full arrow), all targeted agents produced significantly high tumor contrast enhancement as compared to the contrast agent Gd(HP-DO3A) (n=5).

Whole-body MR images enhanced with the targeted contrast agents were obtained with a $T_1$-weighted 3D FLASH sequence to assess signal enhancement in the tumors and the major organs, including the liver and kidneys. FIG. 28 shows the 2D coronal images enhanced by the targeted contrast agents. All four peptide targeted contrast agents produced significant tumor enhancement as compared to the non-specific control agent Gd(HP-DO3A), consistent with the results obtained with the spin-echo sequence. Significant signal enhancement was observed in the cortex and outer medulla of the kidneys at 10 and 20 min after injection for all the 5 agents including ProHance. The signal was increased after 20 minutes in the inner medulla, where the urine and other metabolites, including the contrast agents, concentrate and pass through the collecting duct. In the liver, only slight signal increases were observed for all the contrast agents, including Gd(HP-DO3A), suggesting that the liver was not the main pathway for clearance. Considering the same kidney signal intensity and rhythm between the peptide based GBCAs and Gd(HP-DO3A), it can be inferred that the peptide based contrast agents underwent a similar renal excretion pattern as Gd(HP-DO3A). These findings were consistent with observation from the fluorescence imaging as well as our previous report on ZD2-Gd(HP-DO3A).

Quantitative analysis of contrast-to-noise ratios (CNR) in the tumor, liver and kidneys in $T_1$-weighted 3D FLASH images further demonstrated the tumor enhancement of the targeted contrast agents. As shown in FIG. 29A, the CNR in the liver increased about three fold above baseline at 10 min after injection of all agents, and then gradually decreased to an average CNR of 2.6 at 30 min. There was no significant difference between the peptide-based contrast agents and ProHance. By contrast, the CNR in the kidneys was much higher than in the liver, in a range of 3.9-5.0, as shown in FIG. 29B. The GVK, IGK, SGV, ZD2 and Prohance groups had no significant difference in kidney CNR enhancement over the imaging period of 30 min. As shown in FIG. 29C, the CNR in PC3 tumors increased 2.9-4.4 fold at 10 min after injection and peaked at 20 min for the GVK, SGV and ZD2 targeted agents. The IGK and ProHance, however, showed a peak CNR at 10 min and then gradually decreased. Overall, ProHance resulted in lower CNR in PC3 tumors, especially at the later time points (20 and 30 min) after the injection, compared to the peptide targeted contrast agents.

MRI provides high-resolution images of soft tissues and has been routinely used in cancer detection, diagnosis, therapeutic efficacy evaluation, and image-guided interventions. However, the potential of molecular MRI for accurate detection and delineation of human cancers, including prostate cancer, has not been fully utilized because of non-specificity of the existing contrast agents. The development of cancer-specific MRI contrast agents is hampered by the low sensitivity of MRI for molecular imaging. Although significant efforts have been devoted to design nanosized targeted MRI contrast agents to improve the sensitivity of molecular MRI, the slow excretion of the nanosized contrast agents has impeded their clinical development because of the safety concerns about their long-term accumulation. For the first time, we have demonstrated the effectiveness of MR molecular imaging of cancer with clinical translatable small molecular contrast agents in animal tumor models. These agents are designed to target abundant oncoproteins in tumor extracellular matrix, including fibrin-fibronectin clots and EDB-FN. Because of the abundance of the molecular targets, a sufficient amount of the targeted contrast agents can bind to the tumors to generate robust signal enhancement for effective MR molecular imaging. The small size of the peptide targeted contrast agents allows rapid and complete clearance as the clinical contrast agents, which will alleviate the safety concerns for clinical translation.

We have shown in this example that the three new peptides are equally effective for MR molecular imaging of prostate cancer as the previous reported ZD2 peptide, although they bind to different sites of EDB protein fragment. The peptide targeted contrast agents are based on a macrocyclic contrast agent, Gd-DOTA, which is approved for its high chelation stability and minimal tissue retention, especially in the brain. The robust and prolonged signal enhancement of the targeted contrast agents in the aggressive PCa model suggests that they are promising for effective molecular MRI of prostate cancer. Nevertheless, further investigations are needed to determine their pharmacokinetics, tissue retention and safety for clinical translation. Based on our previous publications about the correlation of EDB-FN expression with tumor aggressiveness, these agents have a potential to non-invasively assess tumor aggressiveness with MRI. They can be readily incorporated into the existing protocols of multiparametric MRI for clinical management of prostate cancer.

In this example, we synthesized four new peptide Gd-DOTA conjugates specific to EDB-FN as targeted contrast agents for MR molecular imaging of prostate cancer. Computational simulation indicates that the peptides bind to different sites of the EDB fragment. The specific tumor binding of the peptides is demonstrated in mice bearing PC3 human prostate cancer xenografts. The peptide targeted contrast agents have a good water solubility and relatively high relaxivities. All of the targeted contrast agents produce robust and prolonged signal enhancement in the tumor as compared to a clinical contrast agent. Because of the high in vivo stability and good safety profile of Gd-DOTA, it is expected that the peptide targeted Gd-DOTA conjugates would have a good safety profile as the clinical agent. Besides MR molecular imaging, the EDB-FN specific peptides have a potential to deliver other imaging probes and therapeutics for cancer imaging and therapy. The targeted contrast agents have a potential to provide accurate detection and diagnosis of aggressive prostate cancer with molecular MRI.

Example 6

Methods
Materials

Succinic anhydride and o-dichlorobenzene were purchased from Sigma Aldrich (St. Louis, Mo., USA). Mono-Fmoc ethylenediamine was purchased from Combi-Blocks (San Diego, Calif., USA). N,N,N',N'-Tetramethyl-O-(1H-benzotriazol-1-yl)uronium hexafluorophosphate. O-(benzotriazol-1-yl)-N,N,N',N'-tetramethyluronium hexafluorophosphate (HBTU) and all protected amino acids for peptide synthesis were purchased from Anaspec (Fremont, Calif., USA). N,N-Diisopropylethylamine (DIPEA) was purchased from MP Biomedicals, LLS (Solon, Ohio, USA. Dimethylformamide (DMF), dichloromethane (DCM) and piperidine were purchased from Fisher Scientific (Pittsburgh, Pa., USA). $Gd_3N@C80$ was purchased from SES Research (Houston, Tex., USA). Maleimide-opfp (pentafluorophenyl 3-(2,5-dioxo-2,5-dihydro-1H-pyrrol-1-yl)propanoate) was synthesized according to a reported protocol[13].

Oxidation of $Gd_3N@C80$

At 0° C., succinic anhydride (1.5 g, 15 mmol) was added dropwise to hydrogen peroxide and the mixture was stirred for 30 min. The product was washed with pure water and filtered, followed by lyophilization for further use. Succinic acid acyl peroxide (8.0 mg, 5 equiv) was added to $Gd_3N@C80$ (10 mg) in 10 mL o-dichlorobenzene. The resultant solution was de-aerated by flashing with nitrogen and heated at 84° C. for 48 h. Additional succinic acid acyl peroxide (8.0 mg each time) was added at an interval of 12 h during the reaction. A brown sludge precipitated from the solution at the end of the reaction. Then, 20 mL 0.2 M NaOH aqueous solution was added to extract the water-soluble product. The top aqueous layer was deep brown and the bottom layer was colorless. The top layer was concentrated, adjusted to pH of 3-4 and purified with a PD10 column, and lyophilized to yield $Gd_3N@C80(OH)_{18}(CH_2CHCOOH)_6$ (2) (yield, 74%). MALDI-TOF (m/z, $[M+Na]^+$): 2221 (obsd); 2212 (calc).

Synthesis of ZD2-$Gd_3N@C80$ $Gd_3N@C80(OH)_{18}(CH_2CH_2COOH)_6$ (6 mg) and mono-Fmoc ethylene diamine (5 equiv) were dissolved in DMF, and then HBTU (5 equiv) and DIPEA (5 equiv) were added. The reaction was stirred at room temperature for 2 h. Piperidine/DMF (20%, v/v) was used to remove the protecting group of Fmoc. Afterwards, the product was precipitated in cold ether to obtain $Gd_3N@C80(OH)_{18}(CH_2CH_2COOH)_x(NH_2)_y$ (3) of brown color. (yield, 63%). $Gd_3N@C80(OH)_{18}(CH_2CH_2COOH)_x(NH_2)_y$ (3 mg) was dissolved in DMF (5 mL) and excess maleimido-opfp (20 mg) was added. The reaction continued for 30 min before precipitating in cold-ether to give maleimido containing hydroxylated $Gd_3N@C80$. ZD2-Cys peptide (sequence: Cys-Thr-Val-Arg-Thr-Ser-Ala-Asp) was synthesized in solid phase using standard Fmoc-chemistry. Excess ZD2-Cys and $Gd_3N@C80(OH)_{18}(CH_2CH_2COOH)_x(MAL)_y$ were dissolved in pure water and stirred for 30 min. Then the solution was concentrated and purified with PD10 column. The final product ZD2-$Gd_3N@C80$ was collected and lyophilized (yield, 82%). MALDI-TOF ($[M+2Na+2K+H]^+$: m/z=3927 (obsd); 3922 [estimated for $Gd_3N@C80(OH)_{18}(COOH)_2(MAL)_4$-Cys-ZD2].

Synthesis of ZD2-Cy5.5

ZD2 peptide (sequence: Thr-Val-Arg-Thr-Ser-Ala-Asp) was synthesized in solid phase using standard Fmoc-chemistry. After Fmoc removal with 10% piperidine, Fmoc-9-amino-4,7-dioxanonanoic acid (ChemPep, Inc., Wellington, Fla., USA) was added to the peptide sequence. After Fmoc removal with 10% piperidine, the resin was washed with DMF/DCM and air-dried, and 10 mg of the dried resin was swelled in DCM for 1 h, followed by reaction with 3 mg Cy5.5-NHS ester (Lumiprobe Corporation. Hallandale Beach, Fla., USA) in presence of 5 μL DIPEA. Reaction was stirred overnight at room temperature. Excess Cy5.5-NHS ester was removed by filtration and washing with DMF/DCM 10 mL 3 times. Peptides were cleaved off resin using TIPS, and precipitated in cold ether. The products were separated from ether by centrifugation at 4000×g. The final product was characterized by MALDI-TOF mass spectrometry ([M+1]⁺: m/z=1473.76 (obsd); 1472.78 (calc.)). The product was lyophilized and reconstituted in 500 µL PBS. The concentration of the solution was characterized by measuring absorbance at 650 nm.

Fourier Transform Infrared Spectroscopy (FTIR) and Relaxivity Measurement

Infrared spectrum of ZD2-Gd3N@C80 was performed using the Cary 630 FTIR Spectrometer (Agilent Technologies, Santa Clara, Calif., USA). Lyophilized hydroxylated Gd3N@C80 or ZD2-Gd$_3$N@C80 was reconstituted to a serial dilution in water. The solutions were pipetted in NMR tubes (500 µL in each tube), and placed in a relaxometer (Bruker) at 1.5 Tesla. For relaxivity measurement at 7 Tesla, NMR tubes containing contrast agent solutions were bundled and placed in a mouse coil in a horizontal 7 Tesla Bruker scanner (Bruker Biospin Co., Billerica, Mass.). T$_1$ maps of the solutions were acquired using a previously reported method[29]. $T_1$ and $T_2$ values of each solution were measured. The $r_1$ and $r_2$ relaxivities of the contrast agent were calculated as the slope of the plot of $1/T_1$ and $1/T_2$ relaxation rates against the concentrations.

Cell Culture

MDA-MB-231, Hs578T, BT549, MCF-7, ZR-75-1 and T47D were acquired from American Type Culture Collection (ATCC, Rockville, Md., USA). MDA-MB-231 cells were maintained in Dulbecco Modified Eagle Medium (DMEM) supplemented with 10% fetal bovine serum (FBS) and 5% penicillin/streptomycin (pen/strep). Hs578T, BT549 and MCF-7 cells were maintained in Eagle Minimum Essential Medium (EMEM) supplemented with 0.01 mg/ml human recombinant insulin, 10% FBS and 5% pen/strep. ZR-75-1 and T47D were maintained in RPMI 1640 medium supplemented with 10% FBS and 5% pen/strep. Three-dimensional culture of cells was achieved by an "on-top" matrigel method reported previously. Briefly, on a glass-bottom plate a thick layer of matrigel was coated, followed by plating MDA-MB-231 or MCF-7 cells on top of the matrigel. Once 3D sphere or clusters formed, ZD2-Cy5.5 was added to the medium to the final concentration of 250 nM. Binding of ZD2-Cy5.5 to the 3D spheres was evaluated using a confocal laser scanning microscope (Olympus Corporation, Tokyo, Japan) after culturing for 1 h.

RT-PCR

RNA was harvested from cells using the RNeasy Plus Mini Kit (Cat. #74134, Qiagen, Hamburg, Germany) and reverse transcription was carried out with the miScript II RT Kit (Cat. #218161, Qiagen, Hamburg, Germany), according to manufacturer's protocols. Quantitative real-time polymerase chain reaction (qRT-PCR) was performed using SYBR Green PCR Master Mix (Cat. #4309155, Applied BioSystems, Foster City, Calif., USA) and the Eppendorf RealPlex Thermocycler (Eppendorf, Hauppauge, N.Y., USA). Cycle threshold (Ct) values were evaluated by the RealPlex 2.2 software system (Eppendorf, Hauppauge, N.Y., USA). Expression levels of human EDB-FN were analyzed in triplicate by the 2-dc method and normalized to the expression levels of β-actin. Significance was found when p<0.05.

Animal Tumour Models

Female athymic nude mice were purchased from the Case Comprehensive Cancer Center and housed in the Case Center Imaging Research. All animal experiments were carried out according to a protocol approved by the IACUC of Case Western Reserve University. To initiate tumour xenografts, cells cultured in 150 mm dishes were trypsinized and centrifuged. Cell pellets from each dish were suspended in 100 µL PBS and reconstituted with Corning Matrigel Matrix High Concentration (Corning, Corning, N.Y., USA) to a concentration of 2×10⁷ cells/mL on ice. The suspended cells in 100 µL matrigel solution were injected subcutaneously in the flank of mice (4-6 weeks) using a 19-gauge needle. After injection, a plug in flank was formed due to matrigel gelling. Tumours were allowed to grow for at least a month before imaging. To prepare mice bearing Hs578T on the right flank and ZR-75-1 on the left flank or BT549 on the right flank and T47D on the left flank), ZR-75-1 and T47D cell inoculations were performed at 4 weeks prior to Hs578T and BT549 inoculations. MRI were performed at 5 weeks after inoculating Hs578T and BT549 cells.

Western Blot

The MDA-MB-231 and MCF7 tumours were collected and homogenized in 200-500 µL T-PER buffer (Thermo Fisher Scientific) supplemented with the protease inhibitor cocktail (Sigma-Aldrich) and PMSF (phenylmethanesulfonyl fluoride) (Sigma-Aldrich). Centrifugation at 10,000 g for 10 min at 4° C. was used to remove insoluble components. Protein concentrations were quantified by BCA assay (Biorad, Hercules, Calif., USA). Proteins of 25 µg were loaded for SDS-PAGE and transferred to polyvinylidene difluoride (PVDF) membranes (Invitrogen, Carlsbad, Calif., USA). The anti-EDB-FN antibody (ab154210, BC-1, Abeam, Hercules, Calif.) and fluorescein-conjugated anti-mouse secondary antibody (ab97264, Abeam) were used. The fluorescein-conjugated anti-β-actin antibody was used for visualization of β-actin. The Typhoon trio scanner (GE healthcare) was used for visualization of EDB-FN and β-actin bands using the channel for fluorescein.

Fluorescence Imaging

To determine the distribution of ZD2-Cy5.5 in the major organs and tumours, 10 nmol ZD2-Cy5.5 was injected in tumour-bearing mice through the tail vein. At 3 h after injection, mice were sacrificed. Tumours and organs were collected and imaged with CSi Maestro imaging system (Woburn, Mass., USA) using the deep red filter sets (exposure time: 1000 ms).

Histological Analysis

Tumours were embedded in Optimum Cutting Temperature Compound (OCT) and kept froze in −80° C. Tumour tissues sectioned at the thickness of 5 µm were then fixed and permeabilized with cold acetone. BSA (1%) in PBS was used to block the tissue at room temperature for 1 hour. Mouse anti-EDB-FN antibody, BC-1 (ab154210, Abcam, Cambridge, Mass., USA), diluted with 1% BSA (1:500) was applied to the tissue and incubated at room temperature for 1 hour. After extensive washing, AlexFluor594-conjugated anti-mouse IgG antibody (1:500) (Invitrogen, Eugene, Oreg., USA) was applied and incubated with the tissue for 1 hour. Tissue sections were then counterstained with Prolong Gold antifade mounting medium with DAPI (Invitrogen). Confocal laser scanning microscopy (FV1000, Olympus, Japan) was used to acquire the fluorescence images of the tissues. H&E staining of the tissue was performed at the tissue resource core of Case Western Reserve University. H&E staining images were acquired using the Virtual slide microscope VS120 (Olympus).

MR Imaging

MR images of the mice bearing MDA-MB-231 or MCF-7 tumour xenografts were acquired on an Aspect M3 small animal MRI scanner (1 Tesla). Mice were placed on a holder with the temperature maintained at 37° C., with isoflurane/oxygen mixture supplied to the mice through a nose cone. A thin catheter filled with PBS was connected to the tail vein of the mice. After mice were placed in the coil, a pilot scan was performed to adjust mice to the proper location in the coil. An axial $T_1$-weighted sequence (TR=500 ms; TE=9 ms; Flip angle=90°; Field of view=3 cm×3 cm; Matrix size=128×128×8; slice thickness=2 mm; inter-slice distance=1 mm) was then used to acquire the images of the tumours before and 10 min, 20 min, and 30 min after contrast injection. Images were exported into DICOM data, which were then processed and analyzed using Matlab (Natick, Mass., USA). The contrast-to-noise ratio of tumours in the images was calculated as the difference between tumour mean intensity minus muscle mean intensity, divided by the noise. Three-dimensional images of mice were acquired using a gradient echo $T_1$-weighted sequence with the following parameters: TR=17 ms; TE=6 ms; Flip angle=15°; Field of view=3.5 cm×8 cm; Matrix size=128×512×16; slice thickness=1.5 mm. Analysis of the change in signal intensity in muscle, heart, liver, kidney, and bladder was performed using Matlab. MRI at 7 Tesla was performed on a horizontal Bruker scanner. $T_1$-weighted spin echo sequence with the following parameters was used: field of view (FOV): 3 cm; slice thickness: 1.2 mm; interslice distance: 1.2 mm; TR: 500 ms, TE: 8.1 ms; flip angle: 90°; average: 2; matrix size: 128×128. The images were similarly analyzed as described above.

Biodistribution

The mice injected with the contrast agents were sacrificed one week post-injection. Tissue samples were collected, weighed, and digested by 1 mL ultrapure nitric acid (EMD Millipore, Billerica, Mass., USA) for 7 days. The digested sample (0.5 mL) was diluted to 5 mL with ultrapure water (Milli-Q, EMD Millipore, Billerica, Mass. USA). The solution was centrifuged and filtered using a 0.45 µm filter and the concentration of Gd(III) ions was determined using inductively coupled plasma-optical emission spectrometry (ICP-OES) on a 730-ES ICP-OES system (Agilent Technologies, Santa Clara, Calif., USA). Samples were measured at three different wavelengths for Gd at 336.224, 342.246, and 358.496 nm and the results were averaged across wavelengths. Intensities were evaluated by ICP Expert II v. 2.0.2 software and were related to the concentration by a calibration curve. A standard calibration curve was developed from a blank and seven standards from a stock solution of 1000 ppm Gd in 3% nitric acid (Ricca Chemical Company, Arlington, Tex., USA) and diluted with 2% nitric acid.

In Vitro Transmetallation Assay

We performed in vitro transmetallation assay according to the protocol reported previously. Briefly, ZD2-Gd$_3$N@C80 (0.02 mM Gd/mL) was incubated with human serum for 2 h. According to previous reports, transmetallation of Gd with $Zn^{2+}$, $Cu^{2+}$ and $Ca^{2+}$ bound in serum proteins occurs rapidly and 2 h is sufficient to study the equilibrium of transmetallation. The mixtures were then centrifuged at 4000 rpm and 25° C. for 150 min using CF-10 centrifugal filters (molecular weight cutoff 10 kDa). Metal ions in both the upper reservoir and the filtrates were quantified by ICP-OES. Transmetallation with $Zn^{2+}$, $Cu^{2+}$ and $Ca^{2+}$ bound in serum proteins resulted in increase in free $Zn^{2+}$, $Cu^{2+}$ and $Ca^{2+}$ in the filtrates. The degree of transmetallation of ZD2-Gd$_3$N@C80 with $Zn^{2+}$, $Cu^{2+}$ and $Ca^{2+}$ ions in serum was evaluated using the percentage of $Zn^{2+}$, $Cu^{2+}$ and $Ca^{2+}$ ions filtered through the membrane, calculated as Transmetallation (%)=(concentration of ions in the filtrates)/(total ion concentrations before filtration)×100. Human serum was used a control.

Statistical Analysis

All the experiments were performed in triplicates unless stated otherwise. No estimation of sample sizes was performed. No randomization or blinding was used in animal studies. Data are represented as mean±s.e.m. Analysis of differences between two groups was performed using Student's t-test assuming equal variance, and the difference was considered significant if p<0.05.

Results

Gd$_3$N@C80 was first oxidized with succinic acid peroxide and NaOH to introduce carboxyl and hydroxyl groups on the cage surface (FIG. 30). MALDI-TOF mass spectrometric analysis of the hydroxylated Gd$_3$N@C80 suggested an estimated structure of Gd$_3$N@C80(OH)$_{18}$(CH$_2$CH$_2$COOH). Some of the carboxyl groups in the hydroxylated Gd$_3$N@C80 were then converted into amines, followed by reaction with maleimido-opfp, yielding maleimido-Gd$_3$N@C80 for conjugation with thiol-bearing ZD2 peptide (FIG. 30). An excess of ZD2 peptide was used to conjugate to maleimido-Gd$_3$N@C80. The N—H and C—N peaks in Fourier transform infrared spectroscopy (FTIR) (FIG. 31A) indicated successful conjugation of the ZD2 peptide. The structure was also characterized with MALDI-TOF mass spectrometry, indicating approximately one ZD2 peptide was conjugated to each Gd$_3$N@C80.

The targeted contrast agent ZD2-Gd$_3$N@C80 showed complete water solubility (FIG. 31A), which is essential for further clinical development. The $r_1$ and $r_2$ relaxivities of hydroxylated Gd$_3$N@C80 and ZD2-Gd$_3$@NC80 were determined at 1.5 Tesla. The hydroxylated Gd$_3$N@C80 had $r_1$ and $r_2$ relaxivities of 57.1 $mM^{-1}s^{-1}$ and 98.5 $mM^{-1}s^{-1}$ per Gd ion(III), respectively (FIG. 31B). ZD2-Gd$_3$@NC80 had superior $r_1$ and $r_2$ relaxivities of 223.8 $mM^{-1}s^{-1}$ and 344.7 $mM^{-1}s^{-1}$ per molecule or 74.6 $mM^{-1}s^{-1}$ and 114.9 $mM^{-1}s^{-1}$ per Gd(III) ion (FIG. 31C), respectively. The increased relaxivities of ZD2-Gd$_3$@NC80 may be attributed to slower tumbling rate and increased rotational correlation time of the targeted agent due to the increased size after peptide conjugation. The $r_1$ relaxivity of ZD2-Gd$_3$@NC80 is almost 20 times that of clinical Gd(III)-based contrast agents, including Gd-DTPA and Gd(HP-DO3A). The high $r_1$ relaxivity of the hydroxylated Gd$_3$N@C80 is attributed to strong magnetization of the hydroxyl protons on the cage by the encapsulated Gd(Ill) ions and rapid exchange rate of the protons with water protons in the surrounding bulk. This superior relaxivity is critical to improving the sensitivity of contrast enhanced MRI, especially $T_1$-weighted MRI, for molecular imaging at low doses on most clinical scanners with relatively low magnetic field strengths (1.5 and 3 Tesla). At 7 Tesla, the $r_1$ relaxivities of hydroxylated Gd$_3$N@C80 and ZD2-Gd$_3$N@C80 were 24.68 $mM^{-1}s^-$ and 24.78 $mM^{-1}s^{-1}$ per Gd(III) ion, respectively. It appears that the slower tumbling rate and increased rotational correlation time of ZD2-Gd$_3$N@C80 had less effect on improving the relaxivities at the high magnetic field strength. ZD2-Gd$_3$N@C80 had an average diameter of 2.8 nm, as determined by transmission electron microscopy (TEM) (FIG. 31D) and dynamic light scattering (DLS) (FIG. 31E), which is smaller than the renal filtration threshold. This small size is necessary for rapid extravasation, target binding for effective molecular MRI, and the elimination of the unbound agent from systemic circulation via renal filtration.

EDB-FN expression was determined in three TNBC cell lines (MDA-MB-231, Hs578T, and BT549) and three estrogen receptor (ER)-positive breast cancer cell lines (MCF-7, ZR-75-1, and T47D) using qRT-PCR. The mRNA levels of EDB-FN in all the TNBC lines were significantly higher than those in the ER-positive cell lines (FIG. 32A). Western blot analysis also revealed abundant expression of EDB-FN in MDA-MB-231 tumours and negligible expression in MCF-7 tumours (FIG. 32B). In matrigel-based three-dimensional (3D) culture, MDA-MB-231 cells were able to form large spherical structures, indicating the aggressive nature of the TNBC cells (FIG. 32C). In contrast, MCF-7 cells formed smaller cell clusters with limited matrigel invasion, suggesting the low invasiveness of the cells (FIG. 32C). The MDA-MB-231 spheres incubated with ZD2-Cy5.5 showed strong fluorescence intensity under confocal microscopy, indicating high expression of EDB-FN protein and strong binding of the peptide probe in these spheres. In comparison, MCF-7 cells showed lower ZD2-Cy5.5 binding and weaker fluorescence intensity (FIG. 32C).

To further validate the in vivo targeting specificity of the ZD2 peptide, ZD2-Cy5.5 was intravenously injected at a dose of 0.5 μmol/kg into the MDA-MB-231 and MCF-7 tumour-bearing mice. FIG. 32D shows the fluorescence images of ZD-Cy5.5 in the tumours and other major organs at 3 hours after injection. Fluorescence intensity was greater in the MDA-MB-231 tumours than the MCF-7 tumours and normal tissues and organs. Relatively high fluorescence signal intensity was seen in the liver and kidneys, because the probe is mainly excreted via these organs. EDB-FN expression and ZD2-Cy5.5 binding in the two tumour models were also verified by correlating immunofluorescence staining of EDB-FN and Cy5.5 fluorescence imaging (FIG. 32E). MDA-MB-231 tumour sections were rich in EDB-FN expression and showed strong Cy5.5 fluorescence, while little EDB-FN expression and ZD2-Cy5.5 binding were seen in the MCF-7 tumour sections. Microscopically, the aggressive MDA-MB-231 TNBC tumour sections displayed a higher cell density than the ER-positive MCF-7 tumours (FIG. 32F). Taken together, these results validate the strong positive correlation of EDB-FN expression with tumour aggressiveness and the specific binding of ZD2-peptide to the highly abundant EDB-FN in the MDA-MB-231 tumours.

We next tested whether molecular MRI with ZD2-Gd3N@C80 at 1.0 Tesla could detect the aggressive MDA-MB-231 tumours and differentiate the aggressive TNBC tumors from MCF-7 tumours in animal models. MR image acquisition was performed with mice hearing MDA-MB-231 and MCF-7 tumour xenografts before and after intravenous injection of ZD2-Gd$_3$N@C80 at a dose of 1.67 μmol/kg or 5 μmol-Gd/kg, which is 20 times less than the standard dose of conventional clinical contrast agents, such as Gd-DTPA and Gd(HP-DO3A). Significant signal enhancement was observed in the MDA-MB-231 tumours for at least 30 minutes after the injection, while little enhancement was observed in the MCF-7 tumours or both tumours injected with non-targeted hydroxylated Gd$_3$N@C80 (FIG. 33A-B). Co-injection of 1.67 μmol/kg of ZD2-Gd$_3$N@C80 with 25 μmol/kg of ZD2 peptide significantly reduced the signal enhancement in MDA-MB-231 tumours due to competitive binding to the target. Quantitative analysis revealed that ZD2-Gd$_3$N@C80 produced 39 to 45% increase of contrast-to-noise ratio (CNR) in the MDA-MB-231 tumours (FIG. 33B). The smaller size of ZD2-Gd$_3$N@C80 facilitates rapid tumour extravasation, target binding, and clearance from circulation, and enables rapid sensitive detection of aggressive TNBC with high contrast-to-noise ratio. No significant difference was observed in signal enhancement in the normal tissues before and after contrast injection in all the tested groups, except for the excretory organs: kidneys and bladder. Increased signal intensity in the bladder indicates the excretion of unbound ZD2-Gd3N@C80 via renal filtration.

The systemic retention of both ZD2-Gd$_3$N@C80 and hydroxylated Gd$_3$N@C80 was determined at 1-week post-injection using ICP-OES. The amount of Gd(III) in the body was near the detection limit of the ICP-OES. Both the agents had less than 0.5% of the injected dose remaining in the tissues and organs at 1-week post-injection (FIG. 33C). The potential release of the free Gd(III) ions was also tested by in vitro transmetallation assay with human serum. Minimal transmetallation of ZD2-Gd$_3$N@C80 (<0.12%) was observed. Studies show that fullerene cages are highly stable and the metal ions are stably enclosed in these cages. Metallofullerene cages have been reported to even withstand exposure to (i-radiation. The minimal transmetallation seen in our study could be the result of the weak complexation of the peptide with the endogenous metal ions. Consistent with previous reports, the entrapment of the toxic Gd(III) ions in the fullerene cage prevents their systemic release and tissue interaction, which is critical for the safety of the Gd(III)-based contrast agents in consideration of clinical translation. These results suggest that ZD2-Gd$_3$N@C80 has the potential to overcome the reported toxic side effects of the existing GBCAs, caused by the release and retention of free Gd(II) ions in the body.

To potential of ZD2-Gd$_3$N@C80 for differentiating breast cancer aggressiveness was further assessed in mice bearing ZR-75-1, Hs578T, T47D, and BT549 breast cancer xenografts. The ER-positive ZR-75-1 and T47D xenografts showed a very slow rate of growth and relatively smaller tumour sizes as compared to the Hs578T and BT549 TNBC tumours. At 7 T, injection of 20 μmol Gd/kg ZD2-Gd$_3$N@C80 produced greater signal enhancement and significantly higher CNR increase in the fast-growing Hs578T and BT549 tumours than in the slow-growing ZR-75-1 and T47D tumours (FIG. 34). These results demonstrate that ZD2-Gd$_3$N@C80 is an effective high-relaxivity targeted contrast agent that can improve the sensitivity of molecular MRI for the detection and characterization of aggressive breast tumours.

This study has demonstrated that the peptide targeted gadofullerene with superior relaxivities can significantly improve the sensitivity of molecular MRI in detection and characterization of aggressive breast cancer. We have shown that the superior relaxivity of ZD2-Gd$_3$N@C80 dramatically improved the sensitivity of MR imaging of the oncoprotein EDB-FN in aggressive breast cancer. MRI with ZD2-Gd$_3$N@C80 produces robust signal enhancement in aggressive MDA-MB-231 TNBC tumours at a much lower dose (1.67 μmol/kg) at 1.0 Tesla, a sensitivity comparable with that of fluorescence imaging of ZD2-Cy5.5 (0.5 μmol/kg) in FIG. 32. The targeted contrast agent also produced strong enhancement in two other TNBC tumour models, not in slow growing low-risk tumours at a high-field strength (7 Tesla) and reduced dose. These results have demonstrated the ability of the novel targeted contrast agent for differentiating the fast-growing aggressive TNBC tumours from the slow-growing, non-metastatic, and ER-positive breast cancers. Our work pioneers effective non-invasive differentiation between breast tumours of different aggressiveness using contrast enhanced MRI. EDB-FN is also highly expressed in other types of aggressive tumours, including prostate cancer, head and neck cancer, and ovarian cancer. Therefore, molecular MRI with ZD2-Gd$_3$N@C80 can potentially be used for accurate detection and characterization of a broad spectrum of aggressive cancers, with high sensitivity and superior resolution. The low dose, rapid renal clearance, and absence of potential release of free Gd(III) ions of ZD2-Gd$_3$N@C80 are advantageous safety features for improving the safety profile of GBCAs in clinical use. Clinical translation of molecular MRI with ZD2-

Gd₃N@C80 has the potential to overcome the limitations of current imaging technologies and to significantly improve the accuracy of early detection and characterization of high-risk breast cancer for precision healthcare of cancer patients.

Example 7

Figure 35:
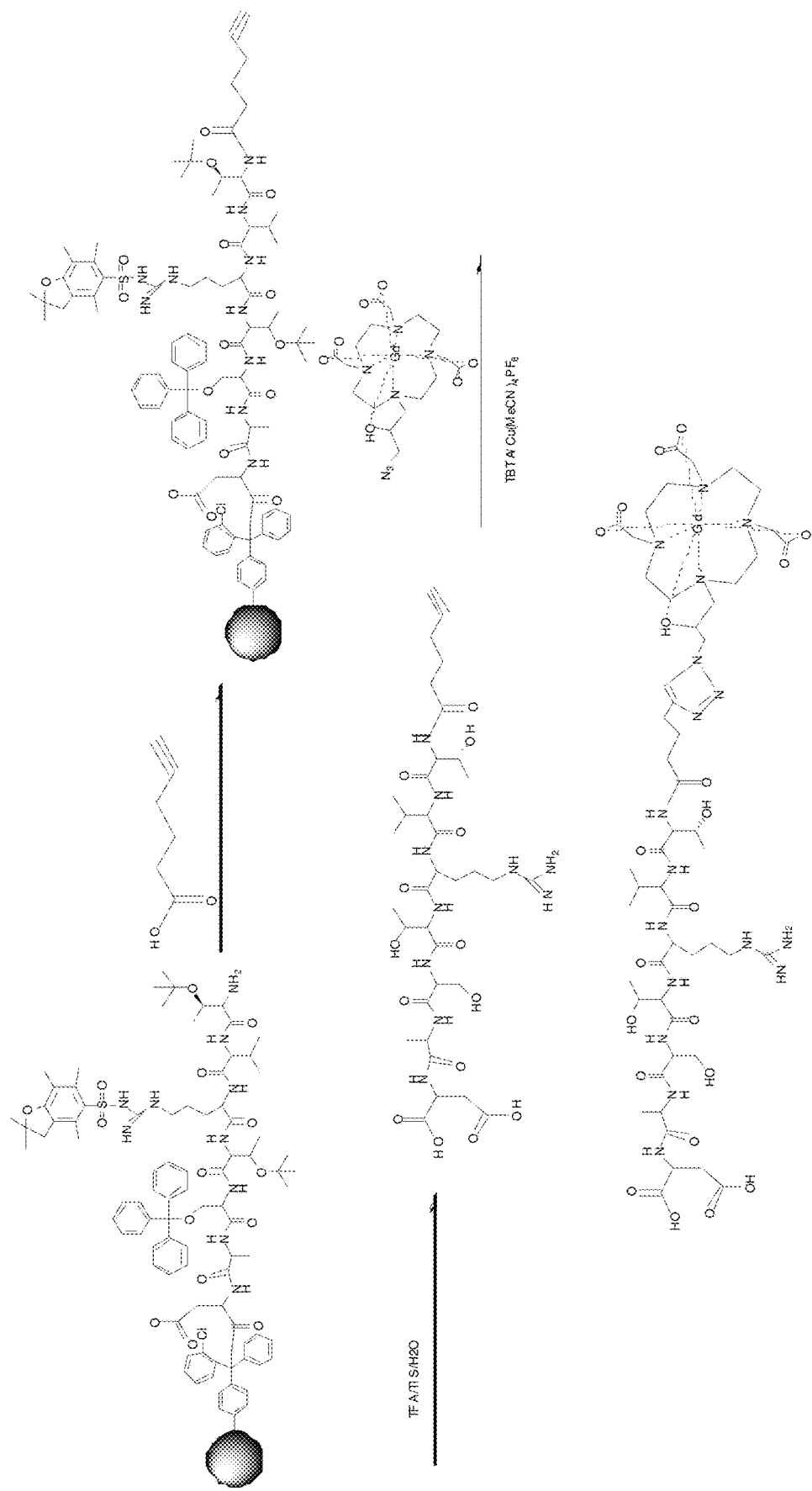
FIG. 35 illustrates Synthesis of ZD2-TA-(Gd-DO3A).
Figure 36:
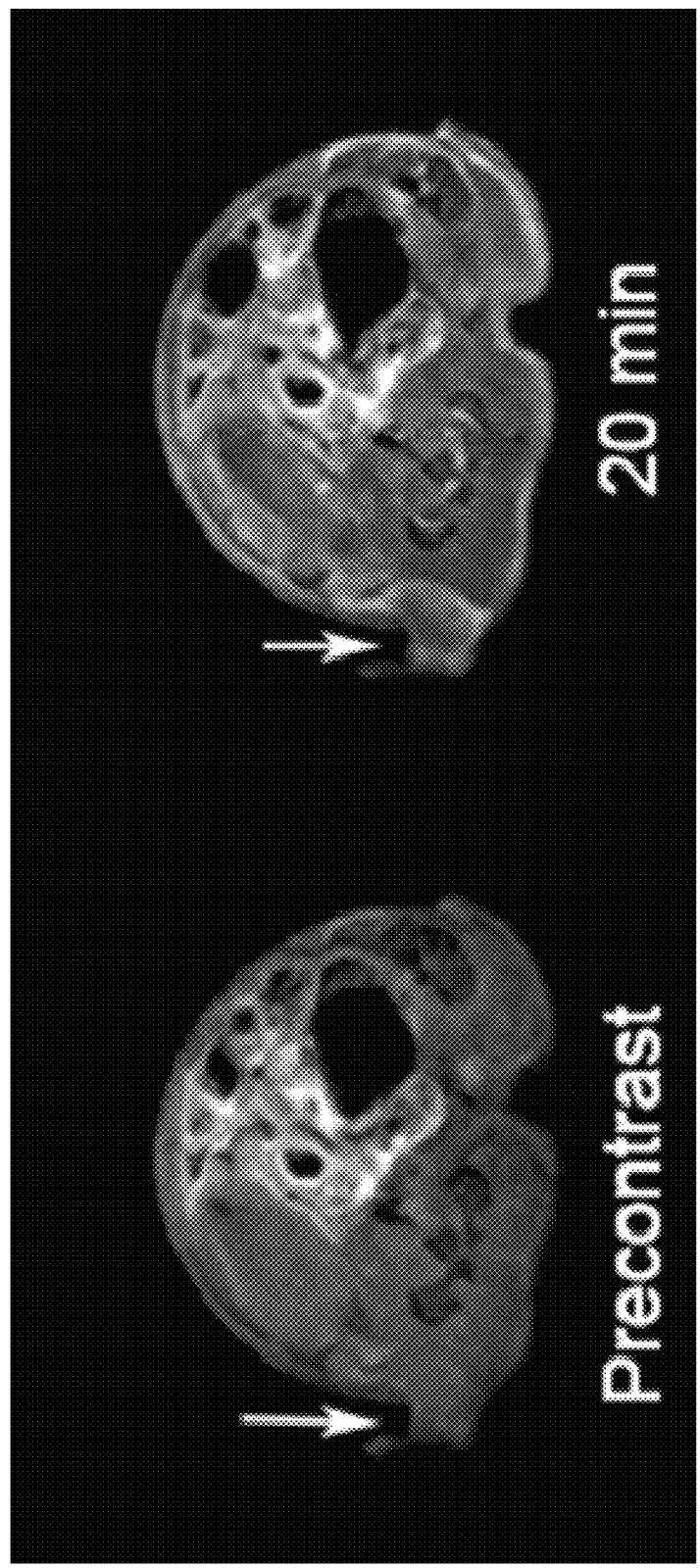
FIG. 36 illustrates MR images of prostate cancer in mice before (Precontrast) and 20 min after i.v. injection of ZD2-TA-Gd(HP-DO3A) at a dose 0.1 mmol/kg.

After ZD2 peptide was synthesized through solid phase chemistry, 5-Hexynoic Acid was added to ZD2 peptide as a spacer, then the peptide was cleavage from resin and deported with piperidin/DMF (20% v/v). (FIG. 35) Click chemistry reaction between ZD2-alkynyl (1 equiv) and azido-Gd(HP-DO3A) (1.1 equiv) was performed in a 2:1 mixture of t-butanol and water under nitrogen following addition of [Cu(MeCN)₄]PF₆ (0.02 equiv) and TBTA (Tris [(1-benzyl-1H-1,2,3-triazol-4-yl)-methyl]amine, 0.02 equiv). The final product ZD2-TA-Gd(HP-DO3A) was purified by the Biotage Flash system equipped with a C18 column. M/Z observed: 1443.4 [M+1], calculated: 1442.61 [M]. (yield: 95%). ZD2-TA-Gd(HP-DO3A) also produced significant contrast enhancement in PC3 prostate cancer at a dose of 0.1 mmol/kg. (FIG. 36)

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A molecular probe comprising:
   a linear peptide that includes an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9;
   a contrast agent selected from at least one of a metal chelating agent or metallofullerene; and
   a non-peptide linker that covalently links the peptide to the contrast agent, the linker including a carboxamide or a maleimide.

2. The probe of claim 1, wherein the non-peptide linker is a non-peptide aliphatic or heteroaliphatic linker.

3. The probe of claim 1, wherein the non-peptide linker includes an alkylene dicarboxamide.

4. The probe of claim 1, wherein the contrast agent is a magnetic resonance imaging (MRI), positron emission tomography (PET), or single photon emission computed tomography (SPECT) contrast agent.

5. The probe of claim 3, wherein the contrast agent is a metal chelating agent selected from diethylenetriaminepentaacetate (DTPA), 1,4,7,10-tetraazadodecanetetraacetate (DOTA), 1,4,7,10-tetraazadodecane-1,4,7-triacetate (DO3A), ethylenediaminetetraacetate (EDTA), 1,4,7,10-tetraazacyclotridecanetetraacetic acid (TRITA), 1,4,8,11-tetraazacyclotetradecane-1,4,8,11-tetraacetic acid (TETA), 1,4,7,10-tetraazadodecanetetramethylacetate (DOTMA), 1,4,7,10-tetraazadodecane-1,4,7-tri methylacetate (DO3MA), N,N',N'',N'''-tetraphosphonatomethyl-1,4,7,10-tetraazacyclododecane (DOTP), 1,4,7,10-tetraazacyclododecane-1,4,7,10-tetrakis(methylene methylphosphonic acid) (DOTMP), 1,4,7,10-tetraazacyclododecane-1,4,7,10-tetrakis(methylene phenylphosphonic acid) (DOTPP), or N,N'-ethylenedi-L-cysteine.

6. The probe of claim 1, having the formula:

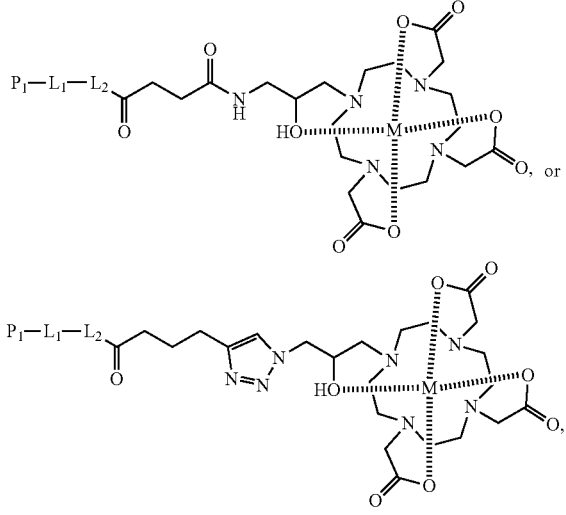

wherein:
   $P_1$ is a linear peptide having an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9;
   $L_1$ is an optional spacer,
   $L_2$ is an amino group of the peptide $P_1$ or the optional spacer if present, and
   M is a metal selected from the group consisting of $Gd^{+3}$, $Eu^{+3}$, $Tm^{+3}$, $Dy^{+3}$, $Yb^{+3}$, $Mn^{+2}$, $Fe^{+3}$, $^{55}Co$, $^{64}Cu$, $^{67}Cu$, $^{47}Sc$, $^{66}Ga$, $^{68}Ga$, $^{90}Y$, $^{97}Ru$, $^{99}mTc$, $^{111}In$, $^{109}Pd$, $^{153}Sm$, $^{177}Lu$, $^{186}Re$, and $^{188}Re$; or salts thereof.

7. The probe of claim 6, wherein $L_1$ is selected from at least one of a polyalkyleneoxide, polyvinyl alcohol, polyethylene glycol (PEG), polypropylene glycol (PPG), co-polyethylene-polypropylene glycol, polyoxyethylene (POE), polyurethane, polyphosphazene, polysaccharides, dextran, polyvinylpyrrolidones, polyvinyl ethyl ether, polyacryl amide, polyacrylate, or polycyanoacrylates.

8. The probe of claim 1, having the formula:

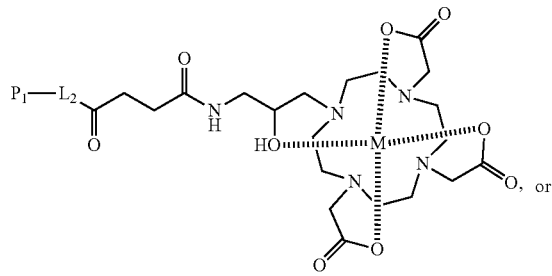

wherein:
   $P_1$ is a linear peptide having an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9;
   $L_2$ is an amino group of the peptide $P_1$, and
   M is a metal selected from the group consisting of $Gd^{+3}$, $Eu^{+3}$, $Tm^{+3}$, $Dy^{+3}$, $Yb^{+3}$, $Mn^{+2}$, $Fe^+$, $^{55}Co$, $^{64}Cu$, $^{67}Cu$, $^{47}Sc$, $^{66}Ga$, $^{68}Ga$, $^{90}Y$, $^{97}Ru$, $^{99}mTc$, $^{111}In$, $^{109}Pd$, $^{153}Sm$, $^{177}Lu$, $^{186}Re$, and $^{188}Re$, and
   n is an integer from 0 to 100; or salts thereof.

9. The probe of claim 1, wherein the metallofullerene is Gd3N@C80.

* * * * *